US012595487B2

(12) United States Patent (10) Patent No.: US 12,595,487 B2
Allen et al. (45) Date of Patent: Apr. 7, 2026

(54) METHODS AND COMPOSITIONS FOR IMPROVING AGRONOMIC CHARACTERISTICS OF C4 PLANTS

(71) Applicants: DONALD DANFORTH PLANT SCIENCE CENTER, St. Louis, MO (US); THE BOARD OF TRUSTEES OF THE UNIVERSITY OF ILLINOIS, Urbana, IL (US); THE UNITED STATES OF AMERICA, AS REPRESENTED BY THE SECRETARY OF AGRICULTURE, Washington, DC (US)

(72) Inventors: Douglas K Allen, Washington, DC (US); Jennifer J. Arp, St. Louis, MO (US); Thomas P. Brutnell, St. Louis, MO (US); Stephen P. Moose, Urbana, IL (US)

( * ) Notice: Subject to any disclaimer, the term of this patent is extended or adjusted under 35 U.S.C. 154(b) by 353 days.

(21) Appl. No.: 17/768,822

(22) PCT Filed: Oct. 15, 2020

(86) PCT No.: PCT/US2020/055820
§ 371 (c)(1),
(2) Date: Apr. 13, 2022

(87) PCT Pub. No.: WO2021/076782
PCT Pub. Date: Apr. 22, 2021

(65) Prior Publication Data
US 2024/0392307 A1 Nov. 28, 2024

Related U.S. Application Data

(60) Provisional application No. 62/915,490, filed on Oct. 15, 2019.

(51) Int. Cl.
*C12N 15/82* (2006.01)

(52) U.S. Cl.
CPC ..... *C12N 15/8243* (2013.01); *C12N 15/8261* (2013.01)

(58) Field of Classification Search
None
See application file for complete search history.

(56) References Cited

U.S. PATENT DOCUMENTS

2008/0254536 A1 10/2008 Usami et al.
2009/0025102 A1 1/2009 Hershey et al.
(Continued)

FOREIGN PATENT DOCUMENTS

WO 2010111344 A2 10/2008
WO WO-2013063344 A1 * 5/2013 ......... C12N 15/8261

OTHER PUBLICATIONS

Liu et al. "Mining of Candidate Maize Genes for Nitrogen Use Efficiency by Integrating Gene Expression and QTL Data" 2011 Plant Mol Biol Rep DOI 10.1007/s11105-011-0346-x (12 total pages). (Year: 2011).*
(Continued)

*Primary Examiner* — Matthew R Keogh
*Assistant Examiner* — Rebecca Stephens
(74) *Attorney, Agent, or Firm* — Erica Agnew

(57) ABSTRACT

C4 plants comprising a genetic disruption of the PEPCK biosynthetic pathway are provided. The plants exhibit beneficial traits when compared to wild type plants cultivated under similar growth conditions. Methods of using the plants are also provided. The growth conditions can be adverse growth conditions. Adverse growth conditions can be limiting nitrogen conditions, drought conditions, water-
(Continued)

logged conditions, high disease load, high pest load, or combinations thereof.

4 Claims, 27 Drawing Sheets

Specification includes a Sequence Listing.

(56)                    References Cited

U.S. PATENT DOCUMENTS

2009/0193538 A1    7/2009   Cheikh et al.
2017/0088825 A1    3/2017   Shukla et al.

OTHER PUBLICATIONS

Ding et al. "Identification of Photosynthesis-Associated C4 Candidate Genes through Comparative Leaf Gradient Transcriptome in Multiple Lineages of C3 and C4 Species" 2015 PLOS One DOI:10. 1371/journal.pone.0140629 (19 total pages) (Year: 2015).*

Wang et al. "Three distinct biochemical subtypes of C4 photosynthesis? A modelling analysis" 2014 J. of Exp. Botany 65(13):3567-3578. (Year: 2014).*

Cousins et.al, The role of phosphoenolpyruvate carboxylase during C4 photosynthetic isotope exchange and stomatal conductance. Plant Physiology. Nov. 1, 2007;145(3):1006-17.

Malone et. al, Phosphoenolpyruvate carboxykinase in *Arabidopsis*: changes in gene expression, protein and activity during vegetative and reproductive development. Plant and cell physiology. Mar. 1, 2007;48(3):441-50.

Rylott et. al, The gluconeogenic enzyme phospho enol pyruvate carboxykinase in *Arabidopsis* is essential for seedling establishment. Plant physiology. Apr. 1, 2003; 131(4):1834-42.

Suzuki et. al , Changes in Photosynthetic Carbon Flow in TransgenicRice Plants That Express C4-Type PhosphoenolpyruvateCarboxykinase from Urochloa panicoides, Plant Physiology, Sep. 1, 2000, ;124(1):163-72.

International Search Report and Written Opinion dated Mar. 2, 2021 in corresponding International Patent Application No. PCT/US2020/055820.

* cited by examiner

METHODS AND COMPOSITIONS FOR IMPROVING AGRONOMIC CHARACTERISTICS OF C₄ PLANTS

CROSS REFERENCE TO RELATED APPLICATIONS

This application is a U.S. National Stage Application of International Application No. PCT/US2020/055820, filed Oct. 15, 2020, which claims priority from U.S. Provisional Patent Application No. 62/915,490, filed Oct. 15, 2019, the entire contents of both of which are hereby incorporated by reference in their entirety.

STATEMENT REGARDING FEDERALLY FUNDED RESEARCH

This invention was made with government support under competitive award number 2016-6701324585 from the USDA National Institute of Food and Agriculture, award number 1812235 awarded by the National Science Foundation Plant Genome Initiative (NPGI) Postdoctoral Research Fellowships, and grant DE-SC0018277 from the DOE Department of Biological and Environmental Research. The government has certain rights in the invention.

INCORPORATION OF SEQUENCE LISTING

The present application contains a Sequence Listing that has been submitted in ASCII format via PatentCenter and is hereby incorporated herein by reference in its entirety. Said ASCII copy was created on Jan. 29, 2024 named 077875-720949_Corrected_Sequence_Listing.txt, and is 38,000 bytes in size.

FIELD OF THE INVENTION

The present invention relates generally to C₄ plants having improved agronomic characteristics.

BACKGROUND OF THE INVENTION

Approximately 197 million hectares of maize are planted globally. The total production (~1.1B tons/yr) and yield (90-130 bu/acre globally, over 220 bu/acre with optimal agricultural inputs) is more than any other crop. Along with rice and wheat, maize provides 30% of food calories for more than 4.5 billion people in 94 developing countries. Thus, approximately one-half of the current global population, including a high percentage of subsistence farmers, is dependent on this crop for daily life. However, to achieve high productivity in maize requires intensive agricultural practices not available to small farmers, including the application of significant amounts of nitrogen fertilizer. Nitrogen treatment is a common practice in the US but negatively impacts the environment through fertilizer runoff-based algal blooms and eutrophication of waterways. Therefore, there is a need for plants capable of sustainable agriculture, especially under less than ideal agricultural practices, such as cultivation on marginal land, or where the application of significant amounts of nitrogen fertilizer is not practiced.

SUMMARY OF THE INVENTION

One aspect of the present disclosure encompasses a C₄ plant comprising a genetic disruption of a PEPCK biosynthetic pathway. The plant can exhibit beneficial traits when compared to a wild type plant cultivated under similar growth conditions. The growth conditions can be adverse growth conditions. Adverse growth conditions can be limiting nitrogen conditions, drought conditions, waterlogged conditions, high disease load, high pest load, or combinations thereof. A beneficial trait can be nitrogen use efficiency, drought resistance, resistance to waterlogged conditions, disease resistance, or pest resistance. In some aspects, the improved trait is nitrogen use efficiency.

The plant can exhibit improved agronomic characteristics when compared to a wild type plant cultivated under similar growth conditions, such as under adverse growth conditions. In some aspects, the plant exhibits improved agronomic characteristics under limiting nitrogen conditions. The improved agronomic characteristic can be yield. The yield of the plant can be improved by about 10% or more when compared to a wild type plant cultivated under similar conditions.

The genetic disruption can inhibit the expression of one or more genes encoding an enzyme in the PEPCK biosynthetic pathway. The one or more genes can encode an enzyme selected from carbonic anhydrase (CA), PEP carboxylase (PEPC), PEP Carboxykinase (PEPCK), aspartate aminotransferase (AspAT), alanine aminotransferase (AlaAT), malate dehydrogenase (MDH), NADP-Malic enzyme (NADP-ME), NAD-malic enzyme (NAD-ME), pyruvate phosphate dikinase (PPDK), or combinations thereof. In some aspects, the disruption inhibits the expression of a gene encoding a PEPCK enzyme.

The C₄ plant can be a domesticated plant. Alternatively, the plant can be a wild plant. The plant can be *Zea mays* (maize), sugarcane, sorghum, millets, switchgrass, fonio, or wild or hybrid relatives thereof. In some aspects, the plant is maize. The grain biomass of the maize plant is improved by about 10% or more when compared to a wild type plant cultivated under similar conditions.

When the plant is maize, the disruption can inhibit the expression of one or more genes selected from Table 1. The disruption can inhibit the expression of one or more genes selected from Table 2. In some aspects, the disruption inhibits the expression of the GRMZM2G001696 gene. The disruption can comprise an insertion of a Dissociator (Ds) element at the flanking edge of exon 8 of the gene encoded by the GRMZM2G001696 gene. Alternatively, the disruption can comprise an insertion of a Dissociator (Ds) element in the 3' untranslated region (UTR) of the gene encoded by the GRMZM2G001696 gene. The genetic disruption can comprise a nucleic acid sequence having at least about 75% sequence identity to SEQ ID NO: 1 or SEQ ID NO: 2.

Another aspect of the present disclosure encompasses a maize plant comprising a genetic disruption of a PEPCK biosynthetic pathway, wherein the disruption inhibits the expression of a PEPCK enzyme encoded by the GRMZM2G001696 gene. The genetic disruption can comprise an insertion of a Dissociator (Ds) element at the flanking edge of exon 8 of the gene encoded by the GRMZM2G001696 gene, or an insertion of a Ds element in the 3' untranslated region (UTR) of the gene encoded by the GRMZM2G001696 gene. Further, the genetic disruption can comprise a nucleic acid sequence having at least about 75% sequence identity to SEQ ID NO: 1 or SEQ ID NO: 2.

Yet another aspect of the present disclosure encompasses a maize plant comprising a nucleic acid sequence having at least about 75% sequence identity to SEQ ID NO: 1 or SEQ ID NO: 2.

Another aspect of the present disclosure encompasses a C₄ plant comprising a genetic disruption of the PEPCK biosynthetic pathway, wherein the plant exhibits improved agronomic characteristics under adverse growth conditions. An adverse growth condition can be limiting nitrogen conditions, drought conditions, waterlogged conditions, high disease load, high pest load, or combinations thereof. In one aspect, the adverse growth condition is nitrogen limiting condition. The improved agronomic characteristics can be nitrogen use efficiency, drought resistance, resistance to waterlogged conditions, disease resistance, or pest resistance. An improved agronomic characteristic can be yield.

Another aspect of the present disclosure encompasses a method of improving agronomic characteristics of a $C_4$ plant under adverse growth conditions, by disrupting the PEPCK biosynthetic pathway in the plant. The PEPCK biosynthetic pathway can be disrupted by inhibiting the expression of one or more genes encoding an enzyme selected from CA, PEPC, PEPCK, AspAT, AlaAT, MDH, NADP-ME, NAD-ME, PPDK, or combinations thereof. The PEPCK biosynthetic pathway can be disrupted using transposon-based mutagenesis. The plant can be *Zea mays* (maize). When the plant is maize, the PEPCK biosynthetic pathway can be disrupted by inhibiting the expression of the GRMZM2G001696 gene.

Yet another aspect of the present disclosure encompasses a method of decreasing an amount of nitrogen containing fertilizer required for producing a desirable agronomic characteristic of a $C_4$ plant under limiting nitrogen conditions. The method comprises the steps of (a) obtaining or having obtained a $C_4$ plant comprising a genetic disruption of the PEPCK biosynthetic pathway; (b) cultivating the plant under low nitrogen conditions; and (c) applying an amount of nitrogen-containing fertilizer between planting and harvesting the plant equivalent to no more than 90% of the amount of nitrogen-containing fertilizer applied under the limiting nitrogen conditions, wherein the agronomic characteristics of the plant are the same as when 100% of the amount of nitrogen-containing fertilizer is applied under similar conditions between planting and harvesting the plant. For instance, a plant can be grown under conditions where no nitrogen-containing fertilizer is applied between planting and harvesting the plant. The desirable agronomic characteristic can be yield.

DETAILED DESCRIPTION

Figure 1:
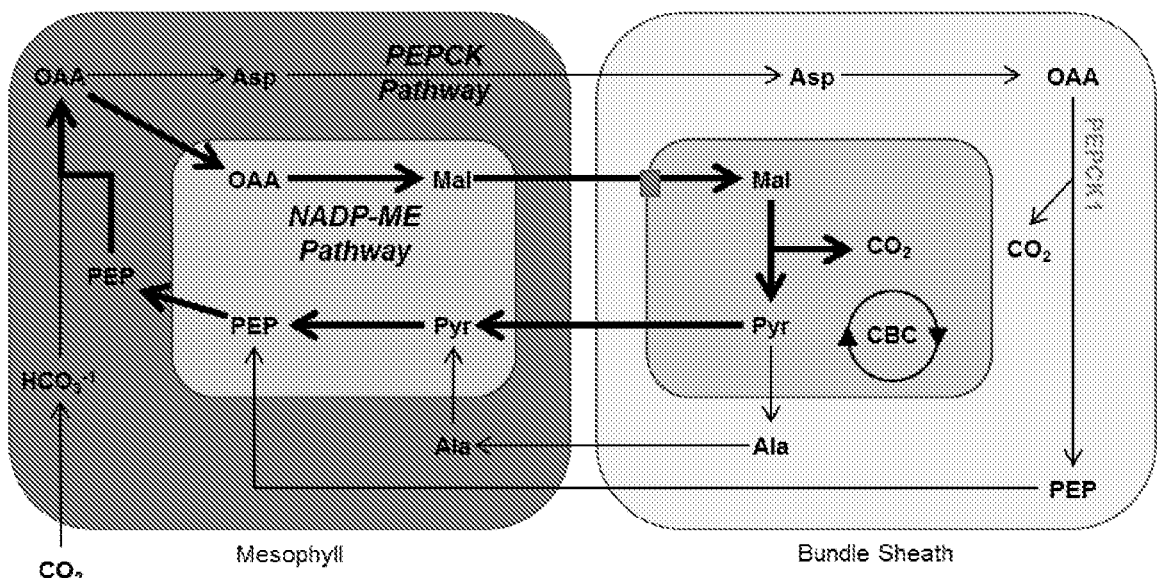
FIG. 1: Schematic of the $C_4$ photosynthetic pathways in maize. Abbreviations: PEPCK: phosphoeno/pyruvate carboxykinase, NADP-ME: NADP-malic enzyme, $CO_2$: carbon dioxide, $HCO_3^{-1}$: bicarbonate, OAA: oxaloacetate, Mal: malate, Asp: aspartate, Pyr: pyruvate, PEP: phosphoeno/pyruvate, Ala: alanine, CBC: Calvin Benson Cycle.

The present disclosure is based in part on the surprising discovery that disrupting the PEPCK pathway in a $C_4$ plant can improve agronomic characteristics of the plant. The plant has improved agronomic characteristics when the plant is cultivated under optimal growth conditions or under adverse growth conditions such as growth on marginal land. For instance, it was discovered that disrupting the PEPCK pathway in a $C_4$ plant improves nitrogen use efficiency of the plant. Such findings have widespread implications for improved efficiency, especially where intensive agricultural practices are not practiced.

I. $C_4$ Plants $C_4$ plants use a 4-carbon compound for photosynthesis to effectively "concentrate" $CO_2$ around the enzyme Ribulose-1,5-bisphosphate carboxylase/oxygenase (RuBisCo or rubisco), which is involved in the first major step of carbon fixation, catalyzing the carboxylation of ribulose-1,5-bisphosphate (RuBP). The result in $C_4$ plants is that RuBisCO is less likely to react with $O_2$. Overall, $C_4$ photosynthesis involves a complicated anatomy that segregates metabolic roles to mesophyll and bundle sheath (BS) cells. Among multiple pathways involved is the phosphoenolpyruvate carboxykinase (PEPCK) pathway in which aspartate is transported to the BS, converted to oxaloacetate using aspartate aminotransferase (AspAT) and decarboxylated by PEPCK.

One aspect of the present disclosure encompasses a $C_4$ plant comprising a genetic disruption of the PEP Carboxykinase (PEPCK) biosynthetic pathway. As such, the plant comprises a genetic disruption of a nuclear, organellar, or extrachromosomal nucleic acid sequence. As described above, it was discovered that a $C_4$ plant comprising a disrupted PEPCK pathway in a $C_4$ plant exhibits beneficial traits associated with improved agronomic characteristics. It was also discovered that the PEPCK pathway can be disrupted with no deleterious effect on the plant.

The PEPCK biosynthetic pathway can be disrupted by inhibiting enzymatic activity of one or more enzymes in the biosynthetic pathway. Methods of inhibiting enzymatic activity are well known in the art and can include the use of small inhibitory molecules, antibodies and antibody fragments, RNA and peptide aptamers, and the like.

The PEPCK pathway can also be disrupted by inhibiting the expression of one or more genes encoding an enzyme in the PEPCK biosynthetic pathway in a $C_4$ plant. As noted above, $C_4$ plants effectively "concentrate" $CO_2$ around rubisco using a 4-carbon compound such that RuBisCO is less likely to react with $O_2$. The complicated photosynthesis process on in $C_4$ plants involves metabolic roles segregated among mesophyll and bundle sheath (BS) cells. During $C_4$ photosynthesis, carbon dioxide diffuses into the mesophyll, and is converted to bicarbonate by carbonic anhydrase (CA). Bicarbonate is then combined with Phosphoenolpyruvate (PEP) by the enzyme Phosphoenolpyruvate carboxylase (PEPC) to produce oxaloacetate, which is then converted to malate or aspartate, the 4-carbon transfer acids partitioned to the BS. Within the BS, three separate decarboxylation reactions release $CO_2$ and generate a 3-carbon molecule (pyruvate or PEP), which is returned to the mesophyll, completing the $C_4$ cycle.

When malate is used as the 4-carbon transfer acid, the decarboxylation by NADP malic enzyme (NADP-ME) occurs in the chloroplast, thereby releasing $CO_2$ around the active site of RuBisCO, and producing pyruvate that is shuttled back to the mesophyll cell. When aspartate is used as the 4-carbon transfer acid, it can be converted to oxaloacetate using aspartate aminotransferase (AspAT), and decarboxylated by PEPCK via the eponymously named PEPCK pathway. The $CO_2$ is released in the cytosol and PEP is recycled to mesophyll cells. In addition, nitrogen transported as a component of aspartate is returned to avoid a nitrogen imbalance. Nitrogen transport can occur by linking the PEPCK pathway with the NADP-ME biosynthetic pathway, to convert the pyruvate produced via the NADP-ME pathway to alanine by alanine aminotransferase (AlaAT), which can then return to the mesophyll carrying the nitrogen. The alanine is converted back to pyruvate in the mesophyll by AlaAT, and pyruvate converted to PEP by pyruvate phosphate dikinase (PPDK) in the mesophyll chloroplast, prior to export to the cytosol as PEP, thus completing the cycle. Another variant on $C_4$, termed the NAD-ME pathway, transfers aspartate by conversion to oxaloacetate occurring in the bundle sheath mitochondria. The OAA is converted to malate by malate dehydrogenase (MDH) and decarboxylated by a mitochondrial NAD-malic enzyme (NAD-ME) to produce NADH, consistent with the NAD-ME acronym. This pathway also relies on shuttling of carbon and nitrogen back to the mesophyll as alanine and interconversions to create PEP that recycles the substrate for $C_4$ fixation.

As such, in addition to the enzymes specific to the PEPCK pathway, the biosynthetic pathway further requires one or more enzymes in the NADP-ME and NAD-ME pathways. Accordingly, the PEPCK pathway can be disrupted by inhibiting the expression of one or more genes encoding an enzyme in the PEPCK pathway and/or an enzyme in the NADP-ME and NAD-ME pathways. The genetic disruption can therefore comprise a disruption of, such as the inhibition of the expression of, one or more genes encoding any of the enzymes CA, PEPC, PEPCK, AspAT, AlaAT, MDH, NADP-ME, NAD-ME, PPDK, or any combination thereof. In some aspects, the genetic disruption inhibits the expression of one or more genes encoding PEPCK, AspA, or AlaAT, or any combination thereof. In one aspect, the expression of a gene encoding the PEPCK enzyme is inhibited.

Each one of the enzymes of the PEPCK pathway can be encoded by one or more genes. For instance, in maize, AlaAT and AspAT can each be expressed in the BS cells and in mesophyll cells. AlaAT of the bundle sheath is encoded by an alanine transferase gene expressed in the mesophyll cells, and another alanine transferase gene is encoded in the bundle sheath cells. Similarly, AspAT of the bundle sheath is encoded by an alanine transferase gene expressed in the mesophyll cells, and another alanine transferase gene expressed in the bundle sheath cells. Accordingly, if an enzyme is encoded by more than one gene, the genetic disruption can inhibit the expression of any one or more genes encoding the enzyme, provided the modification disrupts the PEPCK pathway.

The expression of a gene can be inhibited by introducing one or more mutations into a gene encoding an enzyme of interest. A mutation can inhibit the expression of the gene by disrupting transcription into mRNA and/or splicing and other processing of a precursor of the mRNA to produce the mature mRNA; reducing mRNA stability; translation of the mature mRNA into protein (including codon usage and tRNA availability); glycosylation and/or other modifications of the translation product if required for proper expression and function; or combinations thereof. In some aspects, the expression of a gene is inhibited by introducing one or more mutations that reduce the amount of mRNA expressed by the gene.

Methods of introducing a mutation into a gene are known in the art and include, without limitation, conventional plant breeding methods or by identifying and introducing a naturally occurring variant of a gene, viral infection, bacterial transformation, spontaneous mutation, the use of chemical mutagens, transposon-based mutagenesis, the use of genome editing technologies such as programmable nucleic acid modification systems such as but not limited to CRISPR-based systems, RNA silencing, use of an antisense nucleotide sequence, ribozymes, and the like. The mutation can be in a coding sequence of the gene, or can be in upstream or downstream regions of the gene.

The genetic disruption can inhibit the expression of one or more genes such that the level of mRNA transcribed by the gene is reduced to about 10%, 20%, 30%, 40%, 50%, 60%, 70%, 80%, 90%, or 100% of the level of mRNA when compared to the level of mRNA in a wild type plant. Further, the genetic disruption can inhibit the expression of one or more genes such that the level of protein or enzymatic activity of the protein encoded by the gene is reduced to about 10%, 25%, 50%, 75%, or 100% of the activity of the enzyme when compared to a wild type plant.

Methods of determining the level of mRNA are known in the art. Non-limiting examples of RNA detection methods include reverse transcriptase PCR, reverse transcriptase quantitative PCR, nucleic acid microarrays, hybridization-based methods, branched DNA detection technologies, Northern blotting, and nuclease protection assays. Methods of determining the activity of an enzyme can and will vary depending on the enzyme and the plant, among other factors, and can be determined experimentally. Non-limiting examples of protein detection methods include Western blotting, ELISA assays, and other immunoassays. A decrease in the level of expression may be determined by comparing the levels (of mRNA and/or protein) in a plant with a genetic disruption, to the levels of mRNA and/or protein in a wild type plant.

The plant exhibits beneficial traits under any cultivation conditions when compared to a wild type plant cultivated under similar conditions. Such traits can include improved nitrogen utilization efficiency, improved nitrogen stress tolerance, drought resistance, resistance to waterlogged conditions, disease resistance, pest resistance, or combinations thereof. In some aspects, the plants exhibit beneficial traits under normal growth conditions. For instance, the plants can exhibit improved beneficial traits under intensive modern agricultural growth conditions, greenhouse conditions, hydroponic conditions, and the like. In other aspects, the plants exhibit beneficial traits under adverse growth conditions when compared to a wild type plant cultivated under similar growth conditions. Non-limiting examples of adverse growth conditions include limiting nitrogen conditions, drought conditions, waterlogged conditions, high disease load, elevated salt conditions, high pest load, farming on marginal land, or combinations thereof.

As used herein, the term "limiting nitrogen conditions" indicates that a relatively low level of external nitrogen is available to the plant, e.g., from the growing medium (e.g., soil), water and/or nitrogen fertilizer. The low nitrogen conditions can arise from cultivation in marginal land comprising sub-optimal amounts of nitrogen. The low nitrogen conditions can also arise from the application of a reduced level of nitrogen fertilizer to the plant and/or growing the plant in a low nitrogen medium (e.g., soil, water, and the like). The amount of nitrogen fertilizer available to the plant can be assessed, for example, with respect to a reference value that can be based on any suitable parameter such as, for example, standard agricultural practice (e.g., for that species, variety and/or geographical location) and/or the optimum level of nitrogen fertilizer for plant productivity, the latter optionally taking into consideration adverse effects of providing high levels of nitrogen to the plant such as increased cost and/or detrimental environmental effects. Those skilled in the art will recognize that limiting nitrogen conditions may vary with the plant species, plant variety, nitrogen form, soil type, geographic location, timing, weather, cropping intensity and other parameters that are well within the level of skill in the art.

In some aspects, the plant exhibits improved nitrogen utilization efficiency (NUE). The plant can exhibit improved NUE under nitrogen-limiting conditions or replete (sufficient) nitrogen conditions. NUE refers to a plant's ability to utilize nitrogen in low or high levels of fertilizer. NUE reflects the plant's ability to uptake, assimilate, and/or otherwise utilize nitrogen.

The plants exhibit improved agronomic characteristics under any cultivation conditions when compared to a wild type plant cultivated under similar conditions. Improved agronomic characteristics can include, but are not limited to, greenness, yield, growth rate, biomass, fresh weight, dry weight at maturation, fruit yield, seed yield, seed or plant size, total plant nitrogen content, starch or oil content, fruit nitrogen content, seed nitrogen content, nitrogen content in vegetative tissue, whole plant amino acid content, vegetative tissue free amino acid content, fruit free amino acid content, seed free amino acid content, total plant protein content, fruit protein content, seed protein content, protein content in a vegetative tissue, harvest index, stalk lodging, plant height, ear height and ear length, early seedling vigor, seedling emergence under low temperature stress, or combinations thereof.

In some aspects, the plant exhibits improved yield when compared to a wild type plant cultivated under similar growth conditions. In one aspect, the plant exhibits improved yield under adverse growth conditions, including under nitrogen limiting conditions. The yield of the plant can be improved by about 10%, 20%, 30%, 40%, 50%, 60%, 70%, 80%, 90%, 100% or more when compared to a wild type plant cultivated under similar conditions. In some aspects, disrupting the PEPCK pathway can improve the yield of the plant by about 40%, 45%, 50%, 55%, 60%, 65%, 70%, 75%, or about 80%.

Any $C_4$ plant comprising a PEPCK pathway can be used in the instant disclosure provided the plant expresses a PEPCK pathway. Non-limiting examples of $C_4$ plants comprising a PEPCK pathway include Zea mays (maize), sugarcane, millets, switchgrass, fonio, or wild, domesticated, or hybrid relatives thereof.

In some aspects, the $C_4$ plant is maize. When the plant is maize, the disruption inhibits the expression of one or more genes selected from Table 1. In other aspects, the disruption inhibits the expression of one or more genes selected from Table 2.

In some aspects, the genetic disruption inhibits the expression of the GRMZM2G001696 gene encoding a PEPCK enzyme. When the GRMZM2G001696 gene is mutated, mRNA expression of the gene can be reduced by about 30 to about 70%, or by about 40 to about 60% when compared to the mRNA expression in a wild type plant. Further, when the GRMZM2G001696 gene is mutated, the grain biomass of the plant can be improved by about 10%, 20%, 30%, 40%, 50%, 60%, 70%, 80%, 90%, 100% or more when compared to a wild type plant cultivated under similar conditions.

In one aspect, the disruption comprises an insertion of a Dissociator (Ds) element at the flanking edge of exon 8 of the gene encoded by the GRMZM2G001696 gene. The disruption can comprise a nucleic acid sequence having at least about 75% sequence identity with SEQ ID NO: 1. For instance, the nucleic acid sequence can have about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with SEQ ID NO: 1.

In another aspect, the disruption comprises an insertion of a Ds element in the 3' untranslated region (UTR) of the gene encoded by the GRMZM2G001696 gene. The disruption can comprise a nucleic acid sequence having at least about 75% sequence identity with SEQ ID NO: 2. For instance, the nucleic acid sequence can have about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with SEQ ID NO: 2.

TABLE 1

| Encoded Enzyme | Abbreviation | Gene Model in Zea mays |
| --- | --- | --- |
| Carbonic Anhydrase | CA | large gene family |
| PEP Carboxylase | PEPC | GRMZM2G083841 |
| Aspartate Aminotransferase | AspAT | GRMZM5G836910 |
| Malate Dehydrogenase | MDH | GRMZM2G129513 |
| Aspartate Aminotransferase | AspAT | GRMZM2G094712 |
| PEP Carboxykinase | PEPCK | GRMZM2G001696 |
| Malate Dehydrogenase | MDH | unknown |
| NADP-Malic Enzyme | NADP-ME | GRMZM2G085019 |

TABLE 1-continued

| Encoded Enzyme | Abbreviation | Gene Model in Zea mays |
| --- | --- | --- |
| NAD-Malic Enzyme | NAD-ME | GRMZM2G406672 or GRMZM2G085747 |
| Alanine Aminotransferase | AlaAT | GRMZM5G828630 |
| Alanine Aminotransferase | AlaAT | GRMZM2G120563 |
| Pyruvate, phosphate dikinase | PPDK | GRMZM2G306345 |

TABLE 2

| Encoded Enzyme | Abbreviation | Gene Model in Zea mays |
| --- | --- | --- |
| PEP Carboxykinase | PEPCK | GRMZM2G001696 |
| Aspartate Aminotransferase | AspATm | GRMZM5G836910 |
| Aspartate Aminotransferase | AspATbs | GRMZM2G094712 |
| Alanine Aminotransferase | AlaATbs | GRMZM2G120563 |
| Alanine Aminotransferase | AlaAT | GRMZM5G828630 |

II. Methods

One aspect of the present disclosure encompasses a method of improving agronomic characteristics of a $C_4$ plant under adverse growth conditions. The method comprises disrupting the PEPCK biosynthetic pathway in the plant, thereby generating a plant having improved agronomic characteristics. The PEPCK biosynthetic pathway is disrupted by inhibiting the expression of one or more genes expressing an enzyme in the PEPCK biosynthetic pathway, an enzyme in a pathway associated with the PEPCK pathway, or combinations thereof. In one aspect, the mutation is introduced using transposon-based mutagenesis. The $C_4$ plants, the agronomic characteristics, the biosynthetic pathways, and the enzymes of the biosynthetic pathways are described above in Section I.

Another aspect of the present disclosure encompasses a method of decreasing an amount of nitrogen-containing fertilizer required for producing agronomic characteristics of a $C_4$ plant under limiting nitrogen conditions. The method comprises the steps of (a) obtaining or having obtained a $C_4$ plant comprising a genetic disruption of the PEPCK biosynthetic pathway; (b) cultivating the plant under low nitrogen conditions; and (c) applying an amount of nitrogen-containing fertilizer between planting and harvesting the plant equivalent to no more than 90% of the amount of nitrogen-containing fertilizer applied under the low nitrogen conditions. Under such conditions, the agronomic characteristics of the plant are the same as when 100% of the amount of nitrogen-containing fertilizer is applied under similar conditions between planting and harvesting the plant. The $C_4$ plant, the agronomic characteristics, the biosynthetic pathways, and the enzymes of the biosynthetic pathways are described above in Section I. In some aspects, the desirable characteristic is yield.

The amount of nitrogen-containing fertilizer applied between planting and harvesting the plant can be equivalent to no more than about 80%, 70%, 60%, 50%, 40%, 30%, 20%, 10%, or less of the amount of nitrogen-containing fertilizer applied under the low nitrogen conditions. In some aspects, no nitrogen-containing fertilizer is applied between planting and harvesting the plant.

Fertilizers and exogenous nitrogen of the present disclosure may comprise one or more of the following nitrogen-containing molecules: ammonium, nitrate, nitrite, ammonia, glutamine, etc. Nitrogen sources of the present disclosure may include anhydrous ammonia, ammonia sulfate, urea, diammonium phosphate, urea-form, monoammonium phosphate, ammonium nitrate, nitrogen solutions, calcium nitrate, potassium nitrate, sodium nitrate, and the like.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above-described cells and methods without departing from the scope of the invention, it is intended that all matter contained in the above description and in the examples given below, shall be interpreted as illustrative and not in a limiting sense.

The term "comprising" means "including, but not necessarily limited to;" it specifically indicates open-ended inclusion or membership in a so-described combination, group, series and the like. The terms "comprising" and "including" as used herein are inclusive and/or open-ended and do not exclude additional, unrecited elements or method processes. The term "consisting essentially of" is more limiting than "comprising" but not as restrictive as "consisting of." Specifically, the term "consisting essentially of" limits membership to the specified materials or steps and those that do not materially affect the essential characteristics of the claimed invention.

"Nitrogen limiting conditions" refers to conditions where the amount of total available nitrogen (e.g., from nitrates, ammonia, or other known sources of nitrogen) is not sufficient to sustain optimal plant growth and development. One skilled in the art would recognize conditions where total available nitrogen is sufficient (replete nitrogen conditions) to sustain optimal plant growth and development. One skilled in the art would recognize what constitutes sufficient amounts of total available nitrogen, and what constitutes soils, media and fertilizer inputs for providing nitrogen to plants. Nitrogen-limiting conditions will vary depending upon a number of factors, including but not limited to, the particular plant and environmental conditions.

The terms "nitrogen stress tolerance," "low nitrogen tolerance" and "nitrogen deficiency tolerance" are used interchangeably herein, which indicate a trait of a plant and refer to the ability of the plant to survive under nitrogen limiting conditions or low nitrogen conditions.

As used herein, "expression" includes but is not limited to one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "wild type" refers to a plant from which a genetically plant modified plant is derived.

As used herein, the term "gene" means a segment of DNA that contains all the information for the regulated biosynthesis of an RNA product, including promoters, exons, introns, and other untranslated regions that control expression.

The term "sequence identity" refers to nucleic acid sequences, refers to sequences having at least about 75% sequence identity. Thus, the upstream and downstream sequences in the donor polynucleotide may have about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with sequences upstream or downstream to the nucleic acid locus sequence. In specific aspects, the upstream and downstream sequences in the donor polynucleotide may have about 95% or 100% sequence identity with nucleic acid sequences upstream or downstream of the nucleic acid locus targeted by the targeting endonuclease.

As used herein, the term "plant" includes reference to whole plants, plant organs, plant tissues, seeds and plant cells, and progeny of same. Plant cells include, without limitation, cells from seeds, suspension cultures, embryos, meristematic regions, callus tissue, leaves, roots, shoots, gametophytes, sporophytes, pollen, and microspores.

"Drought" refers to a decrease in water availability to a plant that, especially when prolonged or when occurring during critical growth periods, can cause damage to the plant or prevent its successful growth (e.g., limiting plant growth or seed yield).

"Drought tolerance" reflects a plant's ability to survive under drought without exhibiting substantial physiological or physical deterioration, and/or its ability to recover when water is restored following a period of drought.

The terms "genome modification" and "genome editing" refer to processes by which a specific nucleic acid sequence in a genome is changed such that the nucleic acid sequence is modified. The nucleic acid sequence may be modified to comprise an insertion of at least one nucleotide, a deletion of at least one nucleotide, and/or a substitution of at least one nucleotide. The modified nucleic acid sequence is inactivated such that no product is made. Alternatively, the nucleic acid sequence may be modified such that an altered product is made.

As used herein, the term "encode" is understood to have its plain and ordinary meaning as used in the biological fields, i.e., specifying a biological sequence. The term "encode," when used to describe the function of nucleic acid molecules, customarily means to identify one single amino acid sequence that makes up a unique polypeptide, or one nucleic acid sequence that makes up a unique RNA. That function is implemented by the particular nucleotide sequence of each nucleic acid molecule.

The terms "nucleic acid" and "polynucleotide" refer to a deoxyribonucleotide or ribonucleotide polymer, in linear or circular conformation. For the purposes of the present disclosure, these terms are not to be construed as limiting with respect to the length of a polymer. The terms may encompass known analogs of natural nucleotides, as well as nucleotides that are modified in the base, sugar and/or phosphate moieties. In general, an analog of a particular nucleotide has the same base-pairing specificity, i.e., an analog of A will base-pair with T. The nucleotides of a nucleic acid or polynucleotide may be linked by phosphodiester, phosphothioate, phosphoramidite, phosphorodiamidate bonds, or combinations thereof.

The term "nucleotide" refers to deoxyribonucleotides or ribonucleotides. The nucleotides may be standard nucleotides (i.e., adenosine, guanosine, cytidine, thymidine, and uridine) or nucleotide analogs. A nucleotide analog refers to a nucleotide having a modified purine or pyrimidine base or a modified ribose moiety. A nucleotide analog may be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos.

The terms "polypeptide" and "protein" are used interchangeably to refer to a polymer of amino acid residues, and can be any polypeptide comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in voluminous research literature.

The terms "upstream" and "downstream" refer to locations in a nucleic acid sequence relative to a fixed position. Upstream refers to the region that is 5' (i.e., near the 5' end of the strand) to the position, and downstream refers to the region that is 3' (i.e., near the 3' end of the strand) to the position.

The terms "genome modification" and "genome editing" refer to processes by which a specific nucleic acid sequence in a genome is changed such that the nucleic acid sequence is modified. The nucleic acid sequence may be modified to comprise an insertion of at least one nucleotide, a deletion of at least one nucleotide, and/or a substitution of at least one nucleotide. The modified nucleic acid sequence is inactivated such that no product is made. Alternatively, the nucleic acid sequence may be modified such that an altered product is made.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences may also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) may be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981).

This algorithm may be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP may be used using the following default parameters: genetic code=standard; filter=none; strand=both; cut-off=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs may be found on the GenBank website.

EXAMPLES

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

The publications discussed throughout are provided solely for their disclosure before the filing date of the present application. Nothing herein is to be construed as an admission that the invention is not entitled to antedate such disclosure by virtue of prior invention.

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Introduction for Examples 1 to 67

Approximately 500 million acres of maize are planted globally, resulting in 1.1 billion tons of grain per year. The average yield per acre globally is 90-130 bushels, but when agricultural inputs such as nitrogen are optimal, productivity can exceed 220 bushels per acre and far exceed other crops (Stat, 2018). This difference emphasizes the key role of nitrogen in the process. Unfortunately, fertilizer N is a major expense, energetically costly to make, and not equally accessible for all farmers, particularly in developing countries. Leaching and runoff of N from the soil negatively impacts the environment through groundwater contamination and algal blooms and eutrophication of waterways (Diaz and Rosenberg, 2008). Therefore, improved germplasm that enhances nitrogen use efficiency would have positive economic and ecological effects.

Contributing to the enhanced productivity of maize is the use of $C_4$ photosynthesis. $C_4$ photosynthesis has independently evolved at least 60 times in plants to concentrate carbon dioxide around the active site of Rubisco, effectively limiting the oxygenation reaction of ribulose 1,5-bisphosphate (RuBP) and suppressing photorespiration and improving carbon assimilation (Hatch and Slack, 1966; Sage et al., 2011). Equally crucial, the $C_4$ pathway reduces the concentration of photosynthetic enzymes required by the leaf and can result in greater nitrogen use efficiency per unit of leaf area compared to $C_3$ plants (Brown, 1978). With few exceptions (Edwards et al., 2004), $C_4$ photosynthesis entails a complicated anatomy that segregates metabolic roles to mesophyll and bundle sheath (BS) cells. In the mesophyll, carbon dioxide is converted to bicarbonate and combines with phosphoenolpyruvate (PEP) to generate oxaloacetate, which is then converted to either malate or aspartate, which serve as transfer acids and diffuse into the bundle sheath. In the bundle sheath, one or more of three decarboxylation reactions—by NADP-malic enzyme (NADP-ME), NAD-malic enzyme (NAD-ME) or phosphoenolpyruvate carboxykinase (PEPCK)—release $CO_2$ and generate a 3-carbon molecule (pyruvate or PEP) that is returned to the mesophyll, completing the $C_4$ cycle (FIG. 1). When aspartate is used as the transfer acid, it moves an amino group between the mesophyll and bundle sheath. To avoid an imbalance of nitrogen between the two cell types, alanine, generated from pyruvate and an ammonium group, shuttles nitrogen back to the mesophyll, as described by gene expression analysis and isotopic labeling (Gowik et al., 2011; Pick et al., 2011; Covshoff et al., 2016; Weissmann et al., 2016). Historically, plants have been classified into $C_4$ subtypes based on the decarboxylation enzyme—NADP-ME, NAD-ME, or PEPCK—used in the bundle sheath (Hatch et al., 1975); however, recent studies suggest that the pathways can operate in tandem (Wang et al., 2014; Weissmann et al., 2016; Schlüter et al., 2018). Maize plants use the NADP-ME pathway with PEPCK participating as a minor decarboxylase (i.e., 10-25%; (Weissmann et al., 2016; Arrivault et al., 2017)). Initial labeling experiments indicated that radiolabel from $CO_2$ was passed to malate, as expected for the NADP-ME pathway, but also to aspartate, which was not canonically part of the pathway (Chapman and Hatch, 1979). Transcript, protein, and activity of PEPCK provided support for PEPCK as an additional $C_4$ decarboxylase in maize (Walker et al., 1997; Furumoto et al., 1999; Wingler et al., 1999). Maintaining both malic enzyme and PEPCK pathways could create more flexible use of ATP and NADPH, which could be important in varied light environments (Furbank, 2011), and would decrease the size of the metabolite pools and gradients of the transfer acids necessary between the two cell types (Wang et al., 2014).

Nitrogen is involved in other aspects of photosynthesis in addition to the PEPCK pathway. Plants require large amounts of nitrogen to produce the photosynthetic apparatus, and Rubisco, PPDK, and PEPC proteins alone comprise approximately one half of leaf protein. The amounts of these enzymes are highly dependent on the nitrogen status of the plant (Avdeeva and Andreeva, 1973; Sugiharto et al, 1990) and impact the rate of photosynthesis, when light is not limiting (Matsuoka et al., 2001). $C_4$ plants have improved nitrogen use efficiency (NUE) relative to $C_3$ species, though substantial variation for NUE exists between $C_4$ subtypes, due to variation in Rubisco characteristics. Reduction in the amount of Rubisco to maintain high levels of photosynthesis results in NADP-ME and PEPCK subtypes that are more nitrogen use efficient than NAD-ME in the grasses (Taub and Lerdau, 2000; Ghannoum et al., 2005; Pinto et al., 2014; Pinto et al., 2016), and additional nitrogen can be partitioned to the thylakoid in the leaf or to other plant tissues (Ghannoum et al., 2005). Compared to the NADP-ME pathway operating in isolation, the PEPCK pathway shuttles amino acids and shares enzymes with nitrogen metabolism that directly link carbon and nitrogen metabolism in the leaf (Majeran et al., 2005). Though multiple pathways require a greater investment in soluble proteins, more cross-talk results between photosynthesis and the other reactions involved in plant metabolism. Aspartate, for example, is tied to N assimilation, protein synthesis, and the TCA cycle in addition to $C_4$-PEPCK photosynthesis (reviewed in Lea et al, 1996; (Galili, 2011)), and is key to the improved nitrogen use efficiency in a subset of NADP-ME species that do not use aspartate for the $C_4$ shuttle (Majeran et al., 2005; Bräutigam and Gowik, 2016).

Tandem operation of NADP-ME and PEPCK pathways in maize provides an opportunity to further address questions on the impact of $C_4$ subtype on NUE. During N limitation, maize plants reduce aspartate $C_4$ shuttling but maintain malate flux, thus relying more heavily on the NADP-ME pathway for photosynthesis. The majority of the aspartate pool is available to participate in other roles in the leaf (Khamis et al., 1992), including the plant response to environmental stress that results in altered nitrogen homeostasis. The importance of nitrogen status to plant growth and photosynthesis (Sinclair et al., 2019) is sometimes overlooked, but is clear from enzyme biosynthetic requirements and linked metabolite pools that are involved in both nitrogen assimilation and photosynthetic processes.

Without wishing to be bound by any one theory, the inventors hypothesized that the tandem operation of PEPCK and NADP-ME pathways in maize may not be optimized for current agricultural practices. PEPCK decarboxylation capacity was knocked down through a transposon-based mutagenesis approach using a two-step transposition screen to select transposon insertion events from a donor Dissociator element originally located 600 kb away. The results surprisingly indicate that normal operation of this pathway in the field limits grain yield; in nitrogen-limiting conditions, the non-mutant PEPCK pathway negatively impacted grain yield by up to 40% based on independent field trials in four consecutive years. Decreased PEPCK pathway activity, confirmed by RNAseq and enzymatic assays, led to accumulation of aspartate in the leaf and a trend toward lower maximal rates of $CO_2$ assimilation, particularly under stress conditions. Based on RNAseq and stable isotope labeling, the NADP-ME pathway did not appear to compensate for lost PEPCK activity. Despite a slightly lower $CO_2$ assimilation rate, pepck1::Ds plants accumulated vegetative biomass at a level similar to non-mutant controls. It is possible that the additional aspartate allowed increased metabolism in pathways that would otherwise be limiting growth. Thus, opportunities for enhanced productivity of maize on marginal land could result from limiting PEPCK and more carefully considering N in photosynthesis; such plants could improve the efficiency of agriculture by making better use of marginal land to generate food, feed, and fuel.

Example 1. Ds Reverse Genetic Screening

Figure 2A:
FIG. 2A. Location of the Ds transposon in the two pepck::Ds alleles. pepck1-1::Ds is located at the junction of intron 7 and exon 8; pepck1-2::Ds is in the 3'UTR.
Figure 2B:
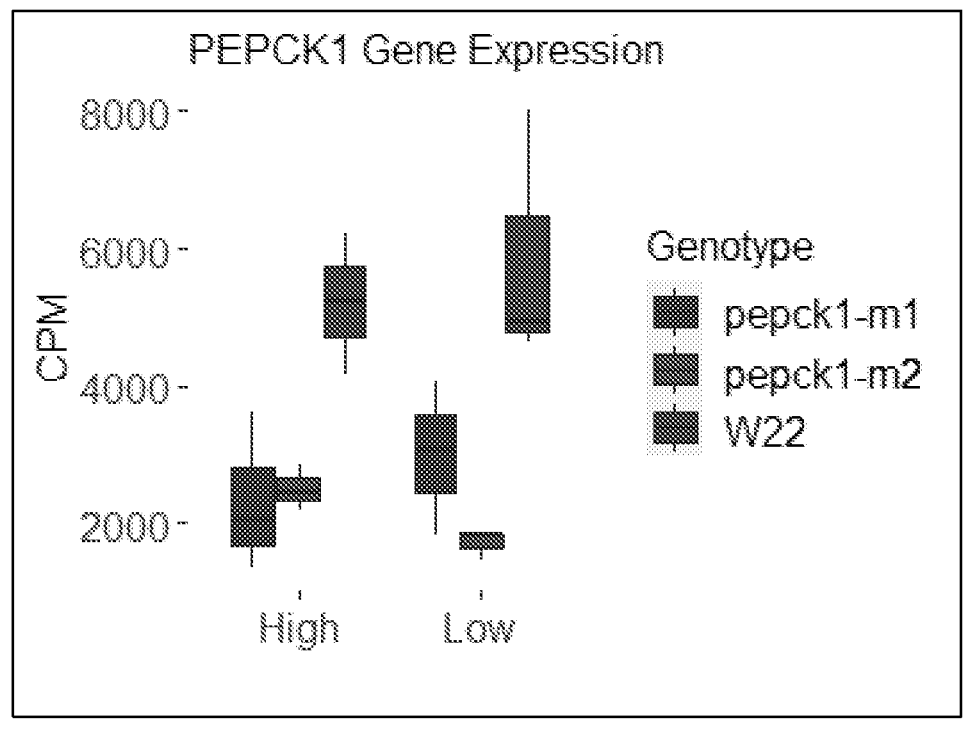
FIG. 2B. Box plot showing gene expression decreased in both alleles by two-fold relative to wild-type.
Figure 2C:
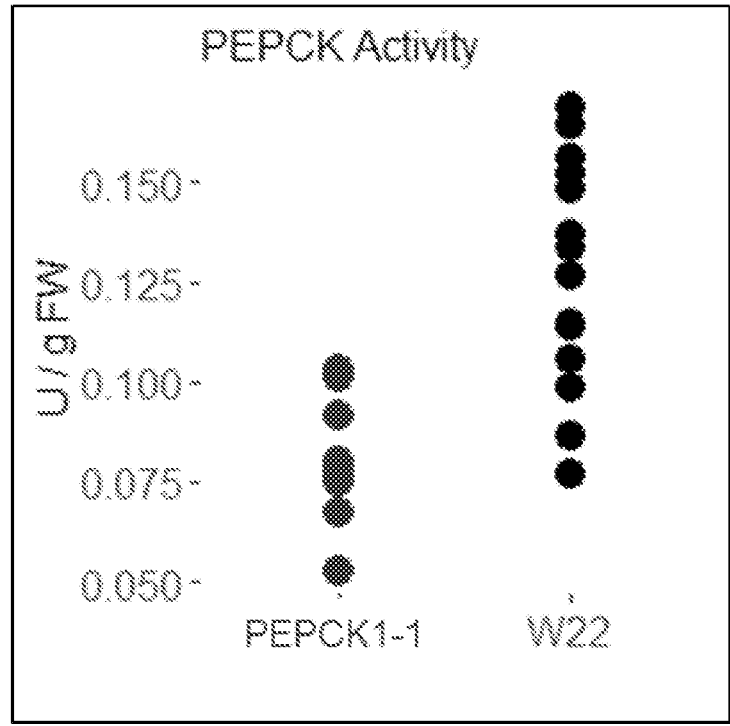
FIG. 2C. Plot showing PEPCK Enzyme activity.

In order to test the effect of the PEPCK pathway on maize plants, a stable mutant in the maize phosphoenolpyruvate carboxykinase1 (PEPCK1) gene (GRMZM2G001696; Zm00004b001002) was generated using Ac/Ds transposon-mediated mutagenesis system (Ahern et al., 2009). Because of the distance between PEPCK1 and the donor Ds element, located 600 kb from PEPCK1, a two-step screen was used. In the first screen, four of the genes located in the intervening sequence between PEPCK1 and the donor Ds were assayed for insertions along with PEPCK1. No insertions were recovered in PEPCK1 gene; however, a single insertion allele was recovered in one of the intervening genes (Zm00004b001002) located 460 kb away from the donor Ds. This new insertion allele was then used to generate a second population from which two insertion alleles were identified in PEPCK1. The location of the insertion alleles was determined by sequencing. The first allele is located at the intron7-exon8 junction, and the second allele within the 3'UTR. Using quantitative RT-PCR, both alleles were found to have a two-fold decrease in expression compared to W22 controls (FIG. 2B), indicating a knock-down of gene expression.

Figure 3A:
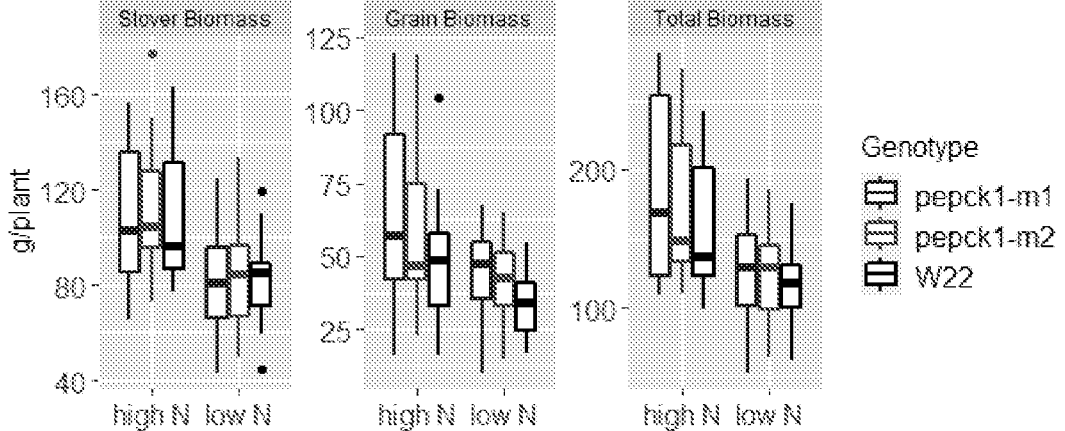
FIG. 3A. Boxplots showing the phenotypic response of the mutant in a nitrogen responsive field site over three years. Boxplots represent distribution of phenotypes representing five individual plants sampled from the same plot in the nitrogen response field. First boxes in each set represent the pepck1-1::Ds allele, second boxes in each set represent the pepck1-2::Ds, and third boxes in each set represent the W22 controls. Average of all three years for stover biomass, grain biomass and total biomass at high and low N are shown.
Figure 4:
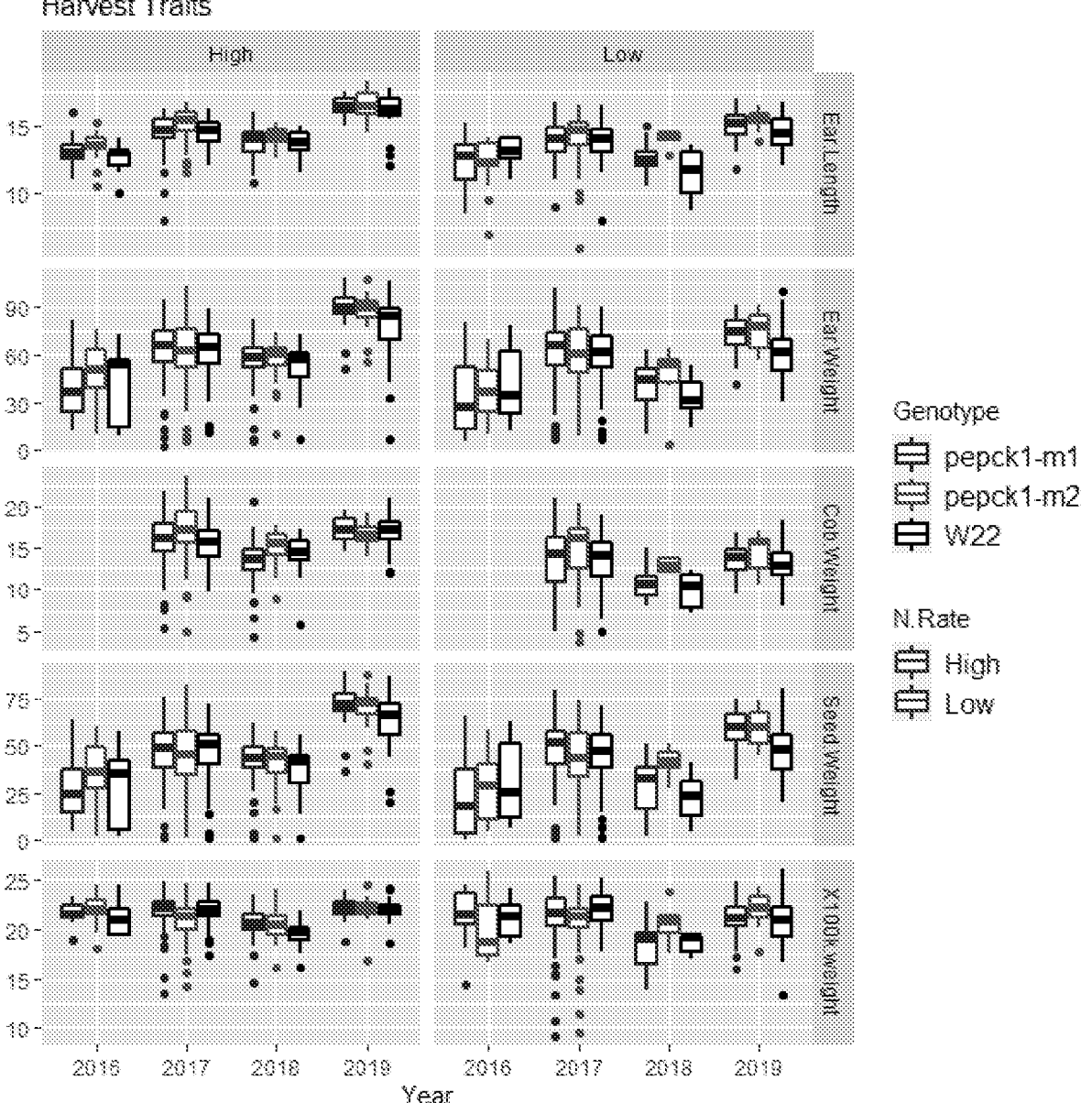
FIG. 4. Box plots showing measures of additional agronomic traits of mutant alleles and wild type plants.

Example 2. Grain Biomass Increased in pepck1::Ds Plants in a Nitrogen Response Field The effect of the mutation on productivity was tested by growing the plants in a nitrogen response field. Biomass and yield component traits were measured on the mutant plants grown in the nitrogen response field. For each plot, stover, grain, and total biomass were measured and a subsample of the stover and grain were collected to determine nitrogen (N) concentration in the plant. From these measurements, harvest index and nitrogen use efficiency traits were calculated. Grain biomass was higher in both alleles of pepck1:: Ds compared to W22 control plants (FIG. 3A, C). W22 had an average grain biomass of 49.6 grams per plant when grown at high N and 33.7 g/plant at low N. The pepck1::Ds lines averaged 67.2 and 59.9 g/plant at high N and at low N averaged 44.5 and 40.7 g/plant. The increased grain biomass was attributed to increased ear size and small increases in kernel weight (FIG. 4). Stover traits and total biomass were similar between pepck1::Ds and W22 plants when averaging the results over the four field seasons (FIG. 3A). Nitrogen content was also measured and correlated strongly with biomass data ($r^2$=0.99 for grain, 0.88 for stover, and 0.97 total plant). Thus, harvest index and nitrogen use efficiency improved because the increase in grain biomass and total grain N were not accompanied by increased vegetative biomass at maturity and may possibly indicate improved nutrient remobilization.

Figure 3B:
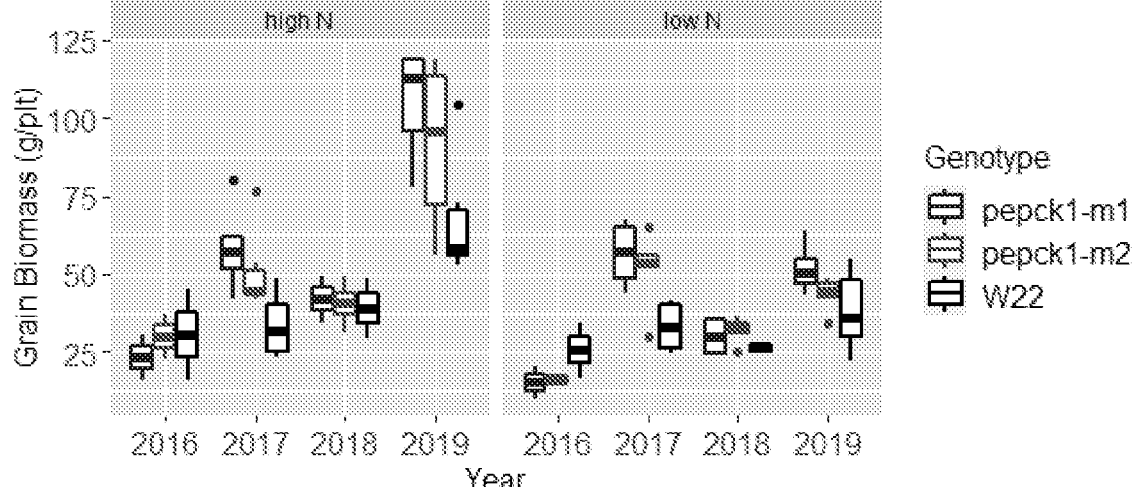
FIG. 3B. Boxplots showing the phenotypic response of the mutant in a nitrogen responsive field site over three years. Boxplots represent distribution of phenotypes representing five individual plants sampled from the same plot in the nitrogen response field. First boxes in each set represent the pepck1-1::Ds allele, second boxes in each set represent the pepck1-2::Ds, and third boxes in each set represent the W22 controls. Grain biomass measurements for each year at high or low N are shown.
Figure 3C:
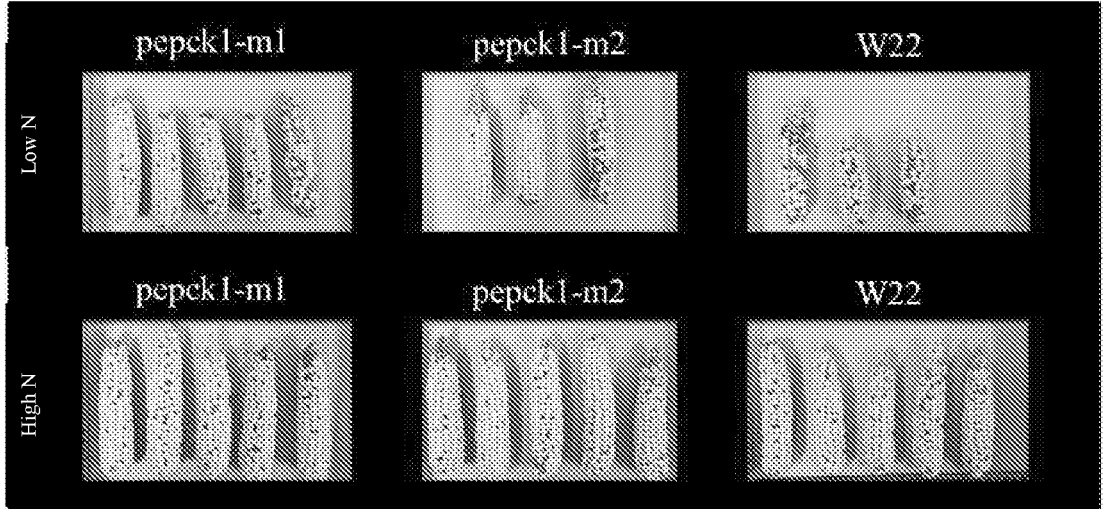
FIG. 3C. Photographs showing representative ears from pepck1::Ds and W22 control plants grown at high and low N.

Over 3 years of filed studies, grain biomass in both pepck1::Ds mutant alleles increased in the combined year data and trended larger than W22 in three of four field seasons (FIG. 3B; see also nitrogen response in FIG. 3B). The amount of nitrogen response in the field also varied between years, with the largest nitrogen response in 2019 (FIG. 3B; Supplemental Data S1). Although the year effect was strong, grain biomass in both pepck1::Ds mutant alleles increased in the combined year data and trended larger than W22 in three of four field seasons.

Figure 5A:
FIG. 5A. Photograph showing height of representative plants grown in a greenhouse p55 days after sowing at high and low N.
Figure 5B:
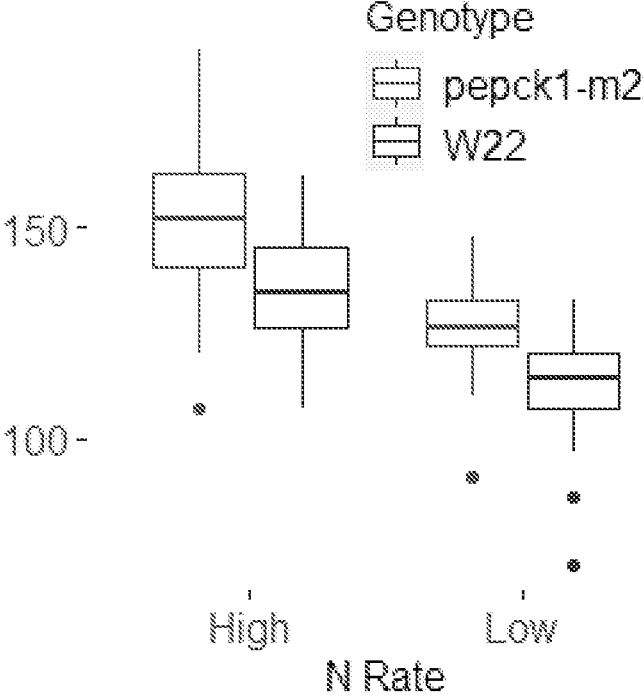
FIG. 5B. Boxplot showing height of plants grown in a greenhouse 55 days after sowing at high N. pepck1::Ds plants were 16.1 cm taller (p<1e-5, Student's t-test), at low N, plants were 14.0 cm taller (p<1e-7, Student's t-test).

Example 3. Vegetative Traits Were Enhanced in Greenhouse Grown pepck1::Ds Plants In addition to field phenotypic responses, the pepck1::Ds mutants were characterized in a controlled growth environment. Agronomic traits were measured in greenhouse grown plants at the V16 growth stage after limiting or replete nitrogen conditions for 55 days as described in the methods. The pepck1::Ds plants (only allele pepck1-2:Ds) were taller than the W22 controls in both N treatments (p<0.0001, Student's t-test; FIG. 5). Stem diameter was also measured but was not significantly different between the genotypes, and plants grown in replete N had larger stem diameters than plants grown in limiting N for both genotypes. Overall, the phenotypic trend of increased vegetative biomass in the pepck1::Ds plants was observed in the greenhouse as well as in field conditions.

Figure 6A:
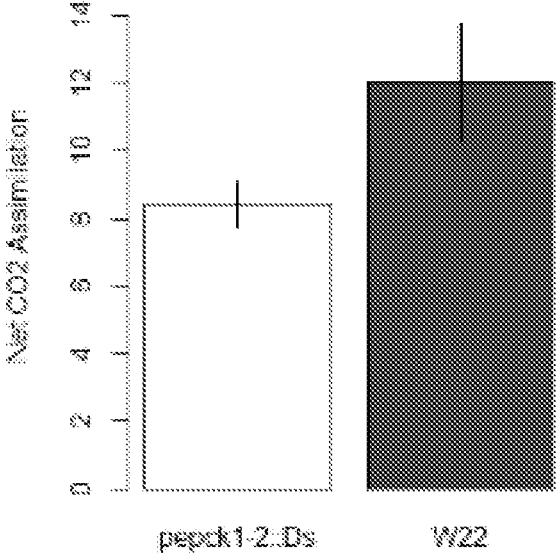
FIG. 6A. Gas exchange in pepck1::Ds and W22 control plants measured net $CO_2$ assimilation ($A_{net}$). Plants were grown to 8 days after pollination in normal fertilization and gas exchange was measured 20 cm from the tip of leaf 13, which subtends the ear.
Figure 6B:
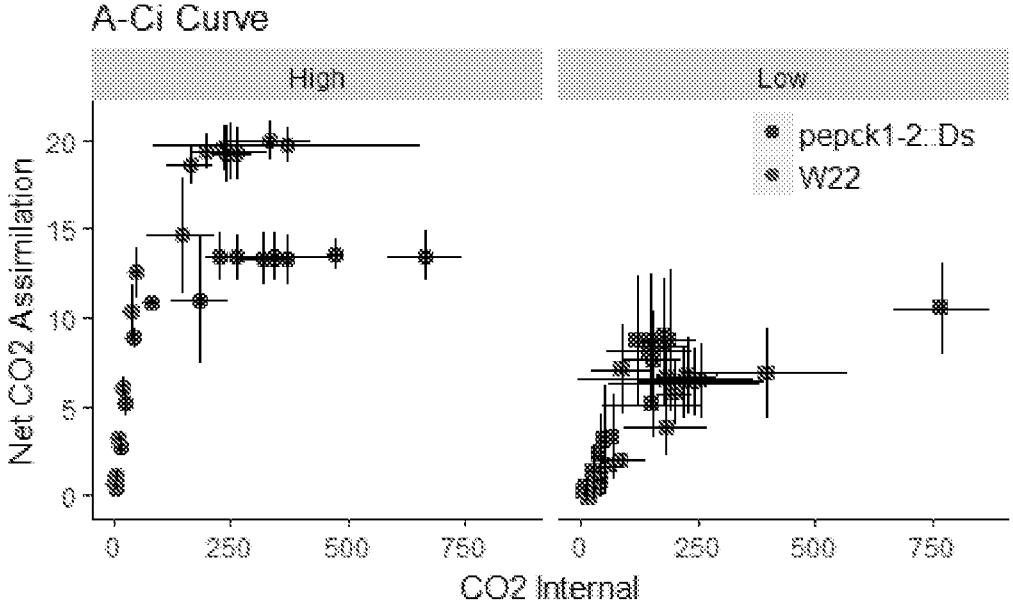
FIG. 6B. Gas exchange in pepck1::Ds and W22 control plants measured net $CO_2$ assimilation ($A_{net}$). Plants were grown under high or low nitrogen conditions for 30 days and gas exchange was measured on the top collared leaf using a LI-6800.
Figure 6C:
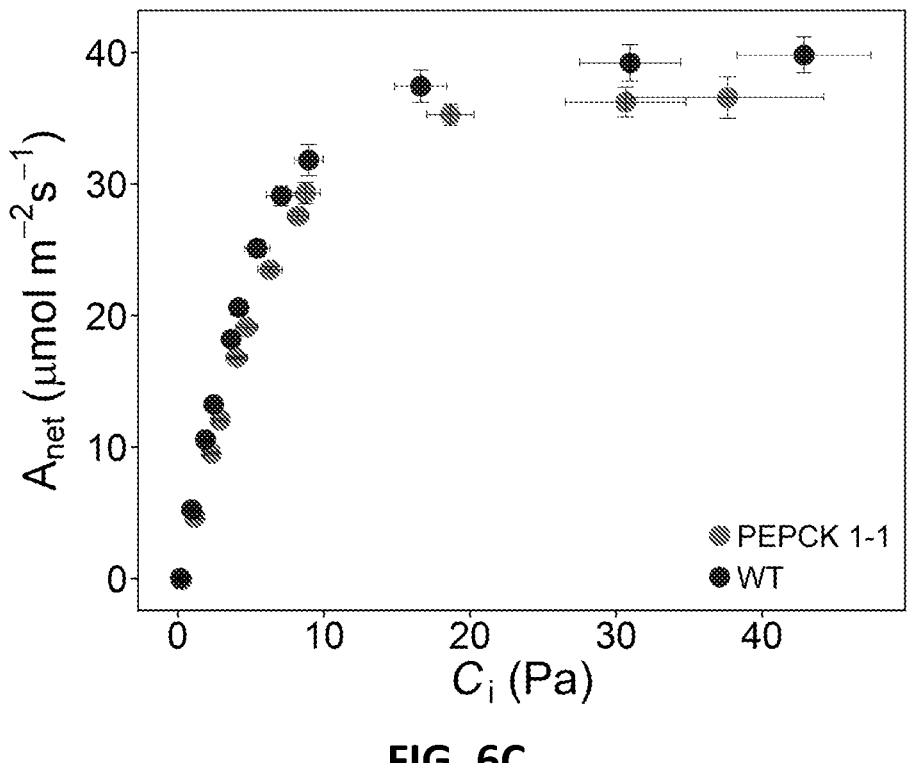
FIG. 6C. Gas exchange in pepck1::Ds and W22 control plants measured net $CO_2$ assimilation ($A_{net}$). Plants were grown for 30 days in Pullman, WA, and $A_{net}$ in response to increased $CO_2$ was measured FIG. 6D. Gas exchange in pepck1::Ds and W22 control plants measured net $CO_2$ assimilation ($A_{net}$). $^{13}$C discrimination in pepck1::Ds1 and W22 plants were measured under a gradient of stable light conditions.
Figure 6D:
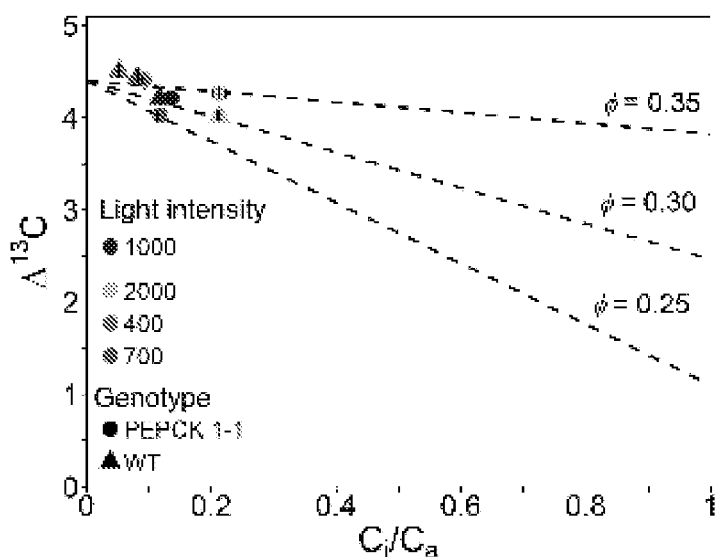
FIG. 6E. Gas exchange in pepck1::Ds and W22 control plants measured net $CO_2$ assimilation ($A_{net}$). Enzyme activity for phosphoenolpyruvate carboxylase (PEPC) and Rubisco were measured in pepck1::Ds1 and W22
FIG. 6F. Gas exchange in pepck1::Ds and W22 control plants measured net $CO_2$ assimilation ($A_{net}$). $A_{net}$ was measured in fluctuating light environments. Leaves were acclimated to high light (1500 μmol photons m$^{-2}$ s$^{-1}$), then they were exposed to alternating high and low light (250 μmol photons m$^{-2}$ s$^{-1}$) intensities in the following intervals: 1500, 250, and 1500 for ten minutes each then a series of fourteen one-minute intervals of low and high light intensities. Mutant plants had a dampened response to high light after short intervals of low light, and the response was exacerbated after repeated shading events.

Example 4. Photosynthetic Measurements Did not Indicate Carbon is Limiting Growth Photosynthetic traits were measured in the pepck1::Ds mutants under multiple conditions to determine environments where multiple $C_4$ pathways may contribute. Net $CO_2$ assimilation ($A_{net}$) was measured using a gas exchange instrument (LI-6800, LI-Cor Inc, Lincoln NE). The thirteenth leaf (leaf subtending the ear) was measured on four individual plants eight days after pollination (approximately 65 days after sowing). During plant growth, lower leaves receive fluctuating light due to shading from upper leaves, and eventually undergo remobilization and senescence, resulting in reduced photosynthetic capacity relative to young leaves. $A_{net}$ in pepck1::Ds and W22 plants was much lower than for younger plants (12.0 $\mu$mol m$^{-2}$ s$^{-1}$) in the leaves at 65 days after sowing and 27% lower (8.4 $\mu$mol m$^{-2}$ s$^{-1}$; p=0.019, Student's t-test) for pepck1::Ds than W22 in greenhouse plants (FIG. 6A). In younger plants (25 days after sowing) grown hydroponically with replete (15 mM) nitrogen, $A_{net}$ was also 30% lower in pepck1::Ds than W22 (p<0.0001, Student's t-test). However, when limited nitrogen (1.5 mM) was provided, $A_{net}$ dropped to approximately 5.0 $\mu$mol m$^{-2}$ s$^{-1}$, and the difference between mutant and W22 was not statistically significant (p=0.57, Student's t-test; FIG. 6B, 6C). In high N, the initial slope of the $CO_2$ response curve decreased and the maximum $A_{net}$ in pepck1:: Ds trended lower but was not statistically different than W22 (FIG. 6D). The general effect was that pepck1::Ds mutants trended toward decreased $A_{net}$ compared to W22.

Figure 6E:
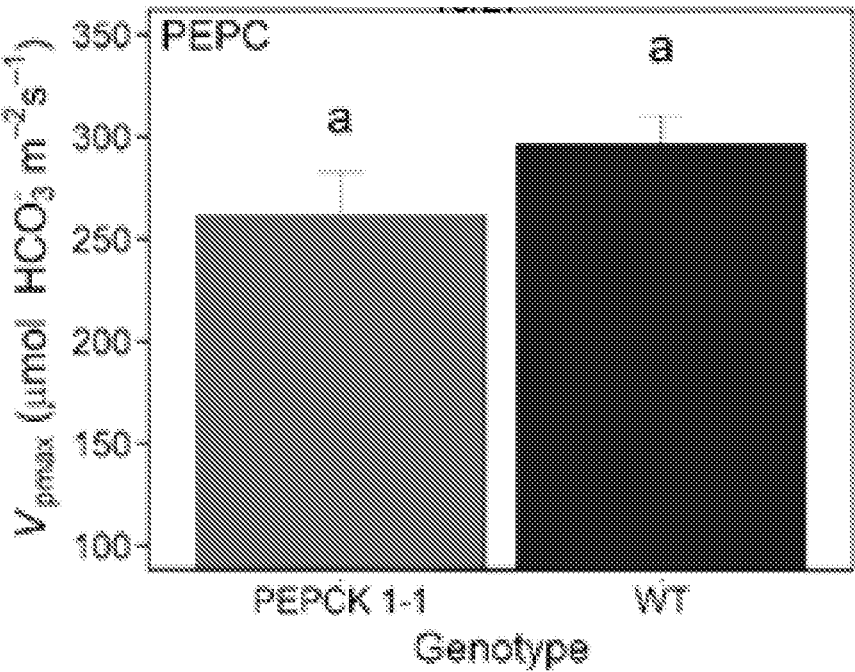
Figure 6E:
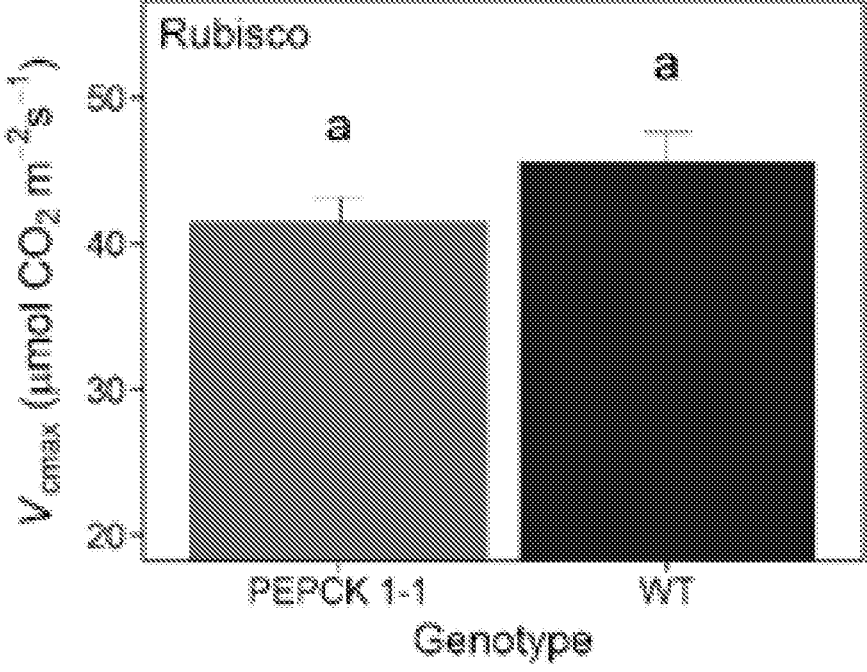

Changes in $A_{net}$ could not explain the enhanced biomass production in the field; therefore, we examined the coordination of $C_4$ shuttle and CBC activities. Maize plants typically operate a combination of two pathways that shuttle $CO_2$ into bundle sheath cells, and without the flux through the PEPCK pathway, the bundle sheath concentration of $CO_2$ could be decreased, and CBC activity concordantly decreased. The carboxylation reactions (PEPC and Rubisco) decreased modestly, qualitatively consistent with changes in net assimilation rate, though changes in bundle sheath leakiness (Farquhar, 1983; Von Caemmerer, 2000) were not observed when $\Delta^{13}C$ measurements were made (FIG. 6D to FIG. 6E).

Figure 6F:
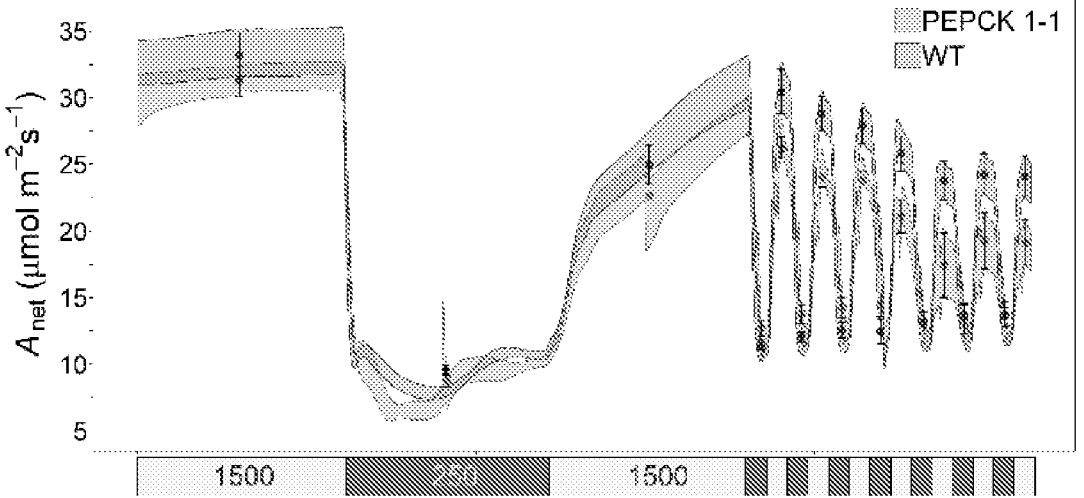
Figure 7A:
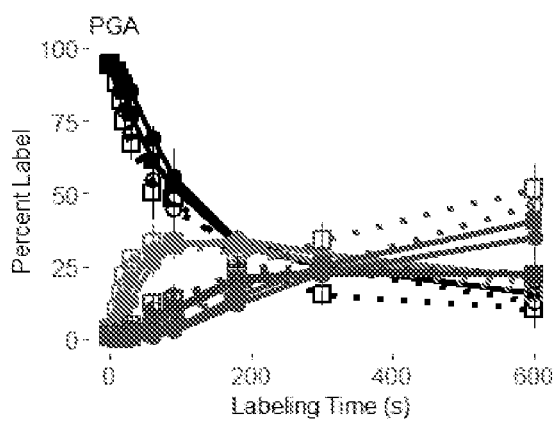
FIG. 7A. Graph showing isotope labeling results over time of PGA, PEP, and pyruvate.
Figure 7A:
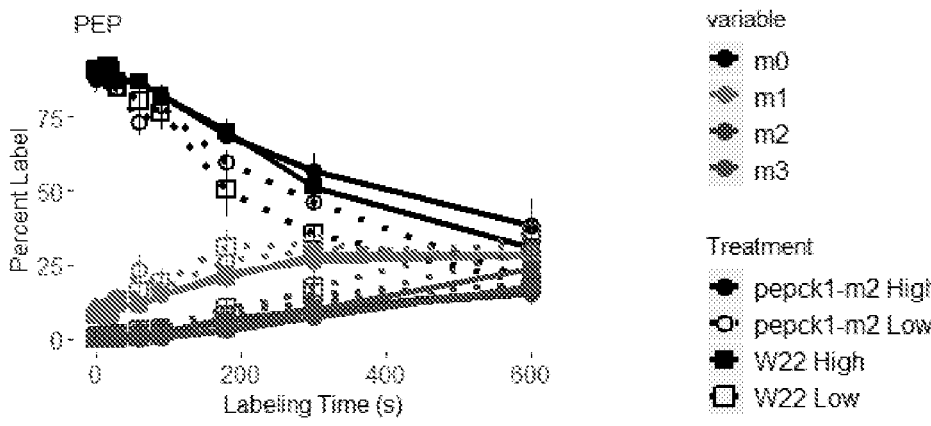
Figure 7A:
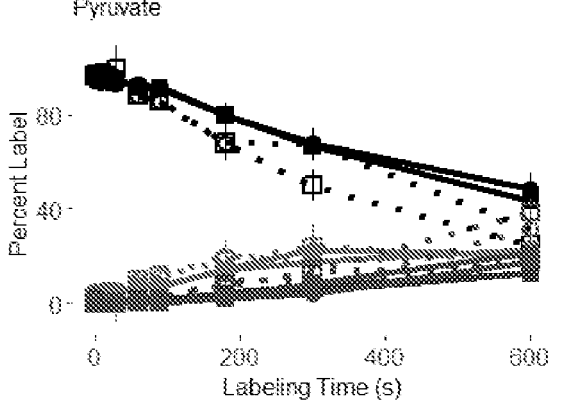
Figure 7B:
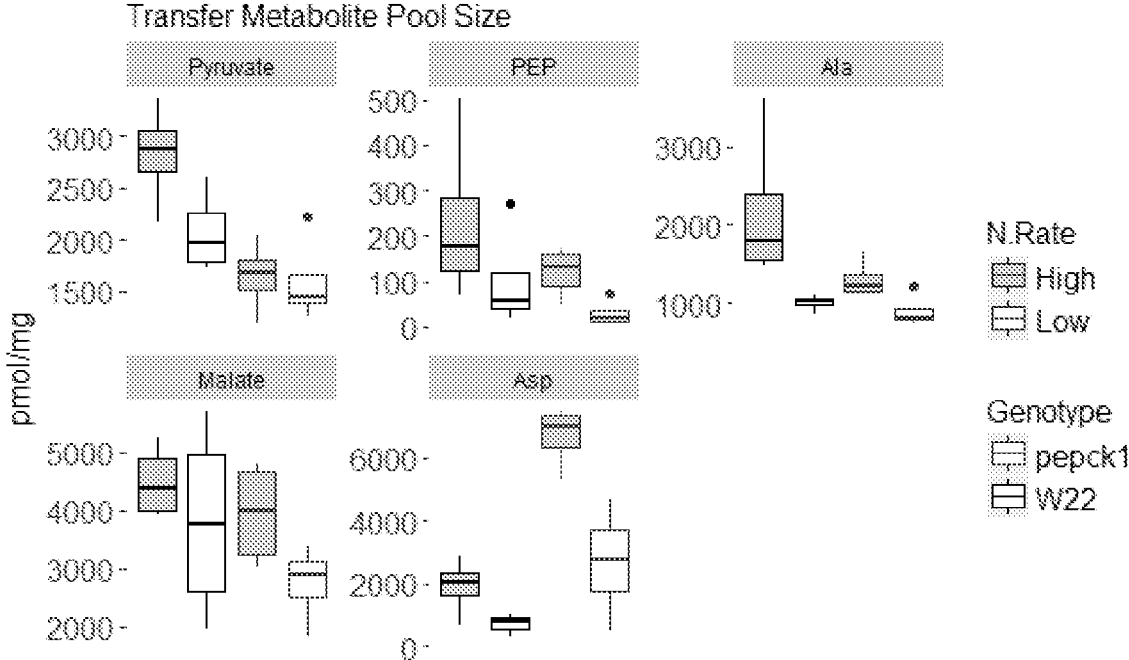
FIG. 7B. Box plots showing total pool sizes for pyruvate, PEP, alanine, malate, and aspartate.

Another possibility is that the PEPCK pathway may complement the NADP-ME pathway by improving energy homeostasis between mesophyll and bundle sheath cells (Furbank, 2011). To test this hypothesis in the fluctuating light experiment, pepck1::Ds plants were subjected to short intervals of high and low light intensity. In the first 10-minute intervals at 1500 and 250 $\mu$E PAR, $A_{net}$ was not different between W22 and pepck1::Ds plants, but in the next 10-minute period at 1500 $\mu$E, pepck1::Ds plants had significantly lower $A_{net}$ and remained lower in all of the following one-minute intervals at 1500 $\mu$mol photons m$^{-2}$ s$^{-1}$. However, $A_{net}$ did not differ between genotypes at any of the intervals at 250 $\mu$mol photons m$^{-2}$ s$^{-1}$. The pepck1::Ds plants exhibited a dampening response in successive intervals, with lower rates of $CO_2$ assimilation and an increasing difference from W22 with additional shading periods (FIG. 6F).

Together, these experiments demonstrate that under a controlled provision of carbon and replete nitrogen, carbon limitations and metabolite and energy balancing were not responsible for the altered plant growth. In the mutant, $C_4$ shuttle and CBC metabolism remained linked, such that when the PEPCK pathway was diminished, photosynthetic $CO_2$ assimilation decreased commensurately. The mutant effect was most noticeable in stress conditions such as growing in the lower part of the canopy or after repeated light fluctuations (FIG. 6A, FIG. 6F), consistent with the role for tandem NADP-ME and PEPCK pathway operation. In addition, photosynthetic output in both the mutant and W22 control were highly nitrogen responsive (FIG. 6B), indicating a potential point of control between plant nitrogen status and photosynthetic output.

Example 5. Metabolic Changes in $C_4$ and Calvin Benson Cycle were Consistent with Restricted Decarboxylation by PEPCK Stable isotope labeling was performed to describe differences in the metabolism of the transfer acids for the NADP-ME and PEPCK pathways. Synthetic air containing $^{13}CO_2$ (400-410 ppm) was provided in planta to maize leaves through a custom built small labeling chamber (~40 mL volume) for various time intervals to determine the degree of labeling in malate (NADP-ME), aspartate (PEPCK), and other intermediates involved in $C_4$ and $C_3$ photosynthesis. Because the reactions occur quickly and with few metabolic steps between initial carboxylation of $CO_2$ by PEPC and label incorporation, $^{13}C$ was rapidly incorporated into malate and aspartate, with appreciable measurements of singly labeled molecules within ten seconds, the shortest time point. Malate and aspartate share a precursor, oxaloacetate, and thus the labeling patterns would be expected to be similar. At short time intervals, both malate and aspartate were singly labeled, consistent with $^{13}C$ label from $^{13}CO_2$ incorporating at the C-4 position and the established biochemistry of the decarboxylation reaction where the carbon in the C-4 position is subsequently released in the bundle sheath cells (FIG. 6). Additional $^{13}C$ label, e.g. in the C1-C3 position, was incorporated into malate and aspartate at a slower rate from the conversion of precursors labeled in the CBC (FIG. 6). CBC intermediates were more slowly labeled than malate and aspartate, consistent with known pathways and labeling descriptions (Weissmann et al., 2016; Arrivault et al., 2017). For example, the amount of singly labeled 3-PGA rapidly increased after 15-20 seconds (FIG. 7).

Figure 8:
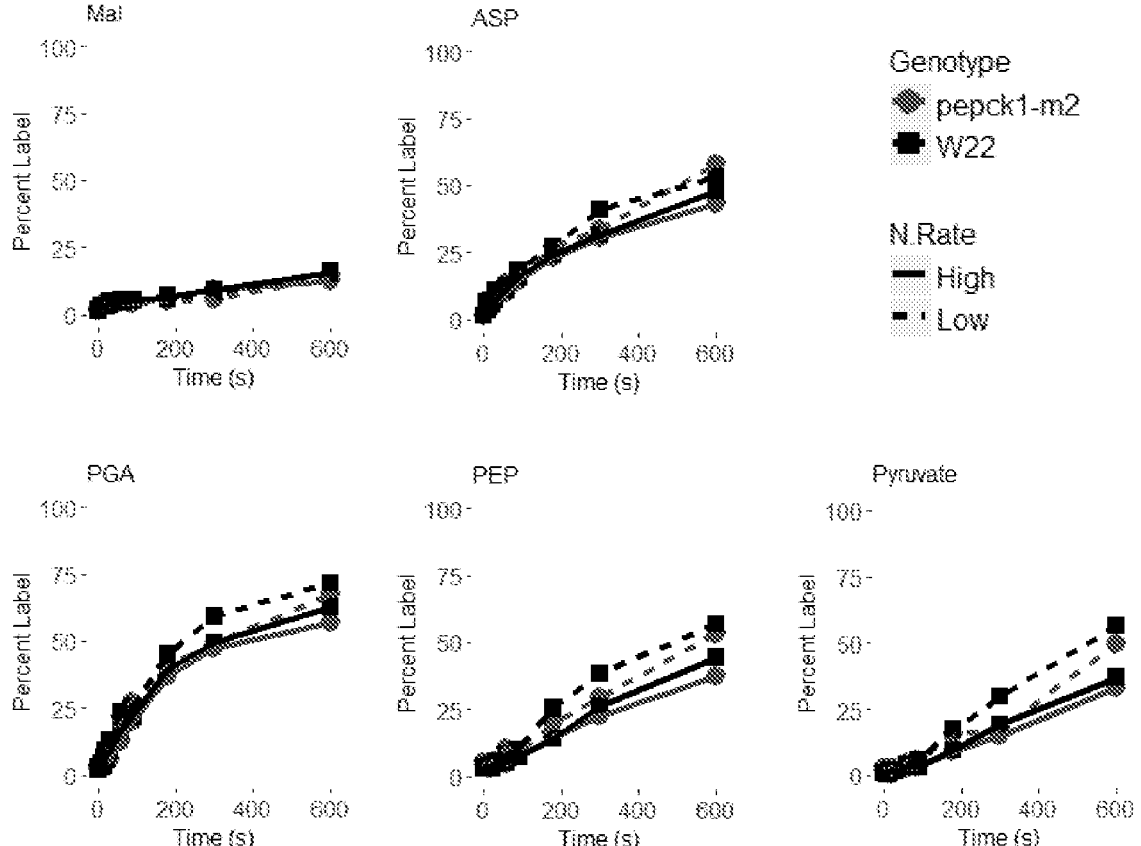
FIG. 8. Graphs showing average labeling curves for all measured metabolites.
Figure 9A:
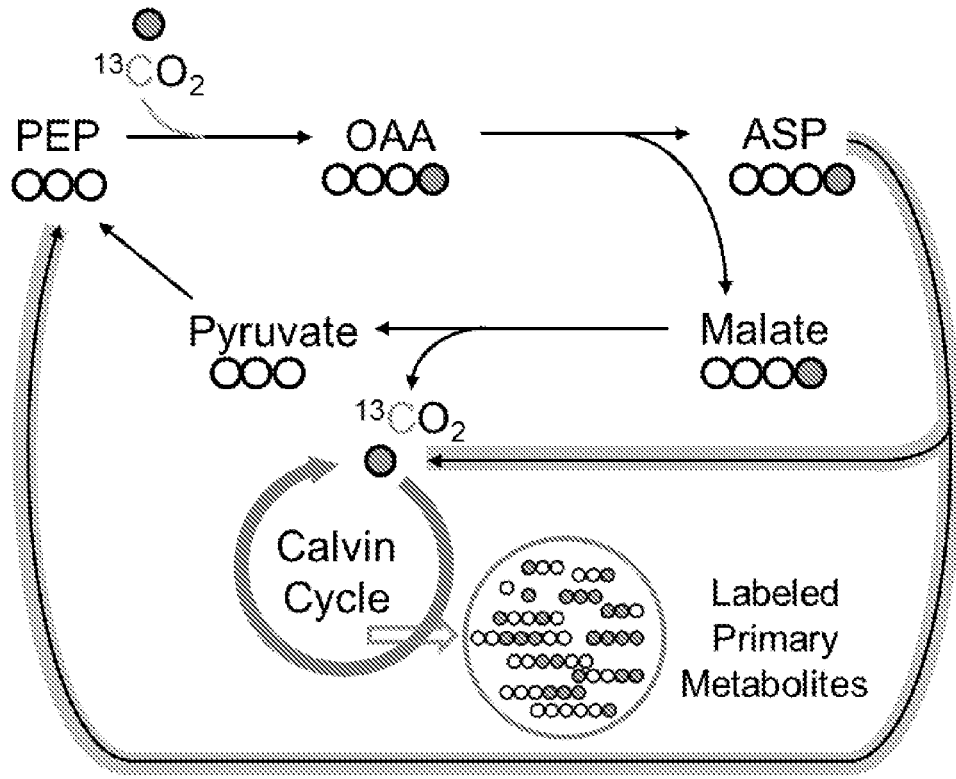
FIG. 9A. Diagrammatic representation of CO2 carboxylation in the mesophyll.
Figure 9B:
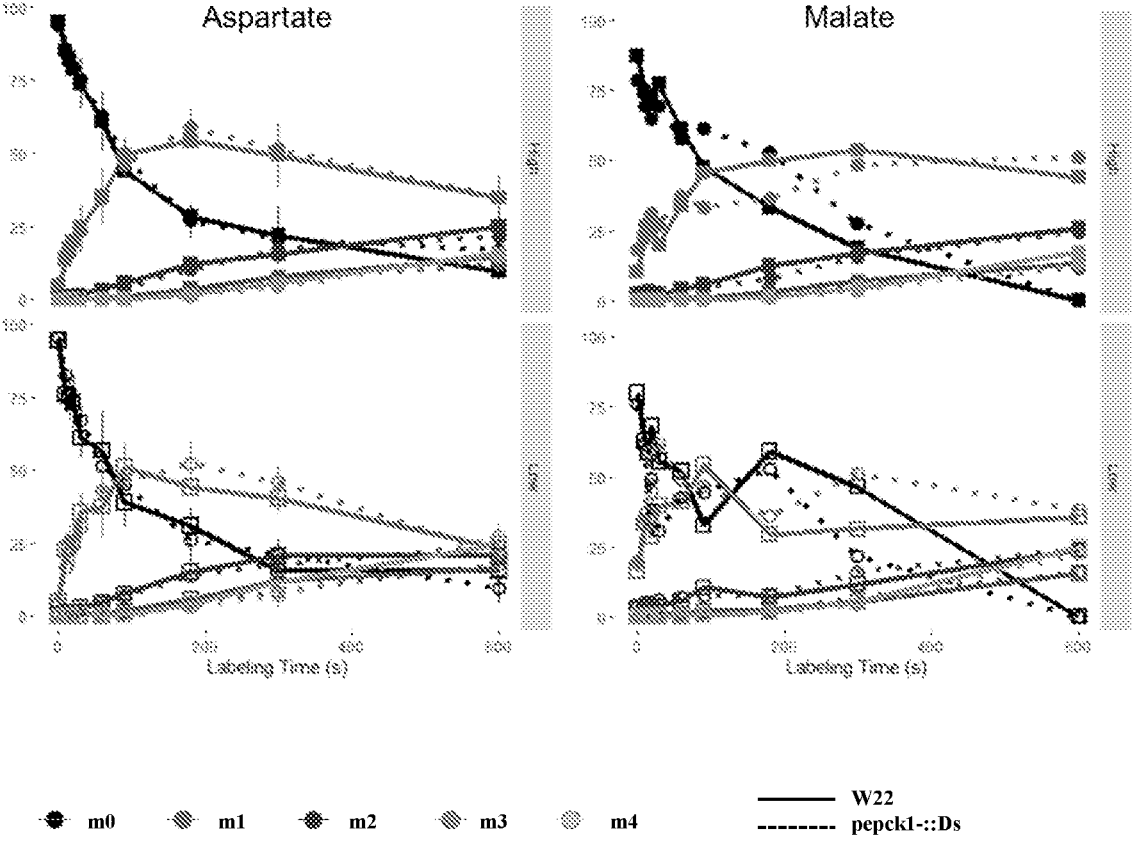
FIG. 9B. Graphs showing aspartate and malate levels over time during $^{13}CO_2$ labeling diagrammed in FIG. 9A. Pool size measurements reveal normal $CO_2$ carboxylation in the mesophyll, but an accumulation of the PEPCK pathway transfer acid aspartate, likely due to decreased decarboxylation in the bundle sheath by PEPCK.
Figure 9C:
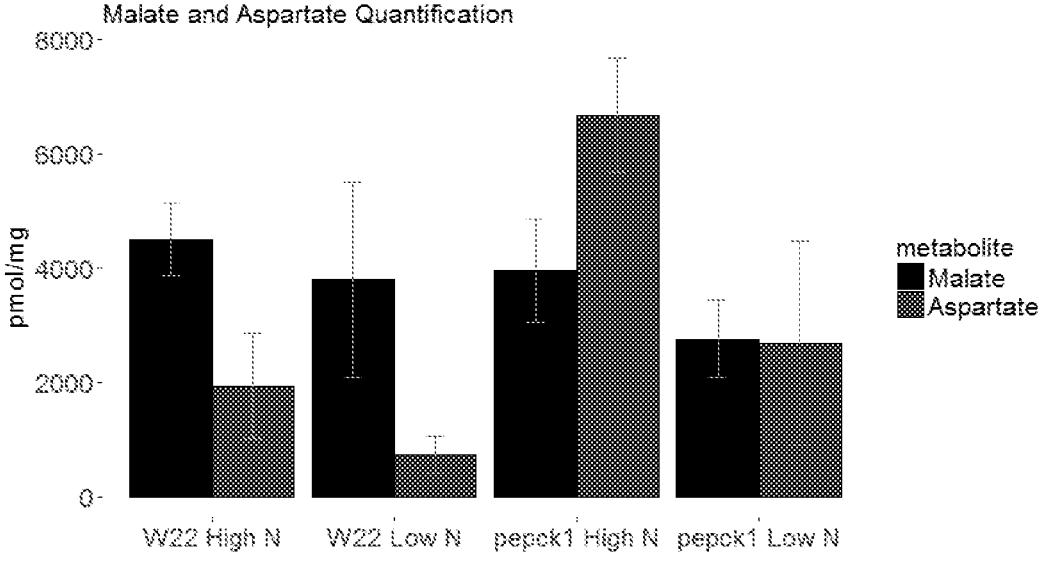
FIG. 9C. Plot showing aspartate and malate levels during $^{13}CO_2$ labeling diagrammed in FIG. 9A. Pool size measurements reveal normal $CO_2$ carboxylation in the mesophyll, but an accumulation of the PEPCK pathway transfer acid aspartate, likely due to decreased decarboxylation in the bundle sheath by PEPCK.

Malate and aspartate pools differ in size and participation in the PEPCK and NADP-ME pathways, which must be accounted for to assess $C_4$ metabolism. Similar to other reports (Weissmann et al., 2016; Arrivault et al., 2017), malate labeling in this experiment was incomplete, indicating a large inactive pool of malate in the maize leaf that does not participate in photosynthesis. After ten minutes of labeling, over 70% of the malate pool remained unlabeled and 12-15% of all carbons were labeled (FIG. 8). No other metabolite quantified was shown to have a large inactive pool, for example, the aspartate pool became 90% labeled within the same time period. The active pool of malate was calculated by correcting for the unlabeled portion from the longest time point for each of the four genotype-by-nitrogen treatments (i.e. pepck1::Ds at either high or low N and W22 at either high or low N). The unlabeled fraction, $M_0$, from a label-saturated time point was subtracted from malate $M_0$ isotopologues for each time point and then the remaining $M_0$ rescaled with other isotopologues to estimate the active $C_4$ malate pool. Ten minutes of labeling with $^{13}CO_2$ is sufficient to approximate the active pool of malate in maize leaves as the labeling levels do not change further from 10 to 60 min (Arrivault et al., 2017). After correcting for the active pool of malate, its labeling pattern was similar to that observed in aspartate; however the pool size of aspartate was 3-fold greater in pepck1::Ds suggesting that the reduced PEPCK activity was resulting in a backup of aspartate accumulation. The size of the aspartate pool was also highly responsive to N, though malate was not (FIG. 9C). At high N, aspartate accumulated to 6000 nmol $g^{-1}$ FW, which was 1.5× larger than the 4000 nmol $g^{-1}$ FW of malate in the pepck1::Ds line; however even in low N, the aspartate pool accumulated to nearly 2500 nmol $g^{-1}$ FW, equal to the pool size of malate in pepck1::Ds. Variation in malate was more limited though malate decreased ~25% under low N conditions in the pepck1::Ds line.

Figure 9D:
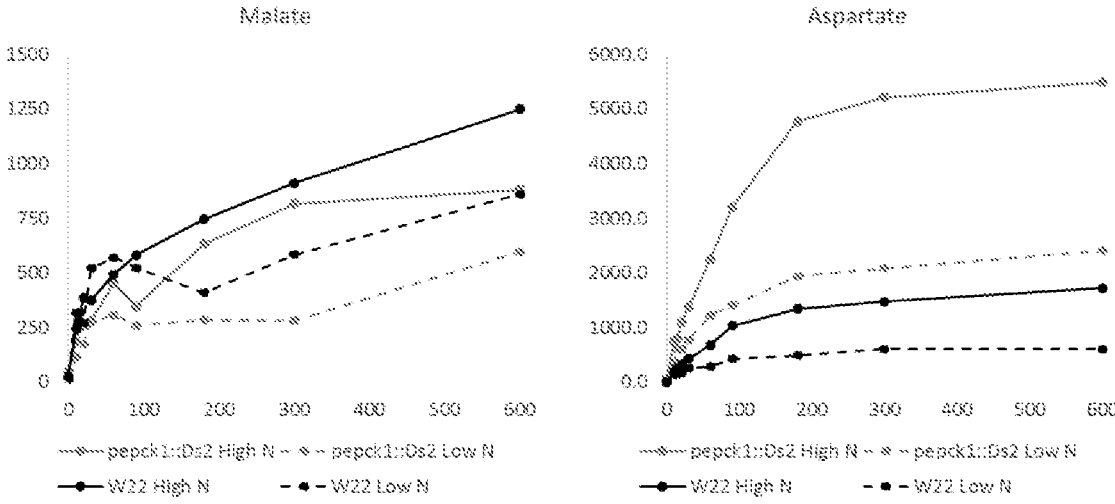
FIG. 9D. Graphs showing aspartate and malate levels during $^{13}CO_2$ labeling diagrammed in FIG. 9A. Pool size measurements reveal normal $CO_2$ carboxylation in the mesophyll, but an accumulation of the PEPCK pathway transfer acid aspartate, likely due to decreased decarboxylation in the bundle sheath by PEPCK.

Based on the pool size and $^{13}C$ isotopologues distributions, $^{13}C$ atom equivalents were calculated by weighting each isotopologues amount by the number of carbons and summing for each time point using the method of Arrivault et al., 2016 to quantify the rate of carbon labeling differences within a metabolite between W22 control and pepck1::Ds plants (FIG. 9D). At high N, the pepck1::Ds line had 4.6-fold faster labeling in aspartate than malate during the first 20s of labeling, while W22 labeled in malate and aspartate at equal rates (0.9-fold). The trend was the same in low N, with aspartate labeling 5.7 times faster in pepck1::Ds and 1.6 times faster in W22 (FIG. 9D). However the $^{13}C$ accumulation in CBC intermediates (FIG. 7A) and their pool sizes (FIG. 7B) were greater in W22. The smaller pool size for alanine in pepck1::Ds plants is also consistent with decreased PEPCK pathway, as the transfer of amino N in the form of aspartate to the BS would otherwise need to be returned to the mesophyll by an alanine shuttle. Alanine accounted for 6.9 and 8.6% of all amino acids in the mutant at high and low N, whereas in W22 the levels were higher, 13.4 and 11.9% respectively. With decreased CBB metabolite pool sizes and decreased $C_4$ shuttle metabolite pools in the pepck1::Ds mutant, the large pool of aspartate likely reflects metabolism not specific to the $C_4$ shuttle.

Figure 10:
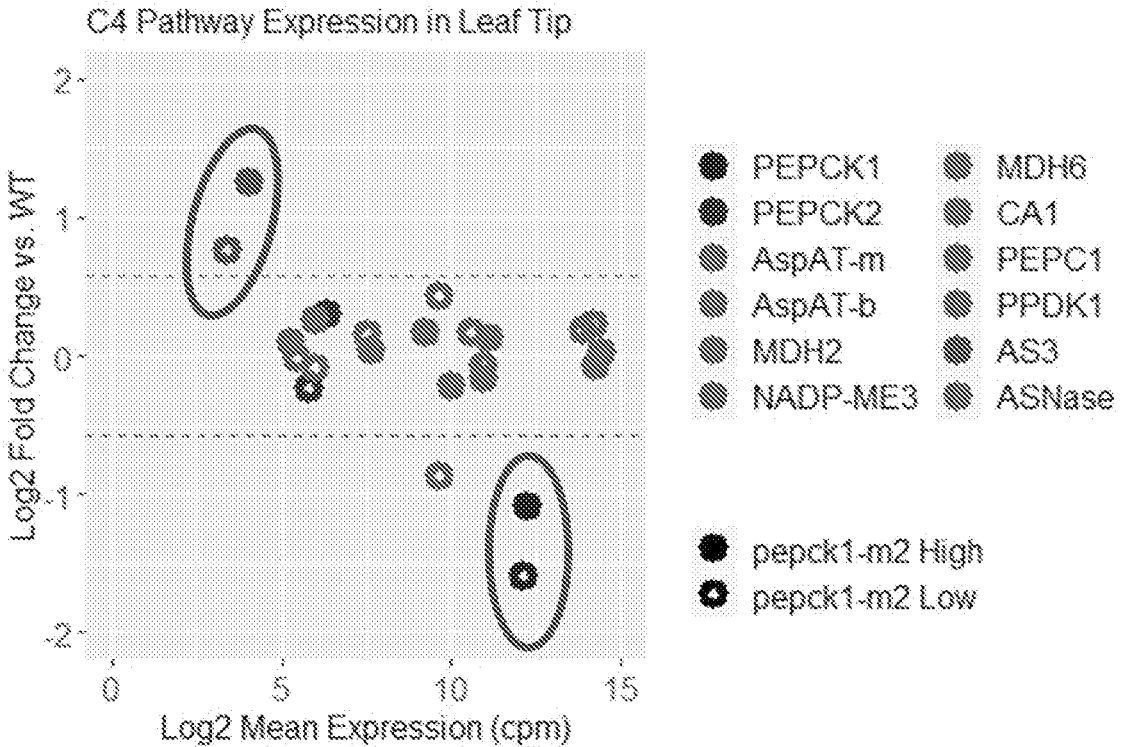
FIG. 10. 3' end RNAseq was used to measure expression of $C_4$ pathway genes in the pepck1::Ds2 and W22 leaf tip at high and low N field conditions. PEPCK1 expression (blue) was reduced in the mutant, and most $C_4$ pathway genes were not differentially expressed. Asparagine synthetase 3 increased expression in the pepck1::Ds mutant under both nitrogen treatments, likely as a response to the accumulation of aspartate in the mutant leaf.

Example 6. Transcriptional Response of $C_4$ Photosynthetic Genes Indicated Slight Alterations to Carbon and Nitrogen Metabolism Gene expression changes were quantified from mature leaf tissue from 35-day-old maize plants grown in high or low nitrogen in the field for both pepck1::Ds alleles and W22. Gene expression analysis by 3' end RNAseq confirmed decreased expression of PEPCK1 in the mutant, by at least 1.5-fold, depending on nitrogen treatment. Expression of the homologous gene PEPCK2, which is expressed constitutively in the plant (Stelpflug et al., 2016) was unchanged and thus did not indicate compensation for decreased expression of PEPCK1. Similarly, genes comprising the NADP-ME $C_4$ pathway did not increase in expression to compensate (FIG. 10); however, expression of an asparagine synthetase (Zm00004b001218) was increased, perhaps in response to the accumulation of its substrate aspartate in the mutant leaf (FIG. 9C).

Figure 11:
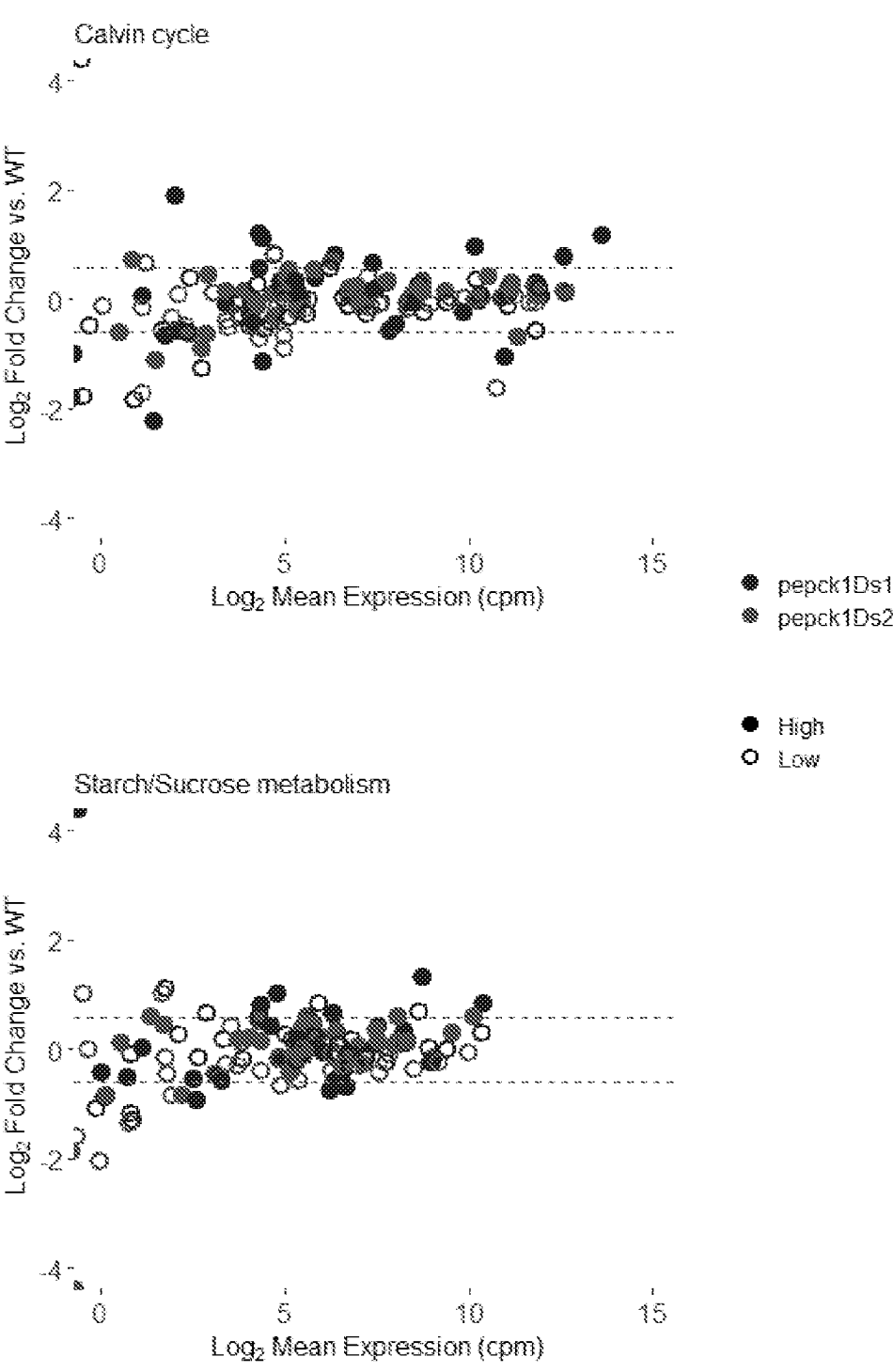
FIG. 11. Mean gene expression (log2 normalized) by fold-change from W22 (log2 normalized) for genes involved in Calvin Cycle, starch/sucrose metabolism, pyruvate metabolism, nitrogen metabolism or alanine, aspartate, and glutamine metabolism, based on GO annotation. Blue dots represent pepck1::Ds1, green dots pepck1::Ds2, and filled dots represent the high N treatment, open dots low N.
Figure 11:
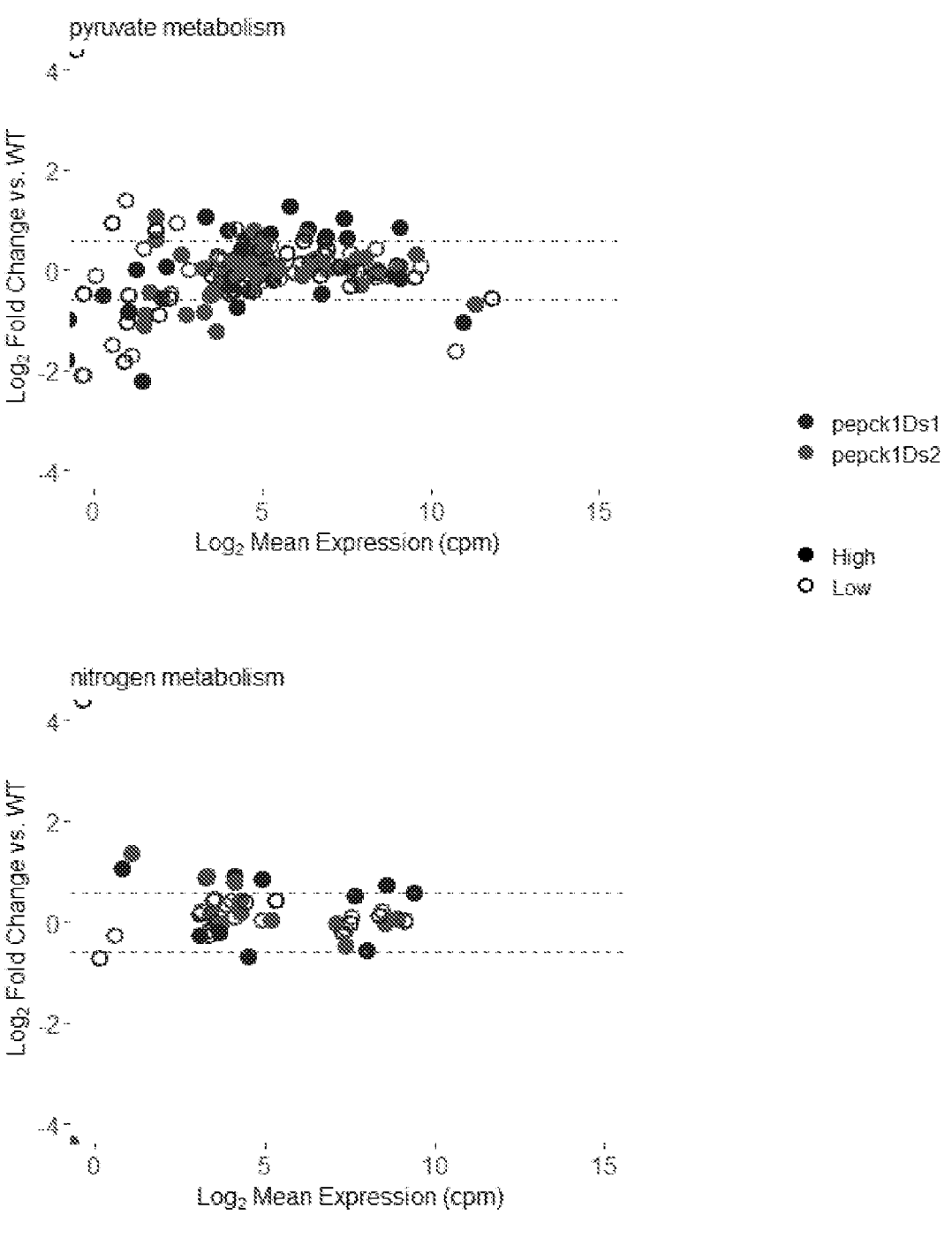
Figure 11:
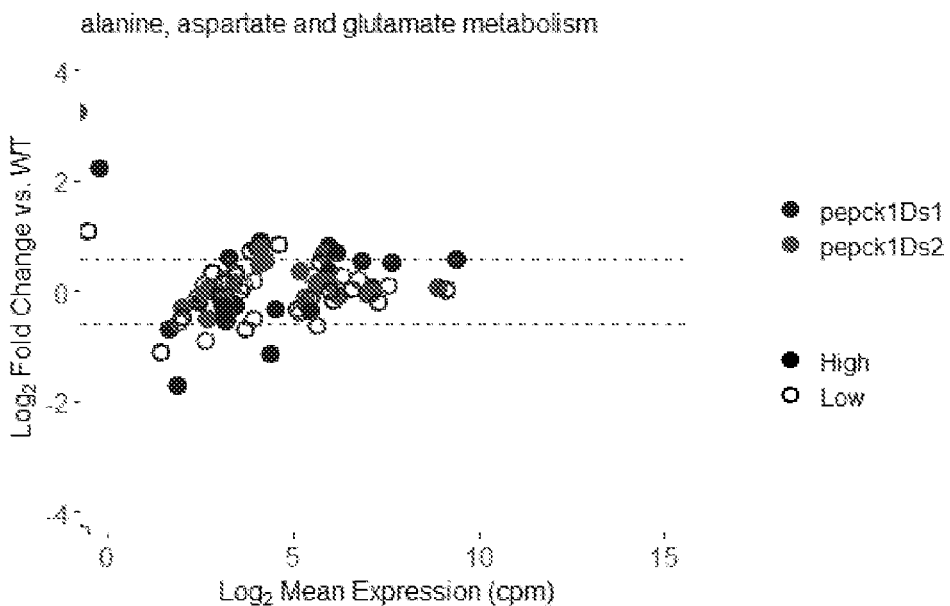

To further investigate the transcriptional response in the mutant and understand the role excess aspartate may play more broadly in metabolic pathways, we examined gene expression for central carbon metabolism pathways. For each individual metabolic pathway, there was no clear trend of differential expression in the mutant compared to W22, although some slight patterns emerged. Genes for the enzymes involved in central carbon metabolism were characterized in groups by pathway (FIG. 11). In the pepck1::Ds mutants, carbon metabolism genes had a slight trend toward increased expression, with pyruvate metabolism and starch/sucrose metabolism both slightly increased in the mutant. Similarly, CBC genes with moderate or high expression were apt to be expressed at a greater level in the mutant; however, genes expressed at low abundance showed greater differential expression overall between pepck1::Ds and W22. Genes involved in amino acid metabolism and nitrogen metabolism were also slightly increased in expression in the mutant (FIG. 11). In previous reports of the transcriptomic response to $C_4$ subtype, species using the NADP-ME pathway had decreased expression of protein synthesis genes, potentially due to the decreased amount of cellular aspartate (Brautigam et al, 2011; Gowik et al, 2011). However, in the current study, the genes involved in protein synthesis were remarkably stable in expression between the pepck1::Ds mutant and W22 leaves, in both high and low nitrogen treatments.

For a global analysis of the transcriptomic response in the mutant, differentially expressed genes were identified using EdgeR for the two nitrogen treatments (Table 3). For pepck1::Ds1, there were 489 transcripts differentially expressed at high N and 146 at low N. In pepck1::Ds2, there were 100 differentially expressed transcripts at high N and 335 at low N. Relatively few differentially expressed genes were shared between treatments. At high N, 12 genes were differentially expressed in both alleles, and 37 were found at low N. Similarly, a few genes were consistently differentially expressed in each mutant allele for both nitrogen treatments. In pepck1::Ds1, 20 genes were found in both N treatments; similarly, 19 genes were found in both N treatments for pepck1::Ds2. However, the set of genes were not similar between the alleles and only one gene, Zm00004b035571, was differentially expressed in both alleles and both N rates. The gene does not have an annotation nor is there a homolog in the maize B73 genome. Zm00004b035571 is orthologous to SORBI_3003G383900 and SORBI_3004G327500 in sorghum, Si031341m in *Setaria italica*, and OS04G0593400 in rice (Springer et al., 2018); MaizeGDB.org). None of the orthologous genes have a clear functional annotation. Gene ontology enrichment was performed on all differentially expressed genes (Table 4). Few terms were found to be overrepresented, likely due to the small number of differentially expressed genes. Overall, the gene set was enriched for stress response genes (GO:0006950). The genes differentially expressed in both pepck1::Ds alleles were enriched for genes involved in carboxylic acid metabolism (GO:0019752: GRMZM2G171556, GRMZM2G127067, GRMZM2G027726, GRMZM2G122324, GRMZM2G034360).

TABLE 3

| | Differentially Expressed Genes | | |
|---|---|---|---|
| | pepck1::Ds1 | pepck1::Ds2 | Both |
| High N | 489 | 100 | 12 |
| Low N | 146 | 335 | 37 |
| Both | 20 | 19 | 1 |

TABLE 4

Gene ontology (GO) enrichment

| N Rate | Allele | GO term | Ontology | Description | Number in input list | Number in BG/Ref | p-value | FDR |
|---|---|---|---|---|---|---|---|---|
| Low | Both | GO:0042180 | P | cellular ketone metabolic process | 5 | 1008 | 0.0011 | 0.011 |
| Low | Both | GO:0006082 | P | organic acid metabolic process | 5 | 989 | 0.001 | 0.011 |
| Low | Both | GO:0019752 | P | carboxylic acid metabolic process | 5 | 987 | 0.001 | 0.011 |
| Low | Both | GO:0043436 | P | oxoacid metabolic process | 5 | 987 | 0.001 | 0.011 |
| Low | Both | GO:0006950 | P | response to stress | 7 | 2243 | 0.0014 | 0.012 |
| Low | Both | GO:0050896 | P | response to stimulus | 8 | 3551 | 0.0049 | 0.033 |
| High | pepck 1-1 | GO:0050896 | P | response to stimulus | 84 | 3551 | 5.90E−09 | 7.80E−06 |
| High | pepck 1-1 | GO:0065004 | P | protein-DNA complex assembly | 11 | 124 | 1.00E−06 | 0.00024 |
| High | pepck 1-1 | GO:0034728 | P | nucleosome organization | 11 | 121 | 8.00E−07 | 0.00024 |
| High | pepck 1-1 | GO:0031497 | P | chromatin assembly | 11 | 123 | 9.30E−07 | 0.00024 |
| High | pepck 1-1 | GO:0006334 | P | nucleosome assembly | 11 | 121 | 8.00E−07 | 0.00024 |
| High | pepck 1-1 | GO:0006333 | P | chromatin assembly or disassembly | 11 | 125 | 1.10E−06 | 0.00024 |
| High | pepck 1-1 | GO:0009628 | P | response to abiotic stimulus | 40 | 1397 | 1.50E−06 | 0.00025 |
| High | pepck 1-1 | GO:0006323 | P | DNA packaging | 11 | 129 | 1.40E−06 | 0.00025 |
| High | pepck 1-1 | GO:0071103 | P | DNA conformation change | 11 | 172 | 1.90E−05 | 0.0028 |
| High | pepck 1-1 | GO:0042221 | P | response to chemical stimulus | 47 | 2052 | 5.40E−05 | 0.0073 |
| High | pepck 1-1 | GO:0006950 | P | response to stress | 50 | 2243 | 6.00E−05 | 0.0073 |
| High | pepck 1-1 | GO:0010038 | P | response to metal ion | 19 | 543 | 8.40E−05 | 0.0094 |
| High | pepck 1-1 | GO:0009266 | P | response to temperature stimulus | 17 | 464 | 0.00012 | 0.011 |
| High | pepck 1-1 | GO:0006325 | P | chromatin organization | 12 | 253 | 0.00013 | 0.011 |
| High | pepck 1-1 | GO:0051276 | P | chromosome organization | 13 | 292 | 0.00012 | 0.011 |
| High | pepck 1-1 | GO:0006575 | P | cellular amino acid derivative metabolic process | 12 | 269 | 0.00022 | 0.018 |
| High | pepck 1-1 | GO:0015979 | P | photosynthesis | 11 | 247 | 0.0004 | 0.031 |
| High | pepck 1-1 | GO:0044281 | P | small molecule metabolic process | 49 | 2372 | 0.00042 | 0.031 |
| High | pepck 1-1 | GO:0006996 | P | organelle organization | 22 | 799 | 0.00063 | 0.044 |
| High | pepck 1-1 | GO:0010035 | P | response to inorganic substance | 19 | 645 | 0.00068 | 0.045 |
| Low | pepck 1-1 | GO:0050896 | P | response to stimulus | 29 | 3551 | 6.10E−06 | 0.0026 |
| Low | pepck 1-1 | GO:0006950 | P | response to stress | 21 | 2243 | 2.40E−05 | 0.0052 |
| Low | pepck 1-1 | GO:0071103 | P | DNA conformation change | 5 | 172 | 0.00038 | 0.041 |
| Low | pepck 1-1 | GO:0009628 | P | response to abiotic stimulus | 14 | 1397 | 0.00034 | 0.041 |
| Low | pepck 1-1 | GO:0006631 | P | fatty acid metabolic process | 6 | 283 | 0.00051 | 0.044 |
| Low | pepck 1-2 | GO:0042221 | P | response to chemical stimulus | 35 | 2052 | 3.60E−05 | 0.032 |

Example 7. Double Mutant Knocking Out NADP-ME and PEPCK Pathways is Lethal

Figure 2D:
FIG. 2D Photograph showing the performance of pepck1::Ds; dct2::Ac double mutants 10 days after germination.

A maize plant without a carbon concentrating mechanism would not be expected to be viable, due to the reduced amount of $CO_2$ in bundle sheath cells for use by $C_4$-optimized Rubisco. To test this and to determine the strength of the pepck1::Ds alleles, the pepck1::Ds mutants were crossed to the dct2:Ac mutant reported in Weissmann et al., 2016 to generate a double mutant plant with loss of both the PEPCK pathway and NADP-ME pathway function. The dct2:Ac mutant is unable to import malate into the bundle sheath chloroplast, preventing the NADP-ME decarboxylation reaction (Weissmann et al., 2016). In the pepck1::Ds; dct2:Ac double mutant, seedlings were able to germinate, but the plants died approximately ten days after sowing, once the seed reserves were exhausted (FIG. 2D). Thus, maize plants require a $CO_2$ concentrating mechanism, and the pepck1::Ds alleles were effective at diminishing the PEPCK pathway.

Discussion for Examples 1-7

Questions remain about the metabolic operation and plasticity of the $C_4$ photosynthetic pathway in maize leaves, despite this being among the most important food sources in the world. Intensive farming and significant agricultural inputs including nitrogen fertilizer have resulted in high yields in the US but at a cost. The demand for inputs limits production on marginal land, reduces the net energy balance for biofuel feasibility, and fertilizer runoff results in eutrophication in waterways. An improvement in maize yield and nitrogen use efficiency could have dramatic consequences for US agriculture, the environment, and small farmers in developing countries. However, nitrogen use is intimately linked with photosynthetic carbon assimilation in $C_4$ crops, relying on combinations of $C_4$ subtype pathways that are species-dependent. The NADP-ME subtype is considered the most nitrogen efficient (Taub and Lerdau, 2000; Ghannoum et al., 2005; Pinto et al., 2014; Pinto et al., 2016). The involvement of PEPCK in addition to NADP-ME incurs a cost in additional protein synthesis for abundant photosynthetic enzymes, but may enable photosynthesis under variable conditions. However, while tandem pathway operation offers some potential gain under particular circumstances, we postulated that the cost to overall nitrogen status and use by the plant results in an overall less productive crop in the field through the course of plant life cycle.

To tease out the role of the PEPCK pathway relative to other $C_4$ photosynthetic subtypes, the inventors generated transposable element mutants. Two pepck1::Ds mutants were generated, along with a pepck1::Ds; dct2:Ac double mutant, which were confirmed by DNA, RNA expression, and enzymatic assays of PEPCK. A combination of transcriptomics, gas exchange, isotopic labeling, and four years of field studies in altered N conditions were used to characterize the lines. The pepck1::Ds mutant plants accumulated aspartate in the leaves, consistent with decreased PEPCK decarboxylation, as aspartate generation precedes PEPCK activity in the pathway. Additionally, in the pepck1::Ds plants, the response to fluctuating light was slower, and plants were not able to recover from shading to reach high levels of net $CO_2$ assimilation, particularly after repeated shading events, where energy pools would be more likely to have become imbalanced (FIG. 6). By changing the relative proportion of flux through the NADP-ME and PEPCK pathways, the plant can rebalance energy and reduce equivalents between the mesophyll and bundle sheath cells since the two pathways differ in the consumption of ATP and shuttling of reducing equivalents between cell types, which potentially alters the consequences of light harvesting and would be expected to be affected in these mutants (Pick et al., 2011; Stitt and Zhu, 2014; Wang et al., 2014).

The PEPCK-deficient plants provide an intriguing example for biotechnology. They outperformed W22 controls in the field and in the greenhouse; however, tests aimed at judging photosynthetic carbon assimilation steps including gas exchange measurements in fluctuating light and isotopic labeling experiments suggested that the enhanced biomass was not a consequence of improved carbon capture.

Without PEPCK as a decarboxylase, $C_4$ could operate dynamically using malate and aspartate alone, with aspartate being re-reduced to malate in the bundle sheath and utilizing the NADP-ME pathway (Wang et al., 2014). Computational modeling analyses indicated plants that made use of both malate and aspartate transfer with malic enzyme alone could have enhanced photosynthetic traits compared to plants that transfer aspartate and malate and use both malic enzyme and PEPCK as decarboxylases; however, such plants require the use of a hypothetical malate dehydrogenase in the bundle sheath (Wang et al., 2014). In the instant examples, the malate pools remained consistent in size in the mutant and nitrogen treatments, while aspartate accumulated in the pepck1::Ds mutant. Other $C_4$ shuttle metabolites including pyruvate, phosphoenolpyruvate, and alanine also had smaller pools in the pepck1::Ds mutant than W22 control plants, particularly in high nitrogen conditions, supportive of a reduction in the proportion of $C_4$ shuttle using the PEPCK pathway. Additionally, the pepck1::Ds mutant had reductions in the pool size of 3-PGA, the initial product of the Calvin Benson Cycle, possibly consistent with decreased CBC activity from slightly decreased Rubisco in response to decreased $C_4$ shuttle activity. Thus, despite the possibility that a plant may be able to shuttle aspartate for use in the $C_4$ pathway without decarboxylation by PEPCK (Gutierrez et al., 1974), this combination of metabolite pool size changes is consistent with reduced flux through PEPCK in the mutant and may argue that little flux of aspartate can be accommodated by a malate dehydrogenase in the bundle sheath.

Whereas gas exchange and metabolic observations could explain the benefit of maintaining PEPCK in maize tied to carbon assimilation steps, the enhanced performance throughout the plant lifetime without PEPCK measured in the field and greenhouse is likely related to other data that link photosynthesis with nitrogen use (Khamis et al., 1992; Taub and Lerdau, 2000; Ghannoum et al., 2005; Pinto et al., 2014; Pinto et al., 2016). In particular, the excess aspartate in the leaf represents intriguing possibilities for rebalancing carbon and nitrogen metabolism in the leaf. Aspartate serves roles in $C_4$ metabolism and protein biosynthesis pathways, among others, and under limiting N conditions, aspartate fulfills its other roles in metabolism before participating in the $C_4$ shuttle (Khamis et al., 1992). While others have shown that malate concentrations are often linked to nitrogen status of the plant (Salsac et al., 1987), in the instant examples, malate concentrations and moles involved in the $C_4$ shuttle (FIG. 9) were stable between the nitrogen treatments and between the pepck1::Ds mutant and W22 control, indicating that aspartate is the more responsive component of the $C_4$ shuttle. Thus, disturbing the PEPCK pathway and aspartate concentrations would be expected to alter plant N sensing (Seebauer et al., 2004). When the pepck1::Ds lines were grown in a nitrogen response field site over four years, the plants accumulated larger amounts of grain biomass and grain N than the W22 controls, with an overall average increase of 20% between all four field seasons and both nitrogen treatments. The degree of increase varied considerably, however, between field seasons with one allele producing 71-74% more grain biomass than W22 during the 2017 field season, and only 8-14% more biomass during 2018. The increased grain biomass was not an effect of larger overall plant size as the stover (stem and leaves) increased in biomass by an average of 6% averaged across the four seasons. Thus, the mutant plants had improved harvest index, and may reflect improved remobilization of metabolites and proteins from the leaves or altered priorities due to decreased source strength with less required N allocation to source proteins such as Rubisco and more to N demands in the kernel. Such a reallocation of nitrogen within the plant could allow the plant to grow more efficiently on a carbon basis. For plants with weak sink strength from small ear size, the decreased rate of photosynthesis in the pepck1::Ds mutant may be sufficient to support normal biomass production. The results presented herein support that many maize plants could be sink-limited rather than source-limited, and a change in prioritization of nutrition to sink tissue could be optimal compared to plants that prioritize too many resources to maintain excess source tissue. Indeed, in an agricultural setting, maize plants with only minimal resources devoted to leaf and stem tissues and strong remobilization to the grain would be the most profitable and efficient.

Conclusions for Examples 1-7

To understand the interaction between nitrogen metabolism and the $C_4$ shuttle, the inventors generated a mutant in PEPCK1, the minor decarboxylase used in maize. Using the Ac/Ds transposon tagging system, two alleles that decreased expression of PEPCK1 were generated. The resulting pepck1::Ds alleles were grown in a field site at high (220 kg/Ha) or no added nitrogen site for four years; the biomass of the vegetative tissues was not different in the mutant, but the grain biomass increased. Although there was year-to-year variation, grain biomass was higher in the mutant in 3 of 4 years and by up to 55-70% exhibited in 2017. The increase in grain biomass resulted from the impact of nitrogen imposed on photosynthetic carbon assimilation and possibly changes in source to sink allocation. These observations suggest the PEPCK pathway reduces NUE, which is most evident at low N conditions, consistent with the observed reduction in photosynthetic flux through aspartate in limiting N conditions. $C_4$ photosynthesis capitalizes on increased $CO_2$ provision to Rubisco that increases yield by reducing photorespiration and the required amounts of Rubisco. $C_4$ has implications on carbon and energy balances; however, the capacity to improve productivity is foremost limited by availability of nitrogen. In less ideal growing conditions such as subsistence farming or when fertilizer is not applied, breeding of plants should consider whether a PEPCK pathway is of benefit.

Methods for Examples 1-7

Ds Reverse Genetic Screening

Mutagenesis of the PEPCK1 locus in maize (GRMZM2G0001696; Zm00001d028471) was performed using the Ac/Ds tagging stock B.S07.0675R, located 601.7 kb 3' of the gene, as the donor Ds element. Because of the large distance between the donor Ds element and the PEPCK1 locus, the Ds element was remobilized in a two-step process where the transposon was first remobilized to a location closer to PEPCK then remobilized again in a second population. Populations for Ds screening were generated by crossing to W22:r-sc m3/r-sc:m3, and Ds element transposition into PEPCK1 was performed using the method established by Ahern et al. (Ahern et al., 2009). In the second screening population, eight hundred individuals were screened, and two alleles were identified and confirmed by Sanger sequencing of the PCR product of the amplified gene and Ds-specific primer. Gene expression was confirmed by qRT-PCR using primers PEPCK1-F: CCCGAT-CAACACCTGGACG (SEQ ID NO: 3) and PEPCK1-R: AATCATCTTCACACGCACCCA (SEQ ID NO 4). Gene expression was normalized using the delta delta Ct method, normalizing to GAPDH gene expression (GAPDH-F: GGCATCAGGAACCCTGAGGAAA (SEQ ID NO: 5), GAPDH-R: GATGTGCAGCAGCCTTGTCCTT SEQ ID NO: 6)).

Plant Material and Growth Conditions

Field experiments were conducted in a Drummer silty clay loam, pH 6.2. Maize (Zea mays L., genotype W22) plants were grown in a split-plot design where individuals in each main plot (6 rows 17.5 feet long, 76 cm row spacing) were paired in adjacent rows of that received either 150 kg/Ha fertilizer N (high N) or no exogenous applied N (low N). Based on N recovery from plots with no applied fertilizer at this field site, the soil N capacity was 90 kg ha$^{-1}$, and the site was subjected to a corn-soybean rotation to homogenize soil N. Fertilizer was applied as granular ammonium sulfate and hand incorporated in a diffuse band between the rows at the V3-V4 plant growth stage. Plots were maintained weed-free by a pre-plant application of herbicide (atrazine+metalochlor), followed by hand cultivation as needed. Plants were hand-pollinated to ensure adequate fertilization.

Biomass sampling was performed at physiological maturity (R6 growth stage) using a protocol modified from Haegele et al, 2013. The above ground biomass from five representative plants was sampled from the center of each plot and separated into ear (grain and cob) and stover (leaf, stem, and husk) fractions. Two plants from the stover fraction were oriented in the opposite direction of the remaining three plants to increase the homogeneity of the sample during chipping. The fresh weight of the stover fraction was measured, and the sample was shredded in a commercial brush chipper (Vermeer BC600XL; Vermeer Corporation). A representative 100-250 g aliquot of the chipped material was weighed and dried to calculate a moisture adjustment to determine dry weight of the total stover sample. The stover aliquot was further ground using a Wiley mill (Thomas Scientific) to pass through a 2 mm mesh screen and analyzed for percent nitrogen by combustion analysis in a Fissions NA 2000 N Analyzer. Ear samples were dried to 10% moisture and hand-shelled to partition and weigh the grain and cob. Whole kernel samples were analyzed on a Perten DA 7200 Near Infrared analyzer (NIR) to determine moisture, starch, oil, and protein concentrations (Uribelarrea et al., 2009). Grain nitrogen was calculated from percent protein using a conversion factor of 6.25 as used in the Kjeldahl method (Jones, 1931). Total Nitrogen Utilization is calculated as total biomass divided by total plant nitrogen. Grain Nitrogen Utilization is calculated as grain biomass divided by total plant nitrogen. Grain yields were mathematically adjusted to 0% moisture.

RNAseq Analysis

The two pepck1::Ds alleles and W22 control plants were sampled for RNA from the nitrogen response field. Tissue was sampled from plants at 30 days after sowing when the plants had reached the V10 growth stage. A 2-cm segment was sampled from leaf 13, approximately 10 cm from the tip of the leaf. Leaf samples were taken on a sunny morning between 10 AM and noon. Samples were immediately snap frozen in liquid N until further processing.

RNA was extracted using a CTAB, phenol, chloroform extraction procedure (Chang et al., 1993). Isolated RNA was treated with DNAseI (Turbo DNA-free, Invitrogen, catalog no. AM1907), and first strand cDNA synthesis was performed using Invitrogen Superscript III (catalog no. 18080051). 3' end FWD Lexogen libraries were constructed including unique sequences indices following the manufacturer instructions. Final library concentration was quantified using a Qubit3 fluorometer using the dsDNA HS kit (catalog no. Q33231) and confirmed using a Bioanalyzer Agilent DNA 1000 chip (catalog no. 5067-1504). Libraries were pooled in equimolar concentrations and sequenced. Sequencing was performed on a HiSeq4000 using 100 bp reads and with all 96 libraries multiplexed into a single lane. Libraries were quasi-aligned to the W22 genome (Springer et al., 2018) using Salmon (Patro et al., 2017). Differential expression was determined using EdgeR using the default parameters and pairwise comparisons of pepck1::Ds1 or pepck1::Ds2 to W22 for high N and low N treatments.

Gas Exchange Measurements

Gas exchange was measured using an LI-6800 Photosynthesis System (Li-Cor, Lincoln Nebraska). For A-Ci curves, plants were grown for 26 days in turface medium and fertilized three times per week with modified Hoagland's solution at 1.5 mM nitrate for low N treatment and 15 mM nitrate for high N (Hoagland et al., 1950). Plants were provided an excess of non-fertilized water for the duration of gas exchange measurements. A-Ci curves were quantified at 25° C. T leaf and 1500 $\mu$mol m$^{-2}$ s$^{-1}$ light; all other parameters were set to default. The top collared leaf was clamped into the fluorometer head using the 2 cm aperture setting. $CO_2$ concentration (in parts per million) was varied in the following pattern: 400, 300, 200, 100, 50, 20, 10, 400, 400, 400, 400, 400, 400, 400, 400, 500, 600, 700, 800, 900, 1000, 1200, 1500, 400. IRGAs were matched before each measurement and gas exchange parameters were allowed to stabilize for 60-90 seconds between sample measurements. Gas exchange measurements were also taken from pepck1-2:Ds and W22 plants 9 days after pollination from plants grown under normal growth conditions (25° C. day, 22° C. night, 50% relative humidity, minimum 500 $\mu$mol m$^{-2}$ sec$^{-1}$ light; DDPSC Plant Growth Facility maize protocol). Net $CO_2$ assimilation (A) was measured at steady-state on the leaf subtending the ear at 400 ppm $CO_2$ and 1500 $\mu$mol m$^{-2}$ s$^{-1}$ light.

Plants used in gas exchange measurements at Washington State University (Pullman, WA) were grown in a greenhouse under a minimum of 600 $\mu$mol m$^{-2}$ sec$^{-1}$ light, mean day and night temperature ($\pm$SD) was 25.6$\pm$1.3° C. and 22$\pm$1.5° C., respectively, and mean RH was 44.9$\pm$11.2%. They were planted in 11.3 L pots filled with potting soil (Sunshine LR1 mix, SunGro, Agawam, MA, USA). They were fertilized with 2.8 g/L 20–20–20+micronutrients (JR Peters Inc.) every other watering and 1.3 g/L iron chelate (Sprint 330, BASF) at 14 and 20 days.

For carbon discrimination ($\Delta^{13}C$) measurements, 4 plants of both WT22 and pepck1-1::Ds genotypes were measured with a LiCor 6800 and the exiting air was analyzed by a tunable diode laser (TDL-AS; Campbell Scientific, Logan, UT, USA). The LiCor chamber conditions were 31° C., and $CO_2$ concentration in the sample was 400 $\mu$mol mol$^{-1}$. Gas exchange and $\Delta^{13}C$ were measured for each plant at 2000, 1000, 700, and 400 $\mu$mol quanta m$^{-2}$ s$^{-1}$ photosynthetically active radiation (PAR), and the leaf remained at each light intensity during the time to reach steady state and record 10 cycles at 2 min 20 s intervals. In each cycle, the TDL-AS measured the carbon isotopes of both reference (inlet) and samples (outlet) air from the Licor chamber. Two calibration tanks (Liquid Technology) were used to calibrate for gain and possible offset in the TDL-AS measurements [see Bowling et al. (2003) and Ubierna et al. (2013)]. Photosynthetic $^{13}C$ discrimination was calculated as (Evans et al. (1986):

$$\Delta = \frac{1000\xi(\delta^{13}C_{sample} - \delta^{13}C_{ref})}{1000 + \delta^{13}C_{sample} - \xi(\delta^{13}C_{sample} - \delta^{13}C_{ref})} \qquad \text{Eqn. 1}$$

Where $\delta^{13}C_{sample}$ and $\delta^{13}C_{ref}$ are the carbon isotope composition of the leaf sample (chamber) and reference air of the LI-6800. The $\xi$ values were calculated as $\xi = C_{ref}/(C_{ref} - C_{sam})$, where $C_{ref}$ and $C_{sam}$ are the $CO_2$ concentrations of dry air entering and exiting the leaf chamber, respectively. The delta notation expressed in ‰ was relative to Vienna Pee Dee Belemnite carbon standard.

In vitro PEPC and Rubisco activity were measured at 25° C. on leaf tissue that was previously frozen in liquid nitrogen immediately after sampling. Leaf tissue was ground uniformly for 2 minutes using a pre-chilled mortar and pestle in 1 ml of 100 mM HEPES, (pH 7.8), 10 mM dithiothreitol, 1% polyvinylpolypyrrolidone, 1 mM EDTA, 0.1% (v/v) Triton, and 2% (v/v) of a plant protease inhibitor cocktail (P9599; Sigma-Aldrich, St Louis, MO, USA). A pinch of sand was added to facilitate grinding. Extract was centrifuged for 10 s at 4° C., and the supernatant was collected. Enzyme activity assays activity were initiated immediately. Rubisco and PEPC activity were measured at 30° C. using spectrophotometric assays by monitoring NADPH consumption at 340 nm as described by Sharwood et al., 2016 and Studer et al., 2014.

The fluctuating light experiment was conducted on 25-28 day old plants. Gas exchange measurements were made on the youngest, full-expanded leaf of 6 WT22 and 7 pepck1-1:Ds plants. Two LiCor 6800 were used to measure the effect of fluctuating light conditions on net photosynthetic rate ($A_{net}$). In the LiCor chamber, leaf chamber conditions set at 31° C., and sample $CO_2$ concentration was 450 $\mu$mol mol$^{-1}$. While stomatal conductance and $A_{net}$ were stabilizing, light intensity remained at 1500 $\mu$mol quanta m$^{-2}$ s$^{-1}$. Once stable, light intensity alternated between 1500 and 250 $\mu$mol quanta m$^{-2}$ s$^{-1}$ at the following intervals: 10 min at 1500, 10 min at 250, 10 min at 1500 then followed by 14 1-minute intervals of alternating 250 and 1500 light intensities. $A_{net}$ was measured every second throughout the experiment.

$^{13}CO_2$ Labeling

Plants were grown in the greenhouse from Dec. 15, 2018 to Feb. 6, 2019 under normal fertilization or no fertilization in Berger 35, 7% bark medium in 2.5 gallon pots. Plants were grown at 28° C. day, 22° C. night temperature, minimum 40% relative humidity, and 14-hour day length, 10-hour nights, with supplemental light provided when sunlight was below 600 $\mu$mol m$^{-2}$ s$^{-1}$. Plants were sampled 55 days after sowing.

$^{13}CO_2$ was provided to the leaf in a premixed gas at atmospheric concentrations of $O_2$ and $N_2$ and 350 ppm $^{13}CO_2$. The flow rate was 0.5 mL/min, and gas was provided to the underside of the maize leaf in an approximately 40 mL labeling chamber, with an outgassing hole on the top side of the chamber. Plants were sampled at 0, 10, 20, 30, 60, 90, 180, 300, and 600 s. Leaves were snap frozen by freeze clamp, submerged in liquid nitrogen, and kept at −80 C until further processing.

Metabolite Extraction

Metabolite dynamic labeling, pool size measurement and extracellular metabolite data were gathered and confirmed on two different LC-MS systems. All samples were extracted in a 3:7 (v/v) methanol (MeOH):chloroform solution containing acid washed glass beads at 4° C. for 6 hours, with the solution vortexed hourly. 0.5 mL of ddH₂O was added and the upper aqueous phase removed and centrifuged in 3 KDa filters at 0° C. Samples were then frozen, lyophilized and reconstituted in a 1:1 (v/v) MeOH:ddH₂O solution. 5 µM of PIPES was added as an internal standard prior to the extraction and used to normalize samples.

Chromatography and Mass Spectrometry Conditions

A Shimadzu Prominence-xR UFLC system was used for chromatographic separation and a SCIEX hybrid triple quadrupole-linear ion trap MS equipped with Turbo V™ electrospray ionization (ESI) source was used for detection of metabolites. The mobile phase solvents, A and B, contained 10 mM ammonium acetate and 5 µM medronic acid in water and 9:1 acetonitrile:ddH₂O, respectively. A 3 µL sample was injected on to an InfinityLab Poroshell 120 HILIC-Z (2.1× 100 mm, 2.7 µm, Agilent Technologies) column that was held at 40° C., and the following gradient was used: the initial concentration of 95% B was linearly decreased to 70% B over 8 min, and to 50% B over the next 4 min. The gradient was then brought to 30% B over 0.5 min and was held for an additional 1.0 min for clean up before returning to 95% B over 0.5 min. A 6 min equilibration was used to return the column to the starting conditions prior to the next injection. The total runtime was 20 min, and a flowrate of 250 µL/min was used throughout. A polarity switching method was used with sugar phosphates, sugars, organic acids and mevalonate pathway intermediates detected in negative ionization mode and the amino acids in positive ionization mode using a targeted MRM approach. The source conditions used were as follows; ion spray voltage, 4.5 kV (ESI+ and ESI−); ion source temperature, 400° C.; source gas 1, 45; source gas 2, 40; and curtain gas, 35. Data for absolute quantifications were analyzed using the quantitation wizard available in Analyst (v. 1.6.2) software (SCIEX, Concord, Canada). ¹³C enrichment measurements were quantified via manual integration of peaks.

REFERENCES

Ahern K R, Deewatthanawong P, Schares J, Muszynski M, Weeks R, Vollbrecht E, Duvick J, Brendel V P, Brutnell T P (2009) Regional mutagenesis using Dissociation in maize. Methods 49: 248-254.

Arrivault S, Obata T, Szecówka M, Mengin V, Guenther M, Hoehne M, Fernie A R, Stitt M (2017) Metabolite pools and carbon flow during C₄ photosynthesis in maize: 13CO2 labeling kinetics and cell type fractionation. J Exp Bot 68: 283-298

Bräutigam A, Gowik U (2016) Photorespiration connects C₃ and C₄ photosynthesis. J Exp Bot 67: 2953-2962.

Brown R H (1978) A difference in N use efficiency in C₃ and C₄ plants and its implications in adaptation and evolution 1. Crop Sci 18: 93-98.

Chang S, Puryear J, Cairney J (1993) A simple and efficient method for isolating RNA from pine trees. Plant Mol Biol Rep 11: 113-116.

Chapman K S, Hatch M D (1979) Aspartate stimulation of malate decarboxylation in Zea mays bundle sheath cells:

possible role in regulation of C₄ photosynthesis. Biochem Biophys Res Commun 86: 1274-1280.

Chapman K S R, Hatch M D (1981) Aspartate Decarboxylation in Bundle Sheath Cells of Zea mays and Its Possible Contribution to C₃ Photosynthesis. Funct Plant Biol 8: 237-248.

Covshoff S, Szecowka M, Hughes T E, Smith-Unna R, Kelly S, Bailey K J, Sage T L, Pachebat J A, Leegood R, Hibberd J M (2016) C₄ Photosynthesis in the Rice Paddy: Insights from the Noxious Weed Echinochloa glabrescens. Plant Physiol 170: 57-73.

Diaz R J, Rosenberg R (2008) Spreading dead zones and consequences for marine ecosystems. Science 321: 926-929.

Edwards G E, Franceschi V R, Voznesenskaya E V (2004) Single-cell C(4) photosynthesis versus the dual-cell (Kranz) paradigm. Annu Rev Plant Biol 55: 173-196.

Farquhar G D (1983) On the Nature of Carbon Isotope Discrimination in C4 Species. Funct Plant Biol 10: 205-226.

Furbank R T (2011) Evolution of the C(4) photosynthetic mechanism: are there really three C(4) acid decarboxylation types? J Exp Bot 62: 3103-3108.

Furumoto T, Hata S, Izui K (1999) cDNA cloning and characterization of maize phosphoenolpyruvate carboxykinase, a bundle sheath cell-specific enzyme. Plant Mol Biol 41: 301-311.

Galili G (2011) The aspartate-family pathway of plants: linking production of essential amino acids with energy and stress regulation. Plant Signal Behav 6: 192-195.

Ghannoum O, Evans J R, Chow W S, Andrews T J, Conroy J P, von Caemmerer S (2005) Faster Rubisco is the key to superior nitrogen-use efficiency in NADP-malic enzyme relative to NAD-malic enzyme C4 grasses. Plant Physiol 137: 638-650.

Gowik U, Bräutigam A, Weber K L, Weber A P M, Westhoff P (2011) Evolution of C4 Photosynthesis in the Genus Flaveria: How Many and Which Genes Does It Take to Make C4? Plant Cell 23: 2087-2105

Gutierrez M, Kanai R, Huber S C, Ku S B, Edwards G E (1974) Photosynthesis in mesophyll protoplasts and bundle sheath cells of various types of C4 plants I. Carboxylases and CO2 fixation studies. Zeitschrift für Pflanzenphysiologie 72: 305-319.

Hatch M D (1987) C₄ photosynthesis: a unique elend of modified biochemistry, anatomy and ultrastructure. Biochimica et Biophysica Acta (BBA)—Reviews on Bioenergetics 895: 81-106.

Hatch M D, Kagawa T, Craig S (1975) Subdivision of C₄-Pathway Species Based on Differing C₄ Acid Decarboxylating Systems and Ultrastructural Features. Funct Plant Biol 2: 111-128.

Hatch M D, Slack C R (1966) Photosynthesis by sugar-cane leaves. A new carboxylation reaction and the pathway of sugar formation. Biochem J 101: 103-111.

Hoagland D R, Arnon D I, Others (1950) The water-culture method for growing plants without soil. Circular. California agricultural experiment station 347:

Jones D B (1931) Factors for Converting Percentages of Nitrogen in Foods and Feeds Into Percentages of Proteins. U.S. Department of Agriculture.

Khamis S, Lamaze T, Farineau J (1992) Effect of nitrate limitation on the photosynthetically active pools of aspartate and malate in maize, a NADP malic enzyme C 4 plant. Physiol Plant 85: 223-229.

Majeran W, Cai Y, Sun Q, van Wijk K J (2005) Functional differentiation of bundle sheath and mesophyll maize chloroplasts determined by comparative proteomics. Plant Cell 17: 3111-3140.

Patro R, Duggal G, Love M I, Irizarry R A, Kingsford C (2017) Salmon provides fast and bias-aware quantification of transcript expression. Nat Methods 14: 417-419.

Pick T R, Bräutigam A, Schlüter U, Denton A K, Colmsee C, Scholz U, Fahnenstich H, Pieruschka R, Rascher U, Sonnewald U, et al (2011) Systems analysis of a maize leaf developmental gradient redefines the current C4 model and provides candidates for regulation. Plant Cell 23: 4208-4220.

Pinto H, Powell J R, Sharwood R E, Tissue D T, Ghannoum O (2016) Variations in nitrogen use efficiency reflect the biochemical subtype while variations in water use efficiency reflect the evolutionary lineage of C4 grasses at inter-glacial CO2. Plant Cell Environ 39: 514-526.

Pinto H, Sharwood R E, Tissue D T, Ghannoum O (2014) Photosynthesis of C3, C3-C4, and C4 grasses at glacial CO2. J Exp Bot 65: 3669-3681.

Rao X, Dixon R A (2016) The Differences between NAD-ME and NADP-ME Subtypes of C4 Photosynthesis: More than Decarboxylating Enzymes. Front Plant Sci 7: 1525.

Sage R F, Christin P-A, Edwards E J (2011) The C(4) plant lineages of planet Earth. J Exp Bot 62: 3155-3169.

Salsac L, Chaillou S, Morot-Gaudry J-F, Lesaint C H, Jolivet E (1987) Nitrate and ammonium nutrition in plants. Plant Physiol Biochem 25: 805-812.

Schlüter U, Bräutigam A, Droz J-M, Schwender J, Weber A P M (2018) The role of alanine and aspartate aminotransferases in C 4 photosynthesis. Plant Biol J 68: 283.

Sinclair T R, Rufty T W, Lewis R S (2019) Increasing Photosynthesis: Unlikely Solution For World Food Problem. Trends Plant Sci 24: 1032-1039.

Springer N M, Anderson S N, Andorf C M, Ahern K R, Bai F, Barad O, Barbazuk W B, Bass H W, Baruch K, Ben-Zvi G, et al (2018) The maize W22 genome provides a foundation for functional genomics and transposon biology. Nat Genet. doi: 10.1038/s41588-018-0158-0.

Stat FAO (2018) Food balance sheets.

Stelpflug S C, Sekhon R S, Vaillancourt B, Hirsch C N, Buell C R, de Leon N, Kaeppler S M (2016) An Expanded Maize Gene Expression Atlas based on RNA Sequencing and its Use to Explore Root Development. Plant Genome. doi: 10.3835/plantgenome2015.04.0025.

Stitt M, Zhu X-G (2014) The large pools of metabolites involved in intercellular metabolite shuttles in C4 photosynthesis provide enormous flexibility and robustness in a fluctuating light environment. Plant Cell Environ 37: 1985-1988.

Taub D R, Lerdau M T (2000) Relationship between leaf nitrogen and photosynthetic rate for three NAD-ME and three NADP-ME C4 grasses. Am J Bot 87: 412-417.

Uribelarrea M, Crafts-Brandner S J, Below F E (2009) Physiological N response of field-grown maize hybrids (Zea mays L.) with divergent yield potential and grain protein concentration. Plant Soil 316: 151.

Von Caemmerer S (2000) Biochemical Models of Leaf Photosynthesis. Csiro Publishing.

Walker R P, Acheson R M, Técsi L I, Leegood RC (1997) Phosphoenolpyruvate Carboxykinase in C4 Plants: Its Role and Regulation. Funct Plant Biol 24: 459-468.

Wang Y, Bräutigam A, Weber A P M, Zhu X-G (2014) Three distinct biochemical subtypes of C4 photosynthesis? A modelling analysis. J Exp Bot 65: 3567-3578.

Weissmann S, Ma F, Furuyama K, Gierse J, Berg H, Shao Y, Taniguchi M, Allen D K, Brutnell TP (2016) Interactions of C4 Subtype Metabolic Activities and Transport in Maize Are Revealed through the Characterization of DCT2 Mutants. Plant Cell 28: 466-484.

Wingler A, Walker R P, Chen Z H, Leegood R C (1999) Phosphoenolpyruvate carboxykinase is involved in the decarboxylation of aspartate in the bundle sheath of maize. Plant Physiol 120: 539-546.

Hoagland D R, Arnon D I. 1950. The water-culture method for growing plants without soil. Circular: California Agricultural Experiment Station 347, 32.

SEQUENCE LISTING

| SEQ ID NO | Sequence | Description |
|---|---|---|
| 1 | Gtagggtagt acaattcagg gcgtgtagac aaatcagtgg agccgataag tttatgcata agaaaagtca gtgattttat taactacttt ctctcccaga acaaacttcg caaggcacag ctgtcgcagt cacaccgatt tggctagcct ccctccggtt agcaactttg gagtattagc aagcatacag gagtaaacaa gtagctaagc aaatgcagat tcagaataat gcaaatattg tgttaagccg cagatggtat aaacagaaga cgtgcaaata tttgttatta gaaaaaaaac gttacagaaa aggggggaat ttcaaaaagg ataagctcca ctgctgctcc agagtgcaaa aacccaaacc caacccggaa cgaaagcgcc gccgccgttg aatggtcggg tagaggacgt aaccatggtt cactgccggg ccctttaaaa gccgagccag gctcgtccca tccgccccac gaccgcttgg cgcttcatca ctcgtttcct ttcgaaagcc cgcgcacgca cgtcggtcgt cccgtacgtg tgcccgtcta tctatcctcc tcgactctgt cgtgtctctt caactccgag agtgtccggg agcagagagc atcgatcaat ggcggggttt ggtctggtct ggtctggtcc catcccagca gggtcgctaa tgcgcgctcg ctgctgcttc tctctctgca ggagcaggac ctcgatcggc cgagatggcg acgccgaacg ggcttgcgcg gatcgagacg accgggaaga agaagcagga caacggcgtg tggtacgacg acagctcggc gccggtgcgc gcgcagacca tcgacgagct gcactcgctg cagcggaagc ggtcggcgcc cagcacgccc aagcggtcgg cgcccaccac gcccatcaag ggcggcgccc actcgccctt cgccgtcgcg atctccgagg aggagcgcca cacgcagcag atgcagtcca tcaggtgacg ttcgtccttt ctcagctagc atgattctgc cgccactagg cactagctaa gtagctagcc tgccgctata aacgaattgg tgaaaacgat ttctcgattt ggttgggttt tggttcatta ctgaataata atagcttaac gacaatggcc aacccaggca | Zea maise. PEPCK Ds insertion at the flanking edge of exon 8 (pepck1-1::Ds) |

-continued

| SEQ ID NO | Sequence | Description |
|---|---|---|
| | catgaaaggt aagcggagat | |
| | gagttccttt acccttttgg | |
| | gaaaggaaaa aaaaaaagac | |
| | aaaataattt ggcgtctgct | |
| | ggacttcctc tgggagaaga | |
| | aggaacggaa caaaaccaga | |
| | gctctgccac cgacgtcaga | |
| | gcccggcccg tttacgttga | |
| | caatacacac actgcctcgt | |
| | gggccctctt aagatagcac | |
| | ttggtgtgag ttgtggactt | |
| | cattagaaaa aaagtaaaag | |
| | gatggagaag atagaaatag | |
| | gtaaaaacaa aagggtgacg | |
| | cacgaaacga acaagcatta | |
| | ggtaataggt actacaaaca | |
| | cgcagcttga cgcgacacca | |
| | cggtcgccgt cggccacgca | |
| | acgtgctcct ttatctctgc | |
| | aggaaaccta gtaatccttc | |
| | ccgaaaatct gtacgtcctt | |
| | cggggggtcgg ctgtgtcctc | |
| | ccggtctcgc gcaccactaa | |
| | ccattttttgg tgctgataat | |
| | cgggagcgta gcgtaattac | |
| | cactaaacat ttttttttccc | |
| | gatctctcgt gatggatgca | |
| | gtgcgtcgtt ggcgtctctg | |
| | acgcgtgaaa ccgggccgaa | |
| | agtggtcaag ggcgacccgg | |
| | cggcgaaggg agaggccgcc | |
| | gcgcagggcg cgccatcgac | |
| | gccgagggcg caccagcagc | |
| | accgccaccc cgccgccccc | |
| | gccatcgccg tcagcgacag | |
| | ctccctcaag ttcactcatg | |
| | tgctcaacaa cctctcgcct | |
| | gctggtaagc atcgcataac | |
| | gcatatgcac aacctgatca | |
| | gcttcttcgc gttgcgttgc | |
| | gatgcgagag actaactgct | |
| | gacggatgct tactttgtcc | |
| | ctctgctgcc tgtcactcaa | |
| | aaacctatta aaaacgaaaa | |
| | acagagctgt acgagcaggc | |
| | catcaagtac gagaaggggt | |
| | cgttcatcac gtccaccggc | |
| | gcgctggcga cgctgtctgg | |
| | tgccaagacc gggcggtctc | |
| | ccagggacaa gcgcgtcgtc | |
| | aaggacgagg tcaccgcgca | |
| | ggacctgtgg tggggcaagt | |
| | gagtgtctgg ctgtctgctc | |
| | gagctcggca cacgtttctg | |
| | ctaccctacc tgtgtgtttc | |
| | ttcgccgctg acgtccgtgg | |
| | ctgacgatcg ggtgcaggg | |
| | ctcgcccaac atcgagatgg | |
| | acgagaagac gttcctgatc | |
| | aacagggaga gggccgtcga | |
| | ctacctcaac tccctggaga | |
| | aggtgttcgt caacgaccag | |
| | tacctcaact gggaccccga | |
| | gaaccggatc aaggtccgca | |
| | tcatctctgc cagggcgtac | |
| | cactccctct tcatgcacaa | |
| | catgtaagcc aacccggcct | |
| | ataccatact atcatcgtct | |
| | tccttgttga ggcggcccta | |
| | gagtataact ggatggggcc | |
| | gggccgggct cggtcgcagg | |
| | tgcatccgcc ccacggacga | |
| | ggagctggag gacttcggca | |
| | cgccggactt caccatctac | |
| | aacgcagggc agttcccctg | |
| | caaccgctac acccactaca | |

-continued

| SEQ ID NO | Sequence | Description |
|---|---|---|
| | tgacgtcgtc cacgagcata | |
| | gacctcaacc tcgccaggag | |
| | ggagatggtc atcatgggca | |
| | cgcagtacgc cggcgagatg | |
| | aagaaggggc tcttcggcgt | |
| | catgcactac ctcatgccca | |
| | agcgcggcat cctctcgctg | |
| | cactccggct gcaatatggg | |
| | caaggacggc gacgtcgccc | |
| | tcttctttgg cctctcaggt | |
| | aaacatggat gagaagagat | |
| | ggttgtgcgt ggcgccgcca | |
| | cctgcccaag tcgcattcgc | |
| | ttaccttgtc cttcgtgtca | |
| | tgtacgtcgt cttatatccg | |
| | ctgatcttac aacaggtacc | |
| | gggaagacga cgctgtcgac | |
| | ggatcacaac aggcttctga | |
| | tcggcgacga cgagcactgc | |
| | tggagcgaca atggcgtgtc | |
| | caacatcgag ggaggctgct | |
| | acgccaagtg catcgacctg | |
| | gcgcaggaga aagaacctga | |
| | tatttggaac gccatcaagt | |
| | ttggaactgg tacgtacttg | |
| | tctcgaactt tcggtttctt | |
| | cctttctttc gccggctgaa | |
| | ttgggttggg tagctgaact | |
| | gaatgtttct gctccagtgc | |
| | tggagaacgt ggtctttgat | |
| | gagcatactc gtgaagtcga | |
| | ctacgccgac aactctgtca | |
| | ccggtaaatg tcgcgtccct | |
| | agtccctact acacggacaa | |
| | gcaccaccaa agaaaaaaaa | |
| | aaaacttgtg tggtctcatc | |
| | tcatgcatgc atggcgctgt | |
| | tgttaattct tgcattgatt | |
| | gtagggatga aagtaggatg | |
| | ggaaaatccc gtaccgaccg | |
| | ttatcgtata accgattttg | |
| | ttagtttttat cccgatcgat | |
| | ttcgaacccg aggtaaaaaa | |
| | cgaaaacgga acggaaacgg | |
| | gatatacaaa acggtaaacg | |
| | gaaacggaaa cggtagagct | |
| | agtttcccga ccgtttcacc | |
| | gggatcccgt ttttaatcgg | |
| | aatgatcccg tttcgttacc | |
| | gtattttcta attcgggatg | |
| | actgcaatat ggccagctcc | |
| | aactcccatc cataaccact | |
| | gaggcccagc ccatgtaaga | |
| | aatacctagc gaacgctgct | |
| | ctgcctctct cccaggcggc | |
| | caggcaccac acgagtaaca | |
| | gcatcacaca ttcacacgcc | |
| | gccacgcgcc cacgccggag | |
| | tccggacgcc gccagccgca | |
| | cgccgacgcc ggcgacgcgt | |
| | ctcgctctcg cctgctctct | |
| | ccgactctcc ctgtctccca | |
| | gccggccggc cgctgggctg | |
| | caccaggcac cacacgcggt | |
| | gacggccgtg acgaggcacg | |
| | ccggacgcag acgccgccat | |
| | ccacggtccg ccctccactc | |
| | cactggctcgc gactcgccca | |
| | tccgcgccgc ggtccgccca | |
| | tccgcccaga cctccactcc | |
| | actgctcgcc catccgccggt | |
| | ccgcccatcc gccatccgcc | |
| | atctgcgggtc agcgttcctc | |
| | cagacctcca ctgctcggcg | |
| | ctcgcccatc cggccatccg | |
| | cggtctccct gtctccacgg | |

-continued

| SEQ ID NO | Sequence | Description |
|---|---|---|
| | ctgctcacag gctcacagca | |
| | cttagcagta cagcacgtca | |
| | gcaccattgc accaagctgt | |
| | tgtgtcattt gtgtgctgtc | |
| | caggggctct gcaacacctg | |
| | ctgattgctg tccagccgtc | |
| | caggtgctca caagtcacag | |
| | cagtacagca ccaagctgat | |
| | tgctgaacac ctgctgtcca | |
| | gggctctgct ctccacttcg | |
| | gctagccggc tacgactcca | |
| | ttcctcagat gacgcctccg | |
| | gttggaaata atcctccctc | |
| | aggctcagcc ataagattgg | |
| | ccaagttgat gctgttattg | |
| | ctgctgcaac aaatcatgag | |
| | aatcatatgg atgaggtatt | |
| | taaagattat tatttacttc | |
| | gtgcatgggc tattaatttg | |
| | ctattattca ctactgtttt | |
| | gatgcatggg ctgtttgctg | |
| | tcgccttgtt ttgatgcatg | |
| | cgccttgctg cccagccgtg | |
| | ttatactccc tgcatggctg | |
| | gcattaacag atttttgatc | |
| | tcactgcatg cgccttgtcg | |
| | ccttgttttg attggctgct | |
| | agctgctagc tgttaggctc | |
| | ccagctgtta ggcgctagct | |
| | gctagctgcc tagctcccag | |
| | ccgtgttagt tcacagattc | |
| | atgttctcct atatgtattt | |
| | atttatactc cctgcatatc | |
| | aattcatgtt cttctatatg | |
| | tatttattta tccaaaactg | |
| | acttattttt gtgtattaac | |
| | aggatgaaga cgcaatagaa | |
| | ttttctaaga ataatgaaga | |
| | tgtagcaagt ggctcctctc | |
| | catgagcaat gtgtcttatg | |
| | tttgttgaca gatgagcctt | |
| | ggttgtaata gtttatgcat | |
| | gctaagtgat ccagatgtga | |
| | gcaagtgatt atgaatatgt | |
| | gttttaaact ttatattgtg | |
| | tcatgtgtgc tagtagactt | |
| | atatggcttc ttatgttagc | |
| | caagagccca agacttatca | |
| | cttatgtgct acattaaact | |
| | atgtgtgctc cagatttata | |
| | tggattttat ctatgtttaa | |
| | ttaagacttg tgtttacaat | |
| | tttttatatt tgtttttaag | |
| | ttttgaatat atgtttttcat | |
| | gtgtgatttt accgaacaaa | |
| | aataccggtt cccgtccgat | |
| | ttcgacttta acccgaccgg | |
| | atcgtatcgg tttttcgatta | |
| | ccgtatttat cccgttcgtt | |
| | ttcgttaccg gtatatcccg | |
| | ttttcgtttc cgtcccgcaa | |
| | gttaaatatg aaaatgaaaa | |
| | cggtagaggt attttaccga | |
| | ccgttcccga ccgttttcat | |
| | ccctacagac agagaacact | |
| | cgggctgcct acccgatcga | |
| | gtacatcccc aacgccaaga | |
| | taccatgcgt cggcccgcac | |
| | cccaagaatg tgatcctcct | |
| | ggcgtgcgac gccttcggcg | |
| | tgctcccgcc ggtgagcaag | |
| | ctgaacctgg cgcagaccat | |
| | gtaccacttc atcagcgggt | |
| | acaccgctct ggtcgccggc | |
| | acggaggacg gcatcaagga | |
| | gccgcaggcc accttctccg | |

-continued

| SEQ ID NO | Sequence | Description |
|---|---|---|
| | cctgcttcgg cgcggccttc | |
| | atcatgctcc acccgaccaa | |
| | gtacgccgcc atgctcgccg | |
| | agaagatgca gaagtacggc | |
| | gccaccgggt ggctcgtcaa | |
| | caccggctgg tctggtggca | |
| | ggtacgcacg cggcacgacc | |
| | gtcacggttt ggtttgcttc | |
| | cggcagttgc acacagctcg | |
| | tgttcggtat gggaaaccgt | |
| | aggtttcatt gtgtgacggt | |
| | cgcttttgct tgtcaggtac | |
| | ggcgtgggca agaggatcag | |
| | gcttccctac accagaaaga | |
| | tcatcgacgc catccactcc | |
| | ggcgagctcc ttaccgccaa | |
| | ctaccagaag accgaggtgt | |
| | ttggcctgga gatccccact | |
| | gagatcaacg gcgtgccgtc | |
| | ggaaatcctc gacccgatca | |
| | acaccgtatg ctctgagtct | |
| | cacctcacga gctcgcttca | |
| | tcagtcatct tgaactatac | |
| | accctctgac caatttcgaa | |
| | cttgacaaat gctgtatata | |
| | tgcagtggac ggacaaggcc | |
| | gcgtacaagg agaatctcct | |
| | gaggctcggc gggctcttca | |
| | agaagaactt cgaggtgttc | |
| | gccagctaca agatcgggga | |
| | cgacagcagc ctgactgacg | |
| | agatcctcgc cgcaggcccc | |
| | aacttctgaa ctaaagcaat | |
| | ggatccggat gaataaaacg | |
| | atggtgtgtg tgcgtgggtg | |
| | cgtgtgaaga tgattacgac | |
| | gacgacgacg aaaaaaaagg | |
| | tgttggatcg atgagccaac | |
| | atagtaatag attagctggg | |
| | tattgtcatg ggtgcgtctg | |
| | gtgttgttat ctataaggct | |
| | gtttgcctgt cccaagcagc | |
| | tatcatattc tatttcaaat | |
| | tctattctgt aagcgtgtag | |
| | ttcaaaacaa tgctttacac | |
| | aaccatatgc acagtcttat | |
| | ctcaggttgg tctgttctat | |
| | cagcttgttg ggaaaagttt | |
| | gcgtgtgctt gtatcttgcc | |
| | ccctgtactc tctctggttt | |
| | ctgaatttgg atatgaaaca | |
| | gcttgatcgc gatcaccatt | |
| | ggttcggtat gtcatggcag | |
| | ga | |
| 2 | gtagggtagt acaattcagg gcgtgtagac aaatcagtgg agccgataag tttatgcata agaaaagtca gtgattttat taactacttt ctctcccaga acaaacttcg caaggcacag ctgtcgcagt cacaccgatt tggctagcct ccctccggtt agcaactttg gagtattagc aagcatacag gagtaaacaa gtagctaagc aaatgcagat tcagaataat gcaaatattg tgttaagccg cagatggtat aaacagaaga cgtgcaaata tttgttatta gaaaaaaaac gttacagaaa aggggggaat ttcaaaaagg ataagctcca ctgctgctcc agagtgcaaa aacccaaacc caacccggaa cgaaagcgcc gccgccgttg aatggtcggg tagaggacgt | *Zea maise*. PEPCK Ds insertion in the 3'UTR of the gene (pepck1-2::Ds) |

-continued

| SEQ ID NO | Sequence | Description |
|---|---|---|
| | aaccatggtt cactgccggg | |
| | ccctttaaaa gccgagccag | |
| | gctcgtccca tccgccccac | |
| | gaccgcttgg cgcttcatca | |
| | ctcgtttcct ttcgaaagcc | |
| | cgcgcacgca cgtcggtcgt | |
| | cccgtacgtg tgcccgtcta | |
| | tctatcctcc tcgactctgt | |
| | cgtgtctctt caactccgag | |
| | agtgtccggg agcagagagc | |
| | atcgatcaat ggcggggttt | |
| | ggtctggtct ggtctggtcc | |
| | catcccagca gggtcgctaa | |
| | tgcgcgctcg ctgctgcttc | |
| | tctctctgca ggagcaggac | |
| | ctcgatcggc cgagatggcg | |
| | acgccgaacg ggcttgcgcg | |
| | gatcgagacg accgggaaga | |
| | agaagcagga caacggcgtg | |
| | tggtacgacg acagctcggc | |
| | gccggtgcgc gcgcagacca | |
| | tcgacgagct gcactcgctg | |
| | cagcggaagc ggtcggcgcc | |
| | cagcacgccc aagcggtcgg | |
| | cgcccaccac gcccatcaag | |
| | ggcggcgccc actcgccctt | |
| | cgccgtcgcg atctccgagg | |
| | aggagcgcca cacgcagcag | |
| | atgcagtcca tcaggtgacg | |
| | ttcgtccttt ctcagctagc | |
| | atgattctgc cgccactagg | |
| | cactagctaa gtagctagcc | |
| | tgccgctata aacgaattgg | |
| | tgaaaacgat ttctcgattt | |
| | ggttgggttt tggttcatta | |
| | ctgaataata atagcttaac | |
| | gacaatggcc aacccaggca | |
| | catgaaaggt aagcggagat | |
| | gagttccttt acccttttgg | |
| | gaaaggaaaa aaaaaaagac | |
| | aaaataattt ggcgtctgct | |
| | ggacttcctc tgggagaaga | |
| | aggaacggaa caaaaccaga | |
| | gctctgccac cgacgtcaga | |
| | gcccggcccg tttacgttga | |
| | caatacacac actgcctcgt | |
| | gggccctctt aagatagcac | |
| | ttggtgtgag ttgtggactt | |
| | cattagaaaa aaagtaaaag | |
| | gatggagaag atagaaatag | |
| | gtaaaaacaa aagggtgacg | |
| | cacgaaacga acaagcatta | |
| | ggtaataggt actacaaaca | |
| | cgcagcttga cgcgacacca | |
| | cggtcgccgt cggccacgca | |
| | acgtgctcct ttatctctgc | |
| | aggaaaccta gtaatccttc | |
| | ccgaaaatct gtacgtcctt | |
| | cggggggtcgg ctgtgtcctc | |
| | ccggtctcgc gcaccactaa | |
| | ccattttttgg tgctgataat | |
| | cgggagcgta gcgtaattac | |
| | cactaaacat ttttttttccc | |
| | gatctctcgt gatggatgca | |
| | gtgcgtcgtt ggcgtctctg | |
| | acgcgtgaaa ccgggccgaa | |
| | agtggtcaag ggcgacccgg | |
| | cggcgaaggg agaggccgcc | |
| | gcgcagggcg cgccatcgac | |
| | gccgaggggcg caccagcagc | |
| | accgccaccc cgcgccaccc | |
| | gccatcgccg tcagcgacag | |
| | ctccctcaag ttcactcatg | |
| | tgctcaacaa cctctcgcct | |
| | gctggtaagc atcgcataac | |
| | gcatatgcac aacctgatca | |

-continued

| SEQ ID NO | Sequence | Description |
|---|---|---|
| | gcttcttcgc gttgcgttgc | |
| | gatgcgagag actaactgct | |
| | gacggatgct tactttgtcc | |
| | ctctgctgcc tgtcactcaa | |
| | aaacctatta aaaacgaaaa | |
| | acagagctgt acgagcaggc | |
| | catcaagtac gagaaggggt | |
| | cgttcatcac gtccaccggc | |
| | gcgctggcga cgctgtctgg | |
| | tgccaagacc gggcggtctc | |
| | ccagggacaa gcgcgtcgtc | |
| | aaggacgagg tcaccgcgca | |
| | ggacctgtgg tggggcaagt | |
| | gagtgtctgg ctgtctgctc | |
| | gagctcggca cacgtttctg | |
| | ctaccctacc tgtgtgtttc | |
| | ttcgccgctg acgtccgtgg | |
| | ctgacgatcg ggtgcagggg | |
| | ctcgcccaac atcgagatgg | |
| | acgagaagac gttcctgatc | |
| | aacaggggaga gggccgtcga | |
| | ctacctcaac tccctggaga | |
| | aggtgttcgt caacgaccag | |
| | tacctcaact gggacccccga | |
| | gaaccggatc aaggtccgca | |
| | tcatctctgc cagggcgtac | |
| | cactccctct tcatgcacaa | |
| | catgtaagcc aacccggcct | |
| | ataccatact atcatcgtct | |
| | tccttgttga ggcggcccta | |
| | gagtataact ggatggggcc | |
| | gggccgggct cggtcgcagg | |
| | tgcatccgcc ccacggacga | |
| | ggagctggag gacttcggca | |
| | cgccggactt caccatctac | |
| | aacgcaggggc agttcccctg | |
| | caaccgctac acccactaca | |
| | tgacgtcgtc cacgagcata | |
| | gacctcaacc tcgccaggag | |
| | ggagatggtc atcatgggca | |
| | cgcagtacgc cggcgagatg | |
| | aagaaggggc tcttcggcgt | |
| | catgcactac ctcatgccca | |
| | agcgcggcat cctctcgctg | |
| | cactccggct gcaatatggg | |
| | caaggacggc gacgtcgccc | |
| | tcttctttgg cctctcaggt | |
| | aaacatggat gagaagagat | |
| | ggttgtgcgt ggcgccgcca | |
| | cctgcccaag tcgcattcgc | |
| | ttaccttgtc cttcgtgtca | |
| | tgtacgtcgt cttatatccg | |
| | ctgatcttac aacaggtacc | |
| | gggaagacga cgctgtcgac | |
| | ggatcacaac aggcttctga | |
| | tcggcgacga cgagcactgc | |
| | tggagcgaca atggcgtgtc | |
| | caacatcgag ggaggctgct | |
| | acgccaagtg catcgacctg | |
| | gcgcaggaga aagaacctga | |
| | tatttggaac gccatcaagt | |
| | ttggaactgg tacgtacttg | |
| | tctcgaactt tcggtttctt | |
| | cctttctttc gccggctgaa | |
| | ttgggttggg tagctgaact | |
| | gaatgtttct gctccagtgc | |
| | tggagaacgt ggtctttgat | |
| | gagcatactc gtgaagtcga | |
| | ctacgccgac aactctgtca | |
| | ccggtaaatg tcgcgtccct | |
| | agtccctact acacggacaa | |
| | gcaccaccaa agaaaaaaaa | |
| | aaaacttgtg tggtctcatc | |
| | tcatgcatgc atggcgctgt | |
| | tgttaattct tgcattgcag | |
| | agaacactcg ggctgcctac | |

| SEQ ID NO | Sequence | Description |
|---|---|---|
| | ccgatcgagt acatccccaa | |
| | cgccaagata ccatgcgtcg | |
| | gcccgcaccc caagaatgtg | |
| | atcctcctgg cgtgcgacgc | |
| | cttcggcgtg ctcccgccgg | |
| | tgagcaagct gaacctggcg | |
| | cagaccatgt accacttcat | |
| | cagcgggtac accgctctgg | |
| | tcgccggcac ggaggacggc | |
| | atcaaggagc cgcaggccac | |
| | cttctccgcc tgcttcggcg | |
| | cggccttcat catgctccac | |
| | ccgaccaagt acgccgccat | |
| | gctcgccgag aagatgcaga | |
| | agtacggcgc caccgggtgg | |
| | ctcgtcaaca ccggctggtc | |
| | tggtggcagg tacgcacgcg | |
| | gcacgaccgt cacggtttgg | |
| | tttgcttccg gcagttgcac | |
| | acagctcgtg ttcggtatgg | |
| | gaaaccgtag gtttcattgt | |
| | gtgacggtcg cttttgcttg | |
| | tcaggtacgg cgtgggcaag | |
| | aggatcaggc ttccctacac | |
| | cagaaagatc atcgacgcca | |
| | tccactccgg cgagctcctt | |
| | accgccaact accagaaagac | |
| | cgaggtgttt ggcctggaga | |
| | tccccactga gatcaacggc | |
| | gtgccgtcgg aaatcctcga | |
| | cccgatcaac accgtatgct | |
| | ctgagtctca cctcacgagc | |
| | tcgcttcatc agtcatcttg | |
| | aactatacac cctctgacca | |
| | atttcgaact tgacaaatgc | |
| | tgtatatatg cagtggacgg | |
| | acaaggccgc gtacaaggag | |
| | aatctcctga ggctcggcgg | |
| | gctcttcaag aagaacttcg | |
| | aggtgttcgc cagctacaag | |
| | atcggggacg acagcagcct | |
| | gactgacgag atcctcgccg | |
| | caggccccaa cttctgaact | |
| | aaagcaatgg atccggatga | |
| | ataaaacgat ggtgtgtgtg | |
| | cgtgggtgcg tgtgaagatg | |
| | attacgacga cgacgacgaa | |
| | aaaaaaggtg ttggatcgat | |
| | gagccaacat agtaatagat | |
| | tagctgggta ttgtcatggg | |
| | tgggtgtagg gatgaaagta | |
| | ggatgggaaa atcccgtacc | |
| | gaccgttatc gtataaccga | |
| | ttttgttagt tttatcccga | |
| | tcgatttcga acccgaggta | |
| | aaaaacgaaa acggaacgga | |
| | aacgggatat acaaaacggt | |
| | aaacggaaac ggaaacggta | |
| | gagctagttt cccgaccgtt | |
| | tcaccgggat cccgttttta | |
| | atcggaatga tcccgtttcg | |
| | ttaccgtatt ttctaattcg | |
| | ggatgactgc aatatggcca | |
| | gctccaactc ccatccataa | |
| | ccactgaggc ccagcccatg | |
| | taagaaatac ctagcgaacg | |
| | ctgctctgcc tctctcccag | |
| | gcggccaggc accacacgag | |
| | taacagcatc acacattcac | |
| | acgccgccac gcgcccacgc | |
| | cggagtccgg acgccgccag | |
| | ccgcacgccg acgccggcga | |
| | cgcgtctcgc tctcgcctgc | |
| | tctctccgac tctccctgtc | |
| | tcccagccgg ccggccgctg | |
| | ggctgcacca ggcaccacac | |

| SEQ ID NO | Sequence | Description |
|---|---|---|
| | gcggtgacgg ccgtgacgcg | |
| | gcacgccgga cgcagacgcc | |
| | gccatccacg gtccgccctc | |
| | cactccactg ctcgcgactc | |
| | gcccatccgc gccgcggtcc | |
| | gcccatccgc ccagacctcc | |
| | actccactgc tcgcccatcc | |
| | gcggtccgcc catccgccat | |
| | ccgccatctg cggtcagcgt | |
| | tcctccagac ctccactgct | |
| | cggcgctcgc ccatccggcc | |
| | atccgcggtc tccctgtctc | |
| | cacggctgct cacaggctca | |
| | cagcacttag cagtacagca | |
| | cgtcagcacc attgcaccaa | |
| | gctgttgtgt catttgtgtg | |
| | ctgtccaggg gctctgcaac | |
| | acctgctgat tgctgtccag | |
| | ccgtccaggt gctcacaagt | |
| | cacagcagta cagcaccaag | |
| | ctgattgctg aacacctgct | |
| | gtccagggct ctgctctcca | |
| | cttcggctag ccggctacga | |
| | ctccattcct cagatgacgc | |
| | ctccggttgg aaataatcct | |
| | ccctcaggct cagccataag | |
| | attggccaag ttgatgctgt | |
| | tattgctgct gcaacaaatc | |
| | atgagaatca tatggatgag | |
| | gtatttaaag attattattt | |
| | acttcgtgca tgggctatta | |
| | atttgctatt attcactact | |
| | gttttgatgc atgggctgtt | |
| | tgctgtcgcc ttgttttgat | |
| | gcatgcgcct tgctgcccag | |
| | ccgtgttata ctccctgcat | |
| | ggctggcatt aacagatttt | |
| | tgatctcact gcatgcgcct | |
| | tgtcgccttg ttttgattgg | |
| | ctgctagctg ctagctgtta | |
| | ggctcccagc tgttaggcgc | |
| | tagctgctag ctgcctagct | |
| | cccagccgtg ttagttcaca | |
| | gattcatgtt ctcctatatg | |
| | tatttattta tactccctgc | |
| | atatcaattc atgttcttct | |
| | atatgtattt atttatccaa | |
| | aactgactta tttttgtgta | |
| | ttaacaggat gaagacgcaa | |
| | tagaattttc taagaataat | |
| | gaagatgtag caagtggctc | |
| | ctctccatga gcaatgtgtc | |
| | ttatgtttgt tgacagatga | |
| | gccttggttg taatagttta | |
| | tgcatgctaa gtgatccaga | |
| | tgtgagcaag tgattatgaa | |
| | tatgtgtttt aaactttata | |
| | ttgtgtcatg tgtgctagta | |
| | gacttatatg gcttcttatg | |
| | ttagccaaga gcccaagact | |
| | tatcacttat gtgctacatt | |
| | aaactatgtg tgctccagat | |
| | ttatatggat tttatctatg | |
| | tttaattaag acttgtgttt | |
| | acaatttttt atatttgttt | |
| | ttaagttttg aatatatgtt | |
| | ttcatgtgtg attttaccga | |
| | acaaaaatac cggttcccgt | |
| | ccgatttcga ctttaacccg | |
| | accggatcgt atcggttttc | |
| | gattaccgta tttatcccgt | |
| | tcgttttcgt taccggtata | |
| | tcccgtttttc gtttccgtcc | |
| | cgcaagttaa atatgaaaat | |
| | gaaaacggta gaggtatttt | |
| | accgaccgtt cccgaccgtt | |

| SEQ ID NO | Sequence | Description |
|---|---|---|
| | ttcatcccta cgtccgtctg | |
| | gtgttgttat ctataaggct | |
| | gtttgcctgt cccaagcagc | |
| | tatcatattc tatttcaaat | |
| | tctattctgt aagcgtgtag | |
| | ttcaaaacaa tgctttacac | |
| | aaccatatgc acagtcttat | |
| | ctcaggttgg tctgttctat | |
| | cagcttgttg ggaaaagttt | |
| | gcgtgtgctt gtatcttgcc | |
| | ccctgtactc tctctggttt | |
| | ctgaatttgg atatgaaaca | |

| SEQ ID NO | Sequence | Description |
|---|---|---|
| | gcttgatcgc gatcaccatt ggttcggtat gtcatggcag ga | |
| 3 | CCCGATCAACACCTGGACG | PEPCK1-F PCR primer |
| 4 | AATCATCTTCACACGCACCCA | PEPCK1-R PCR primer |
| 5 | GGCATCAGGAACCCTGAGGAAA | GAPDH-F PCR primer |
| 6 | GATGTGCAGCAGCCTTGTCCTT | GAPDH-R PCR primer |

What is claimed is:

1. A genetically modified maize plant having an increased grain biomass in limited nitrogen conditions as compared to that of a control maize plant cultivated under similar limited nitrogen conditions, wherein the modified maize plant comprises: a modified GRMZM2G001696 gene that comprises a nucleic acid sequence having at least 95% sequence identity to SEQ ID NO: 1 or SEQ ID NO: 2 and that encodes a phosphoenolpyruvate carboxykinase (PEPCK) enzyme at a reduced level or with reduced enzymatic activity as compared to that of a wild type maize plant; and wherein the grain biomass of the modified maize plant in limited nitrogen conditions is increased by about 20% as compared to that of a control maize plant cultivated under similar limited nitrogen conditions.

2. The modified maize plant of claim 1, wherein the modified GRMZM2G001696 gene comprising a nucleic acid sequence having at least 95% sequence identity to SEQ ID NO: 1 is characterized by having an insertion of a Dissociator (Os) element at the flanking edge of exon 8.

3. The modified maize plant of claim 1, wherein the modified GRMZM2G001696 gene comprising a nucleic acid sequence having at least 95% sequence identity to SEQ ID NO: 2 is characterized by having an insertion of a Os element in the 3' untranslated region (UTR).

4. A method of increasing the grain biomass of a maize plant cultivated under limited nitrogen conditions as compared to that of a control maize plant cultivated under similar limited nitrogen conditions, the method comprising: introducing into a maize plant, a genetic modification into an endogenous GRMZM2G001696 gene, thereby obtaining a modified maize plant comprising a modified GRMZM2G001696 gene that comprises a nucleic acid sequence having at least 95% sequence identity to SEQ ID NO: 1 or SEQ ID NO: 2 and that encodes a PEPCK enzyme at a reduced level or with reduced enzymatic activity as compared to that of a control maize plant; and cultivating the modified maize plant in limited nitrogen conditions, wherein the grain biomass of the modified maize plant in limited nitrogen conditions is increased by about 20% as compared to that of a control maize plant cultivated under similar limited nitrogen conditions.

* * * * *

SEQUENCE LISTING

```
<160> NUMBER OF SEQ ID NOS: 6

<210> SEQ ID NO 1
<211> LENGTH: 6782
<212> TYPE: DNA
<213> ORGANISM: Artificial Sequence
<220> FEATURE:
<223> OTHER INFORMATION: SYNTHESIZED
<220> FEATURE:
<221> NAME/KEY: source
<222> LOCATION: (1)..(6782)
<220> FEATURE:
<221> NAME/KEY: exon
<222> LOCATION: (712)..(994)
<223> OTHER INFORMATION: /label=Exon 1
<220> FEATURE:
<221> NAME/KEY: exon
<222> LOCATION: (1702)..(1904)
<223> OTHER INFORMATION: /label=Exon 2
<220> FEATURE:
<221> NAME/KEY: exon
<222> LOCATION: (2045)..(2198)
<223> OTHER INFORMATION: /label=Exon 3
<220> FEATURE:
<221> NAME/KEY: exon
<222> LOCATION: (2298)..(2483)
<223> OTHER INFORMATION: /label=Exon 4
<220> FEATURE:
<221> NAME/KEY: exon
<222> LOCATION: (2580)..(2878)
<223> OTHER INFORMATION: /label=Exon 5
<220> FEATURE:
<221> NAME/KEY: exon
<222> LOCATION: (2996)..(3169)
<223> OTHER INFORMATION: /label=Exon 6
<220> FEATURE:
<221> NAME/KEY: exon
<222> LOCATION: (3258)..(3323)
<223> OTHER INFORMATION: /label=Exon 7
<220> FEATURE:
<221> NAME/KEY: misc_feature
<222> LOCATION: (3434)..(3437)
<223> OTHER INFORMATION: /label=Ds Insertion Site 5' Flanking Repeat
<220> FEATURE:
<221> NAME/KEY: misc_feature
<222> LOCATION: (3438)..(3441)
<223> OTHER INFORMATION: /label=Ds Insertion Site 5' Flanking Repeat
<220> FEATURE:
<221> NAME/KEY: misc_feature
<222> LOCATION: (3442)..(5485)
<223> OTHER INFORMATION: /label=Ds Element
<220> FEATURE:
<221> NAME/KEY: misc_feature
<222> LOCATION: (5486)..(5489)
```

```
<223> OTHER INFORMATION: /label=Ds Insertion Site 3' Flanking Repeat
<220> FEATURE:
<221> NAME/KEY: misc_feature
<222> LOCATION: (5490)..(5493)
<223> OTHER INFORMATION: /label=Ds Insertion Site 3' Flanking Repeat
<220> FEATURE:
<221> NAME/KEY: exon
<222> LOCATION: (5493)..(5841)
<223> OTHER INFORMATION: /label=Exon 8
<220> FEATURE:
<221> NAME/KEY: exon
<222> LOCATION: (5957)..(6125)
<223> OTHER INFORMATION: /label=Exon 9
<220> FEATURE:
<221> NAME/KEY: exon
<222> LOCATION: (6226)..(6369)
<223> OTHER INFORMATION: /label=Exon 10
<220> FEATURE:
<221> NAME/KEY: 3'UTR
<222> LOCATION: (6370)..(6753)

<400> SEQUENCE: 1
gtagggtagt acaattcagg gcgtgtagac aaatcagtgg agccgataag tttatgcata        60
agaaaagtca gtgattttat taactacttt ctctcccaga acaaacttcg caaggcacag       120
ctgtcgcagt cacaccgatt tggctagcct ccctccggtt agcaactttg gagtattagc       180
aagcatacag gagtaaacaa gtagctaagc aaatgcagat tcagaataat gcaaatattg       240
tgttaagccg cagatggtat aaacagaaga cgtgcaaata tttgttatta gaaaaaaaac       300
gttacagaaa aggggggaat ttcaaaaagg ataagctcca ctgctgctcc agagtgcaaa       360
aacccaaacc caacccggaa cgaaagcgcc gccgccgttg aatggtcggg tagaggacgt       420
aaccatggtt cactgccggg ccctttaaaa gccgagccag gctcgtccca tccgccccac       480
gaccgcttgg cgcttcatca ctcgtttcct ttcgaaagcc cgcgcacgca cgtcggtcgt       540
cccgtacgtg tgcccgtcta tctatcctcc tcgactctgt cgtgtctctt caactccgag       600
agtgtccggg agcagagagc atcgatcaat ggcggggttt ggtctggtct ggtctggtcc       660
catcccagca gggtcgctaa tgcgcgctcg ctgctgcttc tctctctgca g gag cag       717
                                                                  Glu Gln
                                                                    1 gac ctc gat cgg ccg aga tgg cga cgc cga acg ggc ttg cgc gga tcg       765
Asp Leu Asp Arg Pro Arg Trp Arg Arg Arg Thr Gly Leu Arg Gly Ser
      5                  10                  15 aga cga ccg gga aga aga agc agg aca acg gcg tgt ggt acg acg aca       813
Arg Arg Pro Gly Arg Arg Ser Arg Thr Thr Ala Cys Gly Thr Thr Thr
     20                  25                  30 gct cgg cgc cgg tgc gcg cgc aga cca tcg acg agc tgc act cgc tgc       861
Ala Arg Arg Arg Cys Ala Arg Arg Pro Ser Thr Ser Cys Thr Arg Cys
35                  40                  45                  50 agc gga agc ggt cgg cgc cca gca cgc cca agc ggt cgg cgc cca cca       909
Ser Gly Ser Gly Arg Arg Pro Ala Arg Pro Ser Gly Arg Arg Pro Pro
                 55                  60                  65 cgc cca tca agg gcg gcg ccc act cgc cct tcg ccg tcg cga tct ccg       957
Arg Pro Ser Arg Ala Ala Pro Thr Arg Pro Ser Pro Ser Arg Ser Pro
             70                  75                  80 agg agc agc gcc aca cgc agc aga tgc agt cca tca g gtgacgttcg       1004
Arg Arg Ser Ala Thr Arg Ser Arg Cys Ser Pro Ser
             85                  90 tcctttctca gctagcatga ttctgccgcc actaggcact agctaagtag ctagcctgcc      1064
gctataaacg aattggtgaa aacgatttct cgatttggtt gggttttggt tcattactga      1124
ataataatag cttaacgaca atggccaacc caggcacatg aaaggtaagc ggagatgagt      1184
```

-continued

```
tcctttaccc ttttgggaaa ggaaaaaaaa aaagacaaaa taatttggcg tctgctggac      1244
ttcctctggg agaagaagga acggaacaaa accagagctc tgccaccgac gtcagagccc      1304
ggcccgttta cgttgacaat acacacactg cctcgtgggc cctcttaaga tagcacttgg      1364
tgtgagttgt ggacttcatt agaaaaaaag taaaaggatg gagaagatag aaataggtaa      1424
aaacaaaagg gtgacgcacg aaacgaacaa gcattaggta ataggtacta caaacacgca      1484
gcttgacgcg acaccacggt cgccgtcggc cacgcaacgt gctcctttat ctctgcagga      1544
aacctagtaa tccttcccga aaatctgtac gtccttcggg ggtcggctgt gtcctcccgg      1604
tctcgcgcac cactaaccat ttttggtgct gataatcggg agcgtagcgt aattaccact      1664 aaacatttt tttcccgatc tctcgtgatg gatgcag tg  cgt cgt tgg cgt ctc      1718
                                            Val Arg Arg Trp Arg Leu
                                                95              100 tga cgc gtg aaa ccg ggc cga aag tgg tca agg gcg acc cgg cgg cga      1766
    Arg Val Lys Pro Gly Arg Lys Trp Ser Arg Ala Thr Arg Arg Arg
            105             110                 115 agg gag agg ccg ccg cgc agg gcg cgc cat cga cgc cga ggg cgc acc      1814
Arg Glu Arg Pro Pro Arg Arg Ala Arg His Arg Arg Arg Gly Arg Thr
            120             125                 130 agc agc acc gcc acc ccg ccg ccc cca tcg ccg tca gcg aca gct          1862
Ser Ser Thr Ala Thr Pro Pro Pro Pro Ser Pro Ser Ala Thr Ala
            135             140                 145 ccc tca agt tca ctc atg tgc tca aca acc tct cgc ctg ctg              1904
Pro Ser Ser Ser Leu Met Cys Ser Thr Thr Ser Arg Leu Leu
        150             155                 160 gtaagcatcg cataacgcat atgcacaacc tgatcagctt cttcgcgttg cgttgcgatg      1964
cgagagacta actgctgacg gatgcttact ttgtccctct gctgcctgtc actcaaaaac      2024
ctattaaaaa cgaaaaacag agc tgt acg agc agg cca tca agt acg aga agg      2077
                        Ser Cys Thr Ser Arg Pro Ser Ser Thr Arg Arg
                                165                 170 ggt cgt tca tca cgt cca ccg gcg cgc tgg cga cgc tgt ctg gtg cca      2125
Gly Arg Ser Ser Arg Pro Pro Ala Arg Trp Arg Arg Cys Leu Val Pro
        175             180                 185 aga ccg ggc ggt ctc cca ggg aca agc gcg tcg tca agg acg agg tca      2173
Arg Pro Gly Gly Leu Pro Gly Thr Ser Ala Ser Ser Arg Thr Arg Ser
        190             195                 200 ccg cgc agg acc tgt ggt ggg gca a gtgagtgtct ggctgtctgc              2218
Pro Arg Arg Thr Cys Gly Gly Ala
205             210 tcgagctcgg cacacgtttc tgctacccta cctgtgtgtt tcttcgccgc tgacgtccgt      2278
ggctgacgat cgggtgcag gg  gct cgc cca aca tcg aga tgg acg aga aga      2329
                        Arg Ala Arg Pro Thr Ser Arg Trp Thr Arg Arg
                            215                 220 cgt tcc tga tca aca ggg aga ggg ccg tcg act acc tca act ccc tgg      2377
Arg Ser     Ser Thr Gly Arg Gly Pro Ser Thr Thr Ser Thr Pro Trp
    225             230                 235 aga agg tgt tcg tca acg acc agt acc tca act ggg acc ccg aga acc      2425
Arg Arg Cys Ser Ser Thr Thr Ser Thr Ser Thr Gly Thr Pro Arg Thr
    240             245                 250 gga tca agg tcc gca tca tct ctg cca ggg cgt acc act ccc tct tca      2473
Gly Ser Arg Ser Ala Ser Ser Leu Pro Gly Arg Thr Thr Pro Ser Ser
255             260                 265                 270 tgc aca aca t gtaagccaac ccggcctata ccatactatc atcgtcttcc            2523
Cys Thr Thr ttgttgaggc ggccctagag tataactgga tggggccggg ccgggctcgg tcgcag gt      2581
                                                                    Cys
```

```
gca tcc gcc cca cgg acg agg agc tgg agg act tcg gca cgc cgg act    2629
Ala Ser Ala Pro Arg Thr Arg Ser Trp Arg Thr Ser Ala Arg Arg Thr
275                 280                 285                 290 tca cca tct aca acg cag ggc agt tcc cct gca acc gct aca ccc act    2677
Ser Pro Ser Thr Thr Gln Gly Ser Ser Pro Ala Thr Ala Thr Pro Thr
                295                 300                 305 aca tga cgt cgt cca cga gca tag acc tca acc tcg cca gga ggg aga    2725
Thr     Arg Arg Pro Arg Ala     Thr Ser Thr Ser Pro Gly Gly Arg
                310                 315                 320 tgg tca tca tgg gca cgc agt acg ccg gcg aga tga aga agg ggc tct    2773
Trp Ser Ser Trp Ala Arg Ser Thr Pro Ala Arg     Arg Arg Gly Ser
                325                 330                 335 tcg gcg tca tgc act acc tca tgc cca agc gcg gca tcc tct cgc tgc    2821
Ser Ala Ser Cys Thr Thr Ser Cys Pro Ser Ala Ala Ser Ser Arg Cys
                340                 345                 350 act ccg gct gca ata tgg gca agg acg gcg acg tcg ccc tct tct ttg    2869
Thr Pro Ala Ala Ile Trp Ala Arg Thr Ala Thr Ser Pro Ser Ser Leu
                355                 360                 365 gcc tct cag gtaaacatgg atgagaagag atggttgtgc gtggcgccgc            2918
Ala Ser Gln
            370 cacctgccca agtcgcattc gcttaccttg tccttcgtgt catgtacgtc gtcttatatc   2978 cgctgatctt acaacag gta ccg gga aga cga cgc tgt cga cgg atc aca     3028
                Val Pro Gly Arg Arg Arg Cys Arg Arg Ile Thr
                                    375                 380 aca ggc ttc tga tcg gcg acg acg agc act gct gga gcg aca atg gcg    3076
Thr Gly Phe     Ser Ala Thr Thr Ser Thr Ala Gly Ala Thr Met Ala
                385                 390                 395 tgt cca aca tcg agg gag gct gct acg cca agt gca tcg acc tgg cgc    3124
Cys Pro Thr Ser Arg Glu Ala Ala Thr Pro Ser Ala Ser Thr Trp Arg
                400                 405                 410 agg aga aag aac ctg ata ttt gga acg cca tca agt ttg gaa ctg        3169
Arg Arg Lys Asn Leu Ile Phe Gly Thr Pro Ser Ser Leu Glu Leu
                415                 420                 425 gtacgtactt gtctcgaact ttcggtttct tcctttcttt cgccggctga attgggttgg   3229
gtagctgaac tgaatgtttc tgctccag tgc tgg aga acg tgg tct ttg atg     3281
                                Cys Trp Arg Thr Trp Ser Leu Met
                                            430                 435 agc ata ctc gtg aag tcg act acg ccg aca act ctg tca ccg            3323
Ser Ile Leu Val Lys Ser Thr Thr Pro Thr Thr Leu Ser Pro
                440                 445 gtaaatgtcg cgtccctagt ccctactaca cggacaagca ccaccaaaga aaaaaaaaa    3383 acttgtgtgg tctcatctca tgcatgcatg cgctgttgt taattcttgc attgattgta    3443
gggatgaaag taggatggga aaatcccgta ccgaccgtta tcgtataacc gattttgtta    3503
gttttatccc gatcgatttc gaacccgagg taaaaaacga aaacggaacg gaaacgggat    3563
atacaaaacg gtaaacggaa acggaaacgg tagagctagt ttcccgaccg tttcaccggg    3623
atcccgtttt taatcggaat gatcccgttt cgttaccgta ttttctaatt cgggatgact    3683
gcaatatggc cagctccaac tcccatccat aaccactgag gcccagccca tgtaagaaat    3743
acctagcgaa cgctgctctg cctctctccc aggcggccag gcaccacacg agtaacagca    3803
tcacacattc acacgccgcc acgcgcccac gccggagtcc ggacgccgcc agccgcacgc    3863
cgacgccggc gacgcgtctc gctctcgcct gctctctccg actctccctg tctcccagcc    3923
ggccggccgc tgggctgcac caggcaccac acgcggtgac ggccgtgacg cggcacgccg    3983
```

-continued

```
gacgcagacg ccgccatcca cggtccgccc tccactccac tgctcgcgac tcgcccatcc    4043
gcgccgcggt ccgccatcc gcccagacct ccactccact gctcgcccat ccgcggtccg    4103
cccatccgcc atccgccatc tgcggtcagc gttcctccag acctccactg ctcggcgctc    4163
gcccatccgg ccatccgcgg tctccctgtc tccacggctg ctcacaggct cacagcactt    4223
agcagtacag cacgtcagca ccattgcacc aagctgttgt gtcatttgtg tgctgtccag    4283
gggctctgca acacctgctg attgctgtcc agccgtccag gtgctcacaa gtcacagcag    4343
tacagcacca agctgattgc tgaacacctg ctgtccaggg ctctgctctc cacttcggct    4403
agccggctac gactccattc ctcagatgac gcctccggtt ggaaataatc tccctcagg    4463 ctcagccata agattggcca agttgatgct gttattgctg ctgcaacaaa tcatgagaat    4523
catatggatg aggtatttaa agattattat ttacttcgtg catgggctat taatttgcta    4583
ttattcacta ctgtttttgat gcatgggctg tttgctgtcg ccttgttttg atgcatgcgc    4643
cttgctgccc agccgtgtta tactccctgc atggctggca ttaacagatt tttgatctca    4703
ctgcatgcgc cttgtcgcct tgttttgatt ggctgctagc tgctagctgt taggctccca    4763
gctgttaggc gctagctgct agctgcctag ctcccagccg tgttagttca cagattcatg    4823
ttctcctata tgtatttatt tatactccct gcatatcaat tcatgttctt ctatatgtat    4883
ttatttatcc aaaactgact tattttttgtg tattaacagg atgaagacgc aatagaattt    4943
tctaagaata atgaagatgt agcaagtggc tcctctccat gagcaatgtg tcttatgtt    5003 gttgacagat gagccttggt tgtaatagtt tatgcatgct aagtgatcca gatgtgagca    5063
agtgattatg aatatgtgtt ttaaacttta tattgtgtca tgtgtgctag tagacttata    5123
tggcttctta tgttagccaa gagcccaaga cttatcactt atgtgctaca ttaaactatg    5183
tgtgctccag atttatatgg attttatcta tgtttaatta agacttgtgt ttacaatttt    5243
ttatatttgt ttttaagttt tgaatatatg ttttcatgtg tgattttacc gaacaaaaat    5303
accggttccc gtccgatttc gactttaacc cgaccggatc gtatcggttt tcgattaccg    5363
tatttatccc gttcgttttc gttaccggta tatcccgttt tcgtttccgt cccgcaagtt    5423
aaatatgaaa atgaaaacgg tagaggtatt ttaccgaccg ttcccgaccg ttttcatccc    5483 tacagacag aga aca ctc ggg ctg cct acc cga tcg agt aca tcc cca acg    5534
              Arg Thr Leu Gly Leu Pro Thr Arg Ser Ser Thr Ser Pro Thr
              450              455                  460 cca aga tac cat gcg tcg gcc cgc acc cca aga atg tga tcc tcc tgg      5582
Pro Arg Tyr His Ala Ser Ala Arg Thr Pro Arg Met     Ser Ser Trp
    465               470               475 cgt gcg acg cct tcg gcg tgc tcc cgc cgg tga gca agc tga acc tgg      5630
Arg Ala Thr Pro Ser Ala Cys Ser Arg Arg     Ala Ser     Thr Trp
    480               485               490 cgc aga cca tgt acc act tca tca gcg ggt aca ccg ctc tgg tcg ccg      5678
Arg Arg Pro Cys Thr Thr Ser Ser Ala Gly Thr Pro Leu Trp Ser Pro
        495               500               505 gca cgg agg acg gca tca agg agc cgc agg cca cct tct ccg cct gct      5726
Ala Arg Arg Thr Ala Ser Arg Ser Arg Arg Pro Pro Ser Pro Pro Ala
    510               515               520 tcg gcg cgg cct tca tca tgc tcc acc cga cca agt acg ccg cca tgc      5774
Ser Ala Arg Pro Ser Ser Cys Ser Thr Arg Pro Ser Thr Pro Pro Cys
525               530               535               540 tcg ccg aga aga tgc aga agt acg gcg cca ccg ggt ggc tcg tca aca      5822
Ser Pro Arg Arg Cys Arg Ser Thr Ala Pro Pro Gly Gly Ser Ser Thr
        545               550               555 ccg gct ggt ctg gtg gca g gtacgcacgc ggcacgaccg tcacggtttg           5871
Pro Ala Gly Leu Val Ala
```

-continued

```
Pro Ala Gly Leu Val Ala
            560 gtttgcttcc ggcagttgca cacagctcgt gttcggtatg ggaaaccgta ggtttcattg    5931 tgtgacggtc gcttttgctt gtcag gt  acg gcg tgg gca aga gga tca ggc       5982
                              Gly Thr Ala Trp Ala Arg Gly Ser Gly
                                      565             570 ttc cct aca cca gaa aga tca tcg acg cca tcc act ccg gcg agc tcc       6030
Phe Pro Thr Pro Glu Arg Ser Ser Thr Pro Ser Thr Pro Ala Ser Ser
        575             580             585 tta ccg cca act acc aga aga ccg agg tgt ttg gcc tgg aga tcc cca       6078
Leu Pro Pro Thr Thr Arg Arg Pro Arg Cys Leu Ala Trp Arg Ser Pro
        590             595             600 ctg aga tca acg gcg tgc cgt cgg aaa tcc tcg acc cga tca aca cc        6125
Leu Arg Ser Thr Ala Cys Arg Arg Lys Ser Ser Thr Arg Ser Thr Pro
    605             610             615 gtatgctctg agtctcacct cacgagctcg cttcatcagt catcttgaac tatacaccct    6185
ctgaccaatt tcgaacttga caaatgctgt atatatgcag t gga cgg aca agg ccg     6241
                                              Gly Arg Thr Arg Pro
                                                          620 cgt aca agg aga atc tcc tga ggc tcg gcg ggc tct tca aga aga act       6289
Arg Thr Arg Arg Ile Ser     Gly Ser Ala Gly Ser Ser Arg Arg Thr
625             630             635 tcg agg tgt tcg cca gct aca aga tcg ggg acg aca gca gcc tga ctg       6337
Ser Arg Cys Ser Pro Ala Thr Arg Ser Gly Thr Thr Ala Ala     Leu
640             645             650 acg aga tcc tcg ccg cag gcc cca act tct ga actaaagcaa tggatccgga      6389
Thr Arg Ser Ser Pro Gln Ala Pro Thr Ser
655             660 tgaataaaac gatggtgtgt gtgcgtgggt gcgtgtgaag atgattacga cgacgacgac    6449
gaaaaaaaag gtgttggatc gatgagccaa catagtaata gattagctgg gtattgtcat    6509
gggtgcgtct ggtgttgtta tctataaggc tgtttgcctg tcccaagcag ctatcatatt    6569
ctatttcaaa ttctattctg taagcgtgta gttcaaaaca atgctttaca caaccatatg    6629
cacagtctta tctcaggttg gtctgttcta tcagcttgtt gggaaaagtt tgcgtgtgct    6689
tgtatcttgc cccctgtact ctctctggtt tctgaatttg gatatgaaac agcttgatcg    6749
cgatcaccat tggttcggta tgtcatggca gga                                  6782
```

<210> SEQ ID NO 2
<211> LENGTH: 6782
<212> TYPE: DNA
<213> ORGANISM: Artificial Sequence
<220> FEATURE:
<223> OTHER INFORMATION: SYNTHESIZED
<220> FEATURE:
<221> NAME/KEY: source
<222> LOCATION: (1)..(6782)
<223> OTHER INFORMATION: /organism="unspecified"/mol_type="genomic DNA"
<220> FEATURE:
<221> NAME/KEY: exon
<222> LOCATION: (712)..(994)
<223> OTHER INFORMATION: /label=Exon 1
<220> FEATURE:
<221> NAME/KEY: exon
<222> LOCATION: (1702)..(1904)
<223> OTHER INFORMATION: /label=Exon 2
<220> FEATURE:
<221> NAME/KEY: exon
<222> LOCATION: (2045)..(2198)
<223> OTHER INFORMATION: /label=Exon 3
<220> FEATURE:
<221> NAME/KEY: exon
<222> LOCATION: (2298)..(2483)

```
<223> OTHER INFORMATION: /label=Exon 4
<220> FEATURE:
<221> NAME/KEY: exon
<222> LOCATION: (2580)..(2878)
<223> OTHER INFORMATION: /label=Exon 5
<220> FEATURE:
<221> NAME/KEY: exon
<222> LOCATION: (2996)..(3169)
<223> OTHER INFORMATION: /label=Exon 6
<220> FEATURE:
<221> NAME/KEY: exon
<222> LOCATION: (3258)..(3323)
<223> OTHER INFORMATION: /label=Exon 7
<220> FEATURE:
<221> NAME/KEY: exon
<222> LOCATION: (3441)..(3789)
<223> OTHER INFORMATION: /label=Exon 8
<220> FEATURE:
<221> NAME/KEY: exon
<222> LOCATION: (3905)..(4073)
<223> OTHER INFORMATION: /label=Exon 9
<220> FEATURE:
<221> NAME/KEY: exon
<222> LOCATION: (4174)..(4317)
<223> OTHER INFORMATION: /label=Exon 10
<220> FEATURE:
<221> NAME/KEY: 3'UTR
<222> LOCATION: (4318)..(6753)
<220> FEATURE:
<221> NAME/KEY: misc_feature
<222> LOCATION: (4459)..(4462)
<223> OTHER INFORMATION: /label=Ds Insertion Site 5' Flanking Repeat
<220> FEATURE:
<221> NAME/KEY: misc_feature
<222> LOCATION: (4463)..(4466)
<223> OTHER INFORMATION: /label=Ds Insertion Site 5' Flanking Repeat
<220> FEATURE:
<221> NAME/KEY: misc_feature
<222> LOCATION: (4467)..(6510)
<223> OTHER INFORMATION: /label=Ds Element
<220> FEATURE:
<221> NAME/KEY: misc_feature
<222> LOCATION: (6511)..(6514)
<223> OTHER INFORMATION: /label=Ds Insertion Site 3' Flanking Repeat
<220> FEATURE:
<221> NAME/KEY: misc_feature
<222> LOCATION: (6515)..(6518)
<223> OTHER INFORMATION: /label=Ds Insertion Site 3' Flanking Repeat

<400> SEQUENCE: 2
gtagggtagt acaattcagg gcgtgtagac aaatcagtgg agccgataag tttatgcata      60
agaaaagtca gtgattttat taactacttt ctctcccaga acaaacttcg caaggcacag     120
ctgtcgcagt cacaccgatt tggctagcct ccctccggtt agcaactttg gagtattagc     180
aagcatacag gagtaaacaa gtagctaagc aaatgcagat tcagaataat gcaaatattg     240
tgttaagccg cagatggtat aaacagaaga cgtgcaaata tttgttatta gaaaaaaaac     300
gttacagaaa aggggggaat ttcaaaaagg ataagctcca ctgctgctcc agagtgcaaa     360
aacccaaacc caacccggaa cgaaagcgcc gccgccgttg aatggtcggg tagaggacgt     420
aaccatggtt cactgccggg ccctttaaaa gccgagccag gctcgtccca tccgccccac     480
gaccgcttgg cgcttcatca ctcgtttcct ttcgaaagcc cgcgcacgca cgtcggtcgt     540
cccgtacgtg tgcccgtcta tctatcctcc tcgactctgt cgtgtctctt caactccgag     600
agtgtccggg agcagagagc atcgatcaat ggcggggttt ggtctggtct ggtctggtcc     660
catcccagca gggtcgctaa tgcgcgctcg ctgctgcttc tctctctgca g gag cag     717
                                                         Glu Gln
                                                           1 gac ctc gat cgg ccg aga tgg cga cgc cga acg ggc ttg cgc gga tcg     765
Asp Leu Asp Arg Pro Arg Trp Arg Arg Arg Thr Gly Leu Arg Gly Ser
```

-continued

```
              5                10               15 aga cga ccg gga aga aga agc agg aca acg gcg tgt ggt acg acg aca      813
Arg Arg Pro Gly Arg Arg Ser Arg Thr Thr Ala Cys Gly Thr Thr Thr
    20                25               30 gct cgg cgc cgg tgc gcg cgc aga cca tcg acg agc tgc act cgc tgc      861
Ala Arg Arg Arg Cys Ala Arg Arg Pro Ser Thr Ser Cys Thr Arg Cys
35                40               45               50 agc gga agc ggt cgg cgc cca gca cgc cca agc ggt cgg cgc cca cca      909
Ser Gly Ser Gly Arg Arg Pro Ala Arg Pro Ser Gly Arg Arg Pro Pro
              55               60               65 cgc cca tca agg gcg gcg ccc act cgc cct tcg ccg tcg cga tct ccg      957
Arg Pro Ser Arg Ala Ala Pro Thr Arg Pro Ser Pro Ser Arg Ser Pro
         70               75               80 agg agg agc gcc aca cgc agc aga tgc agt cca tca g gtgacgttcg        1004
Arg Arg Ser Ala Thr Arg Ser Arg Cys Ser Pro Ser
         85               90 tcctttctca gctagcatga ttctgccgcc actaggcact agctaagtag ctagcctgcc   1064
gctataaacg aattggtgaa aacgatttct cgatttggtt gggttttggt tcattactga   1124
ataataatag cttaacgaca atggccaacc caggcacatg aaaggtaagc ggagatgagt   1184
tcctttaccc ttttgggaaa ggaaaaaaaa aaagacaaaa taatttggcg tctgctggac   1244
ttcctctggg agaagaagga acggaacaaa accagagctc tgccaccgac gtcagagccc   1304
ggcccgttta cgttgacaat acacacactg cctcgtgggc cctcttaaga tagcacttgg   1364
tgtgagttgt ggacttcatt agaaaaaaag taaaaggatg gagaagatag aaataggtaa   1424
aaacaaaagg gtgacgcacg aaacgaacaa gcattaggta ataggtacta caaacacgca   1484
gcttgacgcg acaccacggt cgccgtcggc cacgcaacgt gctcctttat ctctgcagga   1544
aacctagtaa tccttcccga aaatctgtac gtccttcggg ggtcggctgt gtcctcccgg   1604
tctcgcgcac cactaaccat ttttggtgct gataatcggg agcgtagcgt aattaccact   1664
aaacattttt tttcccgatc tctcgtgatg gatgcag tg    cgt cgt tgg cgt ctc  1718
                                               Val Arg Arg Trp Arg Leu
                                               95               100 tga cgc gtg aaa ccg ggc cga aag tgg tca agg gcg acc cgg cgg cga      1766
    Arg Val Lys Pro Gly Arg Lys Trp Ser Arg Ala Thr Arg Arg Arg
             105               110               115 agg gag agg ccg ccg cgc agg gcg cgc cat cga cgc cga ggg cgc acc      1814
Arg Glu Arg Pro Pro Arg Arg Ala Arg His Arg Arg Arg Gly Arg Thr
             120               125               130 agc agc acc gcc acc ccg ccg ccc ccg cca tcg ccg tca gcg aca gct      1862
Ser Ser Thr Ala Thr Pro Pro Pro Pro Ser Pro Ser Ala Thr Ala
             135               140               145 ccc tca agt tca ctc atg tgc tca aca acc tct cgc ctg ctg              1904
Pro Ser Ser Ser Leu Met Cys Ser Thr Thr Ser Arg Leu Leu
         150               155               160 gtaagcatcg cataacgcat atgcacaacc tgatcagctt cttcgcgttg cgttgcgatg   1964
cgagagacta actgctgacg gatgcttact ttgtccctct gctgcctgtc actcaaaaac   2024
ctattaaaaa cgaaaaacag agc tgt acg agc agg cca tca agt acg aga agg   2077
                       Ser Cys Thr Ser Arg Pro Ser Ser Thr Arg Arg
                                165               170 ggt cgt tca tca cgt cca ccg gcg cgc tgg cga cgc tgt ctg gtg cca     2125
Gly Arg Ser Ser Arg Pro Pro Ala Arg Trp Arg Arg Cys Leu Val Pro
         175               180               185 aga ccg ggc ggt ctc cca ggg aca agc gcg tcg tca agg acg agg tca     2173
Arg Pro Gly Gly Leu Pro Gly Thr Ser Ala Ser Ser Arg Thr Arg Ser
    190               195               200
```

-continued

```
ccg cgc agg acc tgt ggt ggg gca a gtgagtgtct ggctgtctgc        2218
Pro Arg Arg Thr Cys Gly Gly Ala
205                 210 tcgagctcgg cacacgtttc tgctacccta cctgtgtgtt tcttcgccgc tgacgtccgt  2278
ggctgacgat cgggtgcag gg gct cgc cca aca tcg aga tgg acg aga aga   2329
                       Arg Ala Arg Pro Thr Ser Arg Trp Thr Arg Arg
                               215                 220 cgt tcc tga tca aca ggg aga ggg ccg tcg act acc tca act ccc tgg   2377
Arg Ser     Ser Thr Gly Arg Gly Pro Ser Thr Thr Ser Thr Pro Trp
    225                 230                 235 aga agg tgt tcg tca acg acc agt acc tca act ggg acc ccg aga acc   2425
Arg Arg Cys Ser Ser Thr Thr Ser Thr Ser Thr Gly Thr Pro Arg Thr
    240                 245                 250 gga tca agg tcc gca tca tct ctg cca ggg cgt acc act ccc tct tca   2473
Gly Ser Arg Ser Ala Ser Ser Leu Pro Gly Arg Thr Thr Pro Ser Ser
255                 260                 265                 270 tgc aca aca t gtaagccaac ccggcctata ccatactatc atcgtcttcc         2523
Cys Thr Thr ttgttgaggc ggccctagag tataactgga tggggccggg ccgggctcgg tcgcag gt  2581
                                                             Cys gca tcc gcc cca cgg acg agg agc tgg agg act tcg gca cgc cgg act   2629
Ala Ser Ala Pro Arg Thr Arg Ser Trp Arg Thr Ser Ala Arg Arg Thr
275                 280                 285                 290 tca cca tct aca acg cag ggc agt tcc cct gca acc gct aca ccc act   2677
Ser Pro Ser Thr Thr Gln Gly Ser Ser Pro Ala Thr Ala Thr Pro Thr
                295                 300                 305 aca tga cgt cgt cca cga gca tag acc tca acc tcg cca gga ggg aga   2725
Thr     Arg Arg Pro Arg Ala     Thr Ser Thr Ser Pro Gly Gly Arg
                310                 315                 320 tgg tca tca tgg gca cgc agt acg ccg gcg aga tga aga agg ggc tct   2773
Trp Ser Ser Trp Ala Arg Ser Thr Pro Ala Arg     Arg Arg Gly Ser
                325                 330                 335 tcg gcg tca tgc act acc tca tgc cca agc gcg gca tcc tct cgc tgc   2821
Ser Ala Ser Cys Thr Thr Ser Cys Pro Ser Ala Ala Ser Ser Arg Cys
                340                 345                 350 act ccg gct gca ata tgg gca agg acg gcg acg tcg ccc tct tct ttg   2869
Thr Pro Ala Ala Ile Trp Ala Arg Thr Ala Thr Ser Pro Ser Ser Leu
                355                 360                 365 gcc tct cag gtaaacatgg atgagaagag atggttgtgc gtggcgccgc          2918
Ala Ser Gln
            370 cacctgccca agtcgcattc gcttaccttg tccttcgtgt catgtacgtc gtcttatatc  2978 cgctgatctt acaacag gta ccg gga aga cga cgc tgt cga cgg atc aca   3028
                    Val Pro Gly Arg Arg Arg Cys Arg Arg Ile Thr
                            375                 380 aca ggc ttc tga tcg gcg acg acg agc act gct gga gcg aca atg gcg   3076
Thr Gly Phe     Ser Ala Thr Thr Ser Thr Ala Gly Ala Thr Met Ala
                385                 390                 395 tgt cca aca tcg agg gag gct gct acg cca agt gca tcg acc tgg cgc   3124
Cys Pro Thr Ser Arg Glu Ala Ala Thr Pro Ser Ala Ser Thr Trp Arg
                400                 405                 410 agg aga aag aac ctg ata ttt gga acg cca tca agt ttg gaa ctg       3169
Arg Arg Lys Asn Leu Ile Phe Gly Thr Pro Ser Ser Leu Glu Leu
                415                 420                 425 gtacgtactt gtctcgaact ttcggtttct tcctttcttt cgccggctga attgggttgg  3229
gtagctgaac tgaatgtttc tgctccag tgc tgg aga acg tgg tct ttg atg   3281
                                 Cys Trp Arg Thr Trp Ser Leu Met
```

```
                                    430                    435 agc ata ctc gtg aag tcg act acg ccg aca act ctg tca ccg          3323
Ser Ile Leu Val Lys Ser Thr Thr Pro Thr Thr Leu Ser Pro
            440                445 gtaaatgtcg cgtccctagt ccctactaca cggacaagca ccaccaaaga aaaaaaaaa    3383 acttgtgtgg tctcatctca tgcatgcatg gcgctgttgt taattcttgc attgcag      3440 aga aca ctc ggg ctg cct acc cga tcg agt aca tcc cca acg cca aga    3488
Arg Thr Leu Gly Leu Pro Thr Arg Ser Ser Thr Ser Pro Thr Pro Arg
450                455                460                465 tac cat gcg tcg gcc cgc acc cca aga atg tga tcc tcc tgg cgt gcg    3536
Tyr His Ala Ser Ala Arg Thr Pro Arg Met     Ser Ser Trp Arg Ala
                470                475                    480 acg cct tcg gcg tgc tcc cgc cgg tga gca agc tga acc tgg cgc aga    3584
Thr Pro Ser Ala Cys Ser Arg Arg     Ala Ser     Thr Trp Arg Arg
                485                490 cca tgt acc act tca tca gcg ggt aca ccg ctc tgg tcg ccg gca cgg    3632
Pro Cys Thr Thr Ser Ser Ala Gly Thr Pro Leu Trp Ser Pro Ala Arg
495                500                505                510 agg acg gca tca agg agc cgc agg cca cct tct ccg cct gct tcg gcg    3680
Arg Thr Ala Ser Arg Ser Arg Arg Pro Pro Ser Pro Pro Ala Ser Ala
                515                520                525 cgg cct tca tca tgc tcc acc cga cca agt acg ccg cca tgc tcg ccg    3728
Arg Pro Ser Ser Cys Ser Thr Arg Pro Ser Thr Pro Pro Cys Ser Pro
                530                535                540 aga aga tgc aga agt acg gcg cca ccg ggt ggc tcg tca aca ccg gct    3776
Arg Arg Cys Arg Ser Thr Ala Pro Pro Gly Gly Ser Ser Thr Pro Ala
            545                550                555 ggt ctg gtg gca g gtacgcacgc ggcacgaccg tcacggtttg gtttgcttcc      3829
Gly Leu Val Ala
            560 ggcagttgca cacagctcgt gttcggtatg ggaaaccgta ggtttcattg tgtgacggtc   3889 gctttgctt gtcag gt  acg gcg tgg gca aga gga tca ggc ttc cct aca    3939
                    Gly Thr Ala Trp Ala Arg Gly Ser Gly Phe Pro Thr
                        565                570 cca gaa aga tca tcg acg cca tcc act ccg gcg agc tcc tta ccg cca    3987
Pro Glu Arg Ser Ser Thr Pro Ser Thr Pro Ala Ser Ser Leu Pro Pro
575                580                585                590 act acc aga aga ccg agg tgt ttg gcc tgg aga tcc cca ctg aga tca    4035
Thr Thr Arg Arg Pro Arg Cys Leu Ala Trp Arg Ser Pro Leu Arg Ser
                595                600                605 acg gcg tgc cgt cgg aaa tcc tcg acc cga tca aca cc  gtatgctctg      4083
Thr Ala Cys Arg Arg Lys Ser Ser Thr Arg Ser Thr Pro
            610                615 agtctcacct cacagctcg cttcatcagt catcttgaac tatacaccct ctgaccaatt    4143
tcgaacttga caaatgctgt atatatgcag t gga cgg aca agg ccg cgt aca      4195
                                    Gly Arg Thr Arg Pro Arg Thr
                                        620                625 agg aga atc tcc tga ggc tcg gcg ggc tct tca aga aga act tcg agg    4243
Arg Arg Ile Ser     Gly Ser Ala Gly Ser Ser Arg Arg Thr Ser Arg
            630                635                640 tgt tcg cca gct aca aga tcg ggg acg aca gca gcc tga ctg acg aga    4291
Cys Ser Pro Ala Thr Arg Ser Gly Thr Thr Ala Ala     Leu Thr Arg
            645                650                655 tcc tcg ccg cag gcc cca act tct ga actaaagcaa tggatccgga            4337
Ser Ser Pro Gln Ala Pro Thr Ser
                660 tgaataaaac gatggtgtgt gtgcgtgggt gcgtgtgaag atgattacga cgacgacgac   4397
```

-continued

```
gaaaaaaaag gtgttggatc gatgagccaa catagtaata gattagctgg gtattgtcat    4457
gggtgggtgt agggatgaaa gtaggatggg aaaatcccgt accgaccgtt atcgtataac    4517
cgattttgtt agttttatcc cgatcgattt cgaacccgag gtaaaaaacg aaaacggaac    4577
ggaaacggga tatacaaaac ggtaaacgga aacggaaacg gtagagctag tttcccgacc    4637
gtttcaccgg gatcccgttt ttaatcggaa tgatcccgtt tcgttaccgt attttctaat    4697
tcgggatgac tgcaatatgg ccagctccaa ctcccatcca taaccactga ggcccagccc    4757
atgtaagaaa tacctagcga acgctgctct gcctctctcc caggcggcca ggcaccacac    4817
gagtaacagc atcacacatt cacacgccgc cacgcgccca cgccggagtc cggacgccgc    4877
cagccgcacg ccgacgccgg cgacgcgtct cgctctcgcc tgctctctcc gactctccct    4937
gtctcccagc cggccggccg ctgggctgca ccaggcacca cacgcggtga cggccgtgac    4997
gcggcacgcc ggacgcagac gccgccatcc acggtccgcc ctccactcca ctgctcgcga    5057
ctcgcccatc cgcgccgcgg tccgcccatc cgcccagacc tccactccac tgctcgccca    5117
tccgcggtcc gcccatccgc catccgccat ctgcggtcag cgttcctcca gacctccact    5177
gctcggcgct cgcccatccg gccatccgcg gtctccctgt ctccacggct gctcacaggc    5237
tcacagcact tagcagtaca gcacgtcagc accattgcac caagctgttg tgtcatttgt    5297
gtgctgtcca ggggctctgc aacacctgct gattgctgtc cagccgtcca ggtgctcaca    5357
agtcacagca gtacagcacc aagctgattg ctgaacacct gctgtccagg gctctgctct    5417
ccacttcggc tagccggcta cgactccatt cctcagatga cgcctccggt tggaaataat    5477
cctccctcag gctcagccat aagattggcc aagttgatgc tgttattgct gctgcaacaa    5537
atcatgagaa tcatatggat gaggtattta aagattatta tttacttcgt gcatgggcta    5597
ttaatttgct attattcact actgttttga tgcatgggct gtttgctgtc gccttgtttt    5657
gatgcatgcg ccttgctgcc cagccgtgtt atactccctg catggctggc attaacagat    5717
ttttgatctc actgcatgcg ccttgtcgcc ttgtttttgat tggctgctag ctgctagctg    5777
ttaggctccc agctgttagg cgctagctgc tagctgccta gctcccagcc gtgttagttc    5837
acagattcat gttctcctat atgtatttat ttatactccc tgcatatcaa ttcatgttct    5897
tctatatgta tttatttatc caaaactgac ttattttgt gtattaacag gatgaagacg     5957
caatagaatt ttctaagaat aatgaagatg tagcaagtgg ctcctctcca tgagcaatgt    6017
gtcttatgtt tgttgacaga tgagccttgg ttgtaatagt ttatgcatgc taagtgatcc    6077
agatgtgagc aagtgattat gaatatgtgt tttaaacttt atattgtgtc atgtgtgcta    6137
gtagacttat atggcttctt atgttagcca agagcccaag acttatcact tatgtgctac    6197
attaaactat gtgtgctcca gatttatatg gattttatct atgtttaatt aagacttgtg    6257
tttacaattt tttatatttg tttttaagtt ttgaatatat gttttcatgt gtgattttac    6317
cgaacaaaaa taccggttcc cgtccgattt cgactttaac ccgaccggat cgtatcggtt    6377
ttcgattacc gtatttatcc cgttcgtttt cgttaccggt atatcccgtt ttcgtttccg    6437
tcccgcaagt taaatatgaa aatgaaaacg gtagaggtat tttaccgacc gttcccgacc    6497
gttttcatcc ctacgtccgt ctggtgttgt tatctataag gctgtttgcc tgtcccaagc    6557
agctatcata ttctatttca aattctattc tgtaagcgtg tagttcaaaa caatgcttta    6617
cacaaccata tgcacagtct tatctcaggt tggtctgttc tatcagcttg ttgggaaaag    6677
tttgcgtgtg cttgtatctt gcccctgta ctctctctgg tttctgaatt tggatatgaa    6737
```

-continued

```
acagcttgat cgcgatcacc attggttcgg tatgtcatgg cagga                    6782

<210> SEQ ID NO 3
<211> LENGTH: 19
<212> TYPE: DNA
<213> ORGANISM: Artificial Sequence
<220> FEATURE:
<223> OTHER INFORMATION: SYNTHESIZED

<400> SEQUENCE: 3
cccgatcaac acctggacg                                                 19

<210> SEQ ID NO 4
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 4
aatcatcttc acacgcaccc a                                              21

<210> SEQ ID NO 5
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 5
ggcatcagga accctgagga aa                                             22

<210> SEQ ID NO 6
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 6
gatgtgcagc agccttgtcc tt                                             22
```